(12) United States Patent
Paul et al.

(10) Patent No.: US 12,351,791 B2
(45) Date of Patent: Jul. 8, 2025

(54) PREDICTING THE METABOLIC CONDITION OF A CELL CULTURE

(71) Applicant: HOFFMANN-LA ROCHE INC., Little Falls, NJ (US)

(72) Inventors: Wolfgang Paul, Penzberg (DE); Arthur Mohr, Penzberg (DE); Sayuri Hortsch, Munich (DE)

(73) Assignee: Hoffman-La Roche Inc., Little Falls, NJ (US)

( * ) Notice: Subject to any disclaimer, the term of this patent is extended or adjusted under 35 U.S.C. 154(b) by 1004 days.

(21) Appl. No.: 16/907,786

(22) Filed: Jun. 22, 2020

(65) Prior Publication Data
US 2020/0377844 A1    Dec. 3, 2020

Related U.S. Application Data

(63) Continuation of application No. PCT/EP2019/050006, filed on Jan. 2, 2019.

(30) Foreign Application Priority Data

Dec. 29, 2017    (EP) ..................................... 17211217

(51) Int. Cl.
*G06N 20/00*    (2019.01)
*C12M 1/34*    (2006.01)
(Continued)

(52) U.S. Cl.
CPC ............ *C12M 41/46* (2013.01); *C12M 41/38* (2013.01); *C12N 5/0018* (2013.01); *G06N 3/02* (2013.01); *G06N 20/00* (2019.01); *G16B 5/00* (2019.02)

(58) Field of Classification Search
CPC ..... C12M 41/46; C12M 41/38; C12N 5/0018; G06N 3/02; G06N 20/00; G01N 33/5005; G16B 5/00; G16B 5/30; G16B 40/20
See application file for complete search history.

(56) References Cited

FOREIGN PATENT DOCUMENTS

| JP | 2005-034149 A | 2/2005 |
|----|---------------|--------|
| JP | 2005-293394 A | 10/2005 |

(Continued)

OTHER PUBLICATIONS

Huang et al., Quantitative Intracellular Flux Modeling and Applications in Biotherapeutic Development and Production Using CHO Cell Cultures, 2017 Wiley Periodicals, Inc., pp. 2717-2728 (Year: 2017).*

(Continued)

*Primary Examiner* — Olivia M. Wise
*Assistant Examiner* — Mary C Leverett
(74) *Attorney, Agent, or Firm* — Harness, Dickey & Pierce, P.L.C.

(57) ABSTRACT

The invention relates to a method for predicting the metabolic condition of a cell culture of cells of a specific cell type. The method comprises providing (102) a metabolic model (402) of a cell of the specific cell type and carrying out the following steps at each of a plurality of points in time during the cultivation of the cell culture: receiving (106) measured concentrations of several extracellular metabolites and a measured cell density in the culture medium; inputting (108) the received measured values as input parameter values into a trained machine learning program logic—MLP (218); predicting (110) extracellular flows (408) of the extracellular metabolites at a future point in time by means of the MLP; carrying out (112) a metabolic flow analysis for calculating the intracellular flows at the future point in time on the basis of the predicted extracellular flows and the stoichiometric equations of the metabolic model.

19 Claims, 26 Drawing Sheets

(51) Int. Cl.
C12N 5/00 (2006.01)
G06N 3/02 (2006.01)
G16B 5/00 (2019.01)

(56) References Cited

FOREIGN PATENT DOCUMENTS

| JP | 2007-047994 A | 2/2007 |
|----|---------------|--------|
| JP | 2013-085516 A | 5/2013 |

OTHER PUBLICATIONS

Gregory Stephanopoulos, Emerging Directions in Computer Applications to Biotechnology: Upgrading the Information Content of Biological Data, 1999, Annual Reviews in Control 23, pp. 61-69 (Year: 1999).*
Aurich, Maike K., et al. "Prediction of intracellular metabolic states from extracellular metabolomic data." Metabolomics 11 (2015):603-619. (Year: 2015).*
Bareither, Rachel, and David Pollard. "A review of advanced small-scale parallel bioreactor technology for accelerated process development: Current state and future need." Biotechnology progress 27.1 (2011): 2-14. (Year: 2011).*
R.T.J.M. van der Heijden et al., 'Linear Constraint Relations in Biochemical Reaction Systems: I. Classification of the Calculability and the Balanceability of Conversion Rates,' *Biotechnology and Bioengineering*, vol. 43, pp. 3-10, 1994.
Steffen Klamt et al., 'Calculability Analysis in Undetermined Metabolic Networks Illustrated by a Model of the Central Metabolism in Purple Sulfur Bacteria,' *Biotechnology and Bioengineering*, vol. 77, No. 7, Mar. 30, 2002, pp. 734-751.
Frantisek Madron, 'A New Approach to the Identification of Gross Errors in Chemical Engineering Measurements,' *Chemical Engineering Science*, vol. 40, No. 10, pp. 1855-1860, 1985.
Wolfgang Wiechert, '13C Metabolic Flux Analysis,' *Metabolic Engineering*, vol. 3, pp. 195-206, 2001.
Claudia Altamirano et al., 'Consideration on the lactate consumption by CHO cells in the presence of galactose,' *Journal of Biotechnology*, vol. 125, pp. 547-556, 2006.
Karthik Raman et al., 'Flux balance analysis of biological systems: applications and challenges,' *Briefings in Bioinformatics*, vol. 10, No. 4, pp. 435-449, Mar. 15, 2009.
Francisco Llaneras et al., 'A procedure for the estimation over time of metabolic fluxes in scenarios where measurements are uncertain and/or insufficient,' *BMC Bioinformatics*, vol. 8, No. 421, 2007.
Markus W. Covert et al., 'Integrating metabolic, transcriptional regulatory and signal transduction models in *Escherichia coli*,' *Bioinformatics Original Paper*, vol. 24, No. 18, pp. 2044-2050, 2008.
Jamey D. Young et al., "Mapping photoautotrophic metabolism with isotopically nonstationary 13C flux analysis" *Metabolic Engineering*, vol. 13,(6), 2011, pp. 656-665.
Bhanu Chandra Mulukutla et al., 'On metabolic shift to lactate consumption in fed-batch culture of mammalian cells,' *Metabolic Engineering*, vol. 14, pp. 138-149, 2012.
Woo Suk Ahn et al., 'Towards dynamic metabolic flux analysis in CHO cell cultures,' *Journal of Biotechnology*, vol. 7, pp. 61-74, 2012.
Francesca Zagari et al., 'Lactate metabolism shift in CHO cell culture: the role of mitochondrial oxidative activity,' *New Biotechnology*, vol. 30, No. 2, pp. 238-245, Jan. 2013.
Notice of Reasons for Rejection dated Oct. 25, 2021 issued in corresponding Japanese patent application No. 2020-534849.
R.T.J.M. van der Heijden et al., 'Linear Constraint Relations in Biochemical Reaction Systems: II. Diagnosis and Estimation of Gross Errors,' *Biotechnology and Bioengineering*, vol. 43, No. 1, pp. 11-20, Jan. 5, 1994.
International Preliminary Report and Written Opinion for PCT/EP2019/050006 dated Jul. 9, 2020.

International Search Report and Written Opinion for PCT/EP2019/050006 dated Feb. 12, 2019.
Stephen Gang Wu et al: "Rapid Prediction of Bacterial Heterotrophic Fluxomics Using Machine Learning and Constraint Programming", PLOS Computational Biology, vol. 12, No. 4, Apr. 19, 2016 (Apr. 19, 2016), p. e1004838, XP055456302, DOI: 10.1371/journal.pcbi.1004838.
Panagiotou G et al: "Monitoring novel metabolic pathways using metabolomics and machine learning: induction of the phosphoketolase pathway in Aspergillus nidulans cultivations", Metabolomics, Kluwer Academic Publishersplenum Publishers, NL, vol. 3, No. 4, Jun. 13, 2007 (Jun. 13, 2007), pp. 503-516, XP019558233,ISSN: 1573-3890, DOI: 10.1007 /S 11306-007-0061-7.
Nolan R P et al: "Dynamic model of CHO cell metabolism", Metabolic Engineering, Academic Press, US, vol. 13, No. 1, Jan. 1, 2011 (Jan. 1, 2011), pp. 108-124, XP027575832, ISSN: 1096-7176 [retrieved on Dec. 24, 2010] cited in the application.
Zhuangrong Huang et al: "Quantitative intracellular flux modeling and applications in biotherapeutic development and production using CHO cell cultures", Biotechnology and Bioengineering, vol. 114, No. 12, Dec. 1, 2017 (Dec. 1, 2017), pp. 2717-2728, XP055455882,ISSN: 0006-3592, DOI: 10.1002/bit.26384.
A. Sharma: "Seasonal to interannual rainfall probabilistic forecasts for improved water supply management: Part 1—A strategy for system predictor identification", Journal of Hydrology, vol. 239, No. 1-4, Dec. 1, 2000 (Dec. 1, 2000), pp. 232-239, XP055455656, Amsterdam, Nlissn: 0022-1694, DOI: 10.1016/ S0022-1694(00)00346-2 cited in the application.
Altamirano C, Paredes C, Cairo JJ, Godia F (2000). *Improvement of CHO cell culture medium formulation: simultaneous substitution of glucose and glutamine*. Biotechnology Progress 16(1):69-75.
Antoniewicz MR (2013). *Dynamic metabolic flux analysis—tools for probing transient states of metabolic networks*. Current Opinion in Biotechnology 24:1-6.
Chan SHJ, Ji P (2011). *Decomposing flux distributions into elementary flux modes in genome-scale metabolic networks*. Bioinformatics 27(16) 2256-2262.
Cybenko G (1989). *Approximation by Superpositions of a Sigmoidal Function*. Mathematics of Control, Signals, and Systems 2:303-314.
Fernando TMKG, Maier HR, Dandy GC, May R (2005). *Efficient Selection of Inputs for Artificial Neural Network Models*. MODSIM 2005 International Congress on Modelling and Simulation: Modelling and Simulation Society of Australia and New Zealand, Dec. 2005 / Andre Zerger and Robert M. Argent (eds.): pp. 1806-1812.
Funahashi K (1989). *On the Approximate Realization of Continuous Mappings by Neural Networks*. Neural Networks, vol. 2, pp. 183-192.
Goudar C, Biener R, Zhang C, Michaels J, Piret J, Konstantinov K (2006). *Towards Industrial Application of Quasi Real-Time Metabolic Flux Analysis for Mammalian Cell Culture*. Advances in Biochemical Engineering/Biotechnology 101:99-118.
Hacker DL, De Jesus M, Wurm FM (2009). *25 years of recombinant proteins from reactor-grown cells—Where do we go from here?*. Biotechnology Advances vol. 27, Issue 6, 1023-1027.
Hornik K (1991). *Approximation capabilities of multilayer feedforward networks*. Neural Networks vol. 4, pp. 251-257.
Huang YM, Huynh T, Ly L, Noe W, Chang DYH (2005). *Development of Fed-Batch Process Producing Monoclonal Antibodies Using In-House Media*. Animal Cell Technology meets Genomics, 659-661.
Huang YM, Hu W, Rustandi E, Chang K, Yusuf-Makagiansar H, Ryll T (2010). *Maximizing Productivity of CHO Cell-Based Fed-Batch Culture Using Chemically Defined Media Conditions and Typical Manufacturing Equipment*. Biotechnology Progress 26(5): 1400-1410.
Jayapal Kp, Wlaschin KF, Hu WS (2007). *Recombinant Protein Therapeutics from CHO Cells—20 Years and Counting*. CHO Consortium, SBE Special Section: 40-47.
Leader B, Baca QJ, Golan DE (2008). *Protein therapeutics: a summary and pharmacological classification*. Nature Reviews Drug Discovery 7, 21-39.

(56) References Cited

OTHER PUBLICATIONS

Li J, Wong CL, Vijayasankaran N, Hudson T, Amanullah A (2012). *Feeding lactate for CHO cell culture processes: Impact on culture metabolism and performance*. Biotechnology and Bioengineering, vol. 109, Issue 5, pp. 1173-1186.

Luo J, Vijayasankaran N, Autsen J, Santuray R, Hudson T, Amanullah A, Li F (2011). *Comparative Metabolite Analyses to Understand Lactate Metabolism Shift in Chinese Hamster Ovary Cell Culture Process*. Biotechnology and Bioengineering, vol. 109, No. 1.

Mahadevan R, Edwards JS, Doyle FJ 3rd (2002). *Dynamic flux balance analysis of diauxic growth in Escherichia coli*. Biophysical Journal 83(3):1331-1340.

Martinez VS, Dietmair S, Quek LE, Hodson MP, Gray P, Nielsen LK (2013). *Flux balance analysis of CHO cells before and after a metabolic switch from lactate production to consumption*. Biotechnology and Bioengineering 110(2):660-666.

May R, Dandy G, Maier H (2011). *Review of Input Variable Selection Methods for Artificial Neural Networks*. Artificial Neural Networks—Methodological Advances and Biomedical Applications, Prof. Kenji Suzuki (Ed.), ISBN: 978-953-307-243-2, InTech, DOI: 10.5772/16004. Available from: http://www.intechopen.com/books/artificial-neural-networks-methodological-advances-and-biomedical-applications/review-of-input-variable-selection-methods-for-artificial-neural-networks.

Oliveira R (2004). *Combining first principles modelling and artificial neural networks: a general framework*. Computers and Chemical Engineering 28, 755-766.

Omasa T, Onitsuka M, Kim WD (2010). *Cell engineering and cultivation of chinese hamster ovary (CHO) cells*. Current Pharmaceutical Biotechnology 11(3):233-240.

Psichogios DC, Ungar LH (1992). *A Hybrid Neural Network-First Principles Approach to Process Modeling*. AIChE Journal vol. 38, No. 10.

Schubert J, Simutis R, Dors M, Havlik I, Lübbert A (1994). *Hybrid Modelling of Yeast Production Processes*. Chemical Engineering and Technology 17, 10-20.

Teixeira AP, Cunha AE, Clemente JJ, Moreira JL, Cruz HJ, Alves PM, Carrondo MJT, Oliveira R (2005). *Modelling and optimization of a recombinant BHK-21 cultivation process using hybrid grey-box systems*. Journal of Biotechnology 118, 290-303.

Teixeira AP, Alves C, Alves PM, Carrondo MJT, Oliveira R (2007). *Hybrid elementary flux analysis/nonparametric modeling: application for bioprocess control*. BMC Bioinformatics 8:30.

Thompson ML, Kramer MA (1994). *Modeling Chemical Processes Using Prior Knowledge and Neural Networks*. AIChE Journal vol. 40, No. 8.

Vander Heiden MG, Cantley LC, Thompson CB (2009). *Understanding the Warburg effect: the metabolic requirements of cell proliferation*. Science 324, 102-9-1033.

Wang NS, Stephanopoulos G (1983). *Application of Macroscopic Balances to the Identification of Gross Measurement Errors*. Biotechnology and Bioengineering, vol. 23, pp. 2177-2208.

Wilkens CA, Altamirano C, Gerdtzen ZP (2010). *Comparative Metabolic Analysis of Lactate for CHO Cells in Glucose and Galactose*. Biotechnology and Bioprocess Engineering 16: 714-724.

Xie L, Wang DIC (1996). *Energy Metabolism and ATP Balance in Animal Cell Cultivation Using a Stoichiometrically Based Reaction Network*. Biotechnology and Bioengineering, vol. 52, pp. 591-601.

Yugi K, Nakayama Y, Kinoshita A, Tomita M (2005). *Hybrid dynamic/static method for large-scale simulation of metabolism*. Theoretical Biology und Medical Modelling, 2:42.

Young JD (2013). *Metabolic flux rewiring in mammalian cell cultures*. Current Opinion in Biotechnology 24, 1108-1115.

Bishop Christopher M.: Pattern Recognition and Machine Learning. 9. Auflage. New York: Springer Science + Business Media, LLC 2009.

I. Luna, et al., 'Partial Mutual Information Criterion For Modelling Time Series Via Neural Networks,' 11th Information Processing and Management of Uncertainty International Conference, 2006, 2012.

Zhou Jiang, et al., 'Fed-Batch Cell Culture Process Optimization; A Rationally Integrated Approach,' *BioProcess International*, vol. 10, No. 3, Mar. 2012, pp. 40-45.

Thomas Vogl, et al., 'New opportunities by synthetic biology for biopharmaceutical production in *Pichia pastoris*,' *SciVerse ScienceDirect, Current Opinion in Biotechnology*, 2013, vol. 24, pp. 1094-1101.

William A Rodríguez-Limas, et al., 'Virus-like particles: the future of microbial factories and cell-free systems as platforms for vaccine development,' *SciVerse ScienceDirect, Current Opinion in Biotechnology*, 2013, vol. 24, pp. 1089-1093.

Covert MW, Xiao N, Chen TJ, Karr JR (2008). *Integrating metabolic, transcriptional regulatory and signal transduction models in Escherichia coli*. Bioinformatics vol. 24 No. 18, 2044-2050.

Mulukutla BC, Gramer M, Hu WS (2012). *On metabolic shift to lactate consumption in fed-batch culture of mammalian cells*. Metabolic Engineering 14, 138-149.

Wiechert W (2001). $^{13}C$ *Metabolic Flux Analysis*. Metabolic Engineering 3, 195-206.

Final Office Action issued Feb. 18, 2025 in U.S. Appl. No. 18/331,411.

\* cited by examiner

| Reaction No.: | Stoichiometry | |
|---|---|---|
| 1 | Glc$_e$ → G6P | |
| 2 | G6P → 2 Pyr | |
| 3 | Pyr ↔ Lac$_e$ | 412 |
| 4 | Pyr + Oxa → AKG | |
| 5 | AKG → Mal | |
| 6 | Mal → Oxa | |
| 7 | Mal → Pyr | |
| 8 | Pyr + Glu ↔ Ala + AKG | |
| 9 | Ala ↔ Ala$_e$ | |
| 10 | AKG + NH$_3$ ↔ Glu | |
| 11 | Gln ↔ Glu$_e$ | |
| 12 | Gln ↔ Glu + NH$_3$ | |
| 13 | Gln$_e$ ↔ Gln | |
| 14 | NH$_3$ ↔ NH$_{3e}$ | |
| 15 | AKG + Asp → Oxa + Glu | |
| 16 | Asp ↔ Asp$_e$ | |
| 17 | Asn → Asp + NH$_3$ | |
| 18 | Asn$_e$ → Asn | |
| 19 | Ser$_e$ → Ser | |
| 20 | Ser + NH$_3$ → 2 Gly | |
| 21 | Gly ↔ Gly$_e$ | |
| 22 | 0.084 Ala + 0.087 Gln + 0.080 Asp + 0.041 Asn + 0.096 Ser + 0.056 Gly + 0.452 G6P + 0.427 Oxa → Bio + 0.008 Glu + 0.445 Mal + 0.200 Pyr | |
| 23 | 138 Ala + 104 Gln + 106 Gln + 80 Asp + 72 Asn + 316 Ser + 204 Gly → Prod | |

Fig. 4b

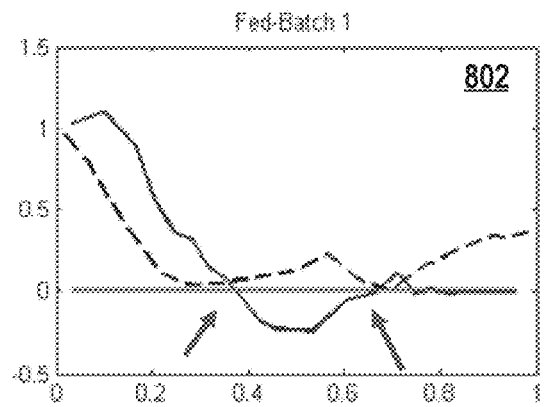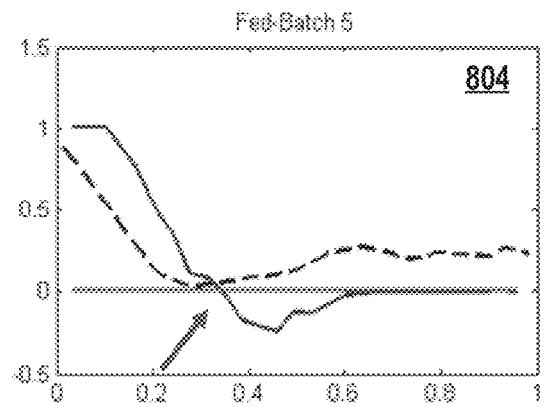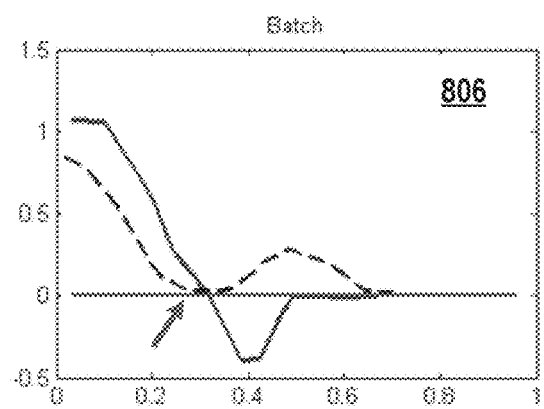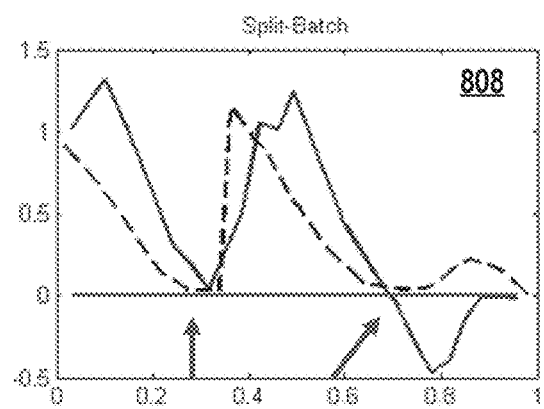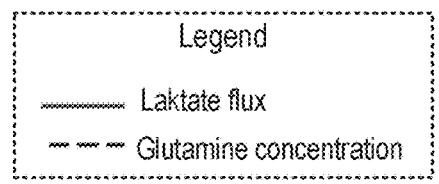
Fig. 9

Fig. 13

| Ausgang | Glc | Lac | Ala | Glu | Gln | NH3 | Asp | Asn | Ser | Gly | TZD | Prod |
|---|---|---|---|---|---|---|---|---|---|---|---|---|
| Eingänge | Bio | Asn | Glc | Bio | Glu | Gln | Asp | Asn | Ser | Gly | Bio | Prod |
| | NH3 | Ala | Gln | Gly | NH3 | Lac | Gln | Asn | Gln | LDH | Gly | Ala |
| | Gln | Gln | NH3 | Gln | Asp | NH3 | Asn | Asp | Ser | Ser | Ser | Asp |
| | Ser | Lac | Lac | Asp | Gly | Ser | Asp | Gln | LDH | NH3 | NH3 | Ser |
| | Ala | Ser | Ser | Ala | Ala | Gly | Asn | Ala | Asp | Ala | LDH | LDH |
| | Asp | Bio | Ala | Asn | Asn | LDH | Ser | Ser | Lac | Asp | Asn | Gln |
| | Asn | NH3 | Asn | Glu | Glu | Ser | Ala | Bio | Ala | Glu | Gln | Glu |
| | Lac | Asp | Bio | LDH | Glc | Gly | Gly | Glu | Gly | Glc | Gic | Gln |
| | Prod | Glu | Prod | NH3 | Ala | Glc | Prod | Prod | Lac | Gly | Glc | Asn |
| | Glu | Prod | Asp | Prod | NH3 | Ala | Gly | Gly | Ala | Glu | Glu | Gly |
| | Gly | Ser | Gln | Ser | Bio | Prod | Lac | Ala | Asn | Ala | Asp | Bio |
| | LDH | Gly | Gly | Lac | Ser | Asn | NH3 | Asn | Bio | Prod | Prod | Gly |
| | Glc | Gly | LDH | Glc | Gly | Bio | LDH | Bio | NH3 | LDH | Ala | Ala |
| | Glc | LDH | Glc | LDH | Glc | Asp | Glc | Glc | LDH | Lac | Lac | Lac |
| | LDH | Glc | LDH | Glc | LDH | NH3 | NH3 | Lac | Glc | Lac | Lac | Lac |
| H | 8 | 4 | 6 | 8 | 1 | 2 | 6 | 4 | 2 | 3 | 1 | 4 |
| Iterationen | 916 | 1000 | 1000 | 299 | 1000 | 999 | 770 | 761 | 169 | 764 | 1000 | 500 |

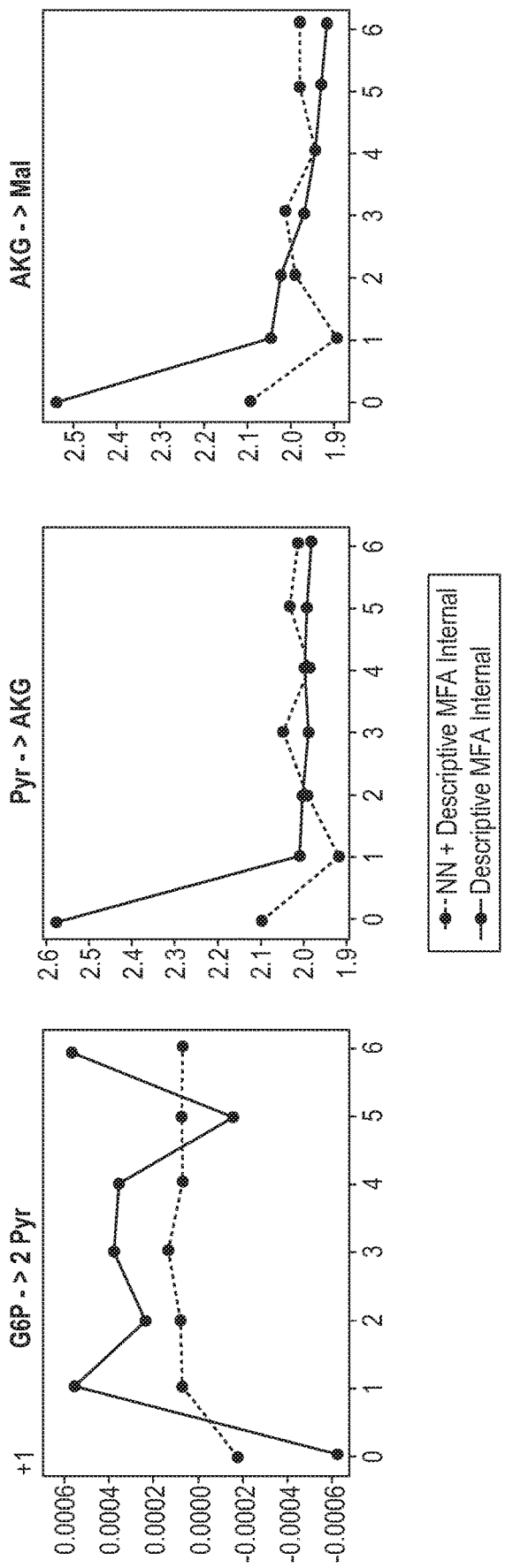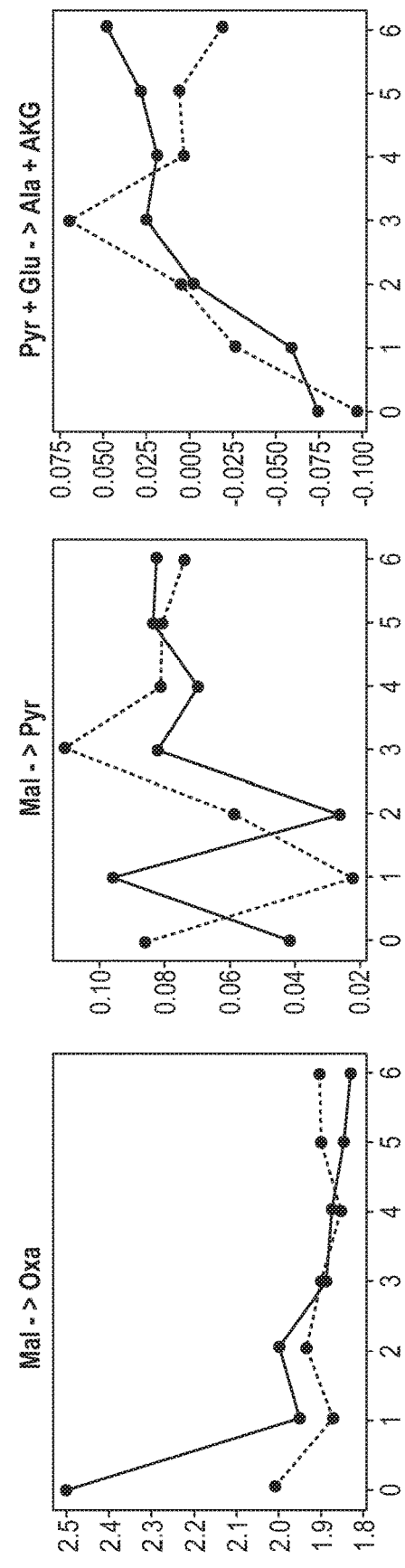
Fig. 21A

PREDICTING THE METABOLIC CONDITION OF A CELL CULTURE

CROSS-REFERENCE TO RELATED APPLICATIONS

This application is a continuation of PCT International Application No. PCT/EP2019/050006 which has an International filing date of Jan. 2, 2019, which claims priority to European Patent Application No. 17211217.9, filed Dec. 29, 2017, the entire contents of each of which are hereby incorporated by reference.

DESCRIPTION

Field of Invention

The invention relates to the prediction of the metabolic state of cells, in particular of cells maintained in cell culture.

Background and Related Art

In recent years, the pharmaceutical industry has seen a significant increase in efforts to make processes in development, production and quality assurance more efficient by placing a stronger focus on means of process analysis, monitoring and control. This tendency affects also and to a special extent the operation of cell culture reactors, which are used to produce pharmaceutically relevant molecules, especially macromolecules such as proteins.

The modelling of cell metabolism and fermentation processes in the context of pharmaceutical research and development, however, turns out to be a major technical challenge: The metabolism of cells, in particular of eukaryotic cells, is characterized by very complex non-linear chemical reaction cascades which are difficult to analytically simulate or model.

For example, the analysis of metabolic fluxes using metabolic flux analysis (MFA) is well known. MFA is particularly used for processes in which the intracellular flux distribution is time-invariant. This is approximately given for the exponential growth phase in batch bioreactors or for cultivation in chemostats. However, in the fed-batch processes predominantly used today, the cells are exposed to constantly changing environmental conditions. Therefore, the intracellular fluxes vary during the processes. Therefore, it is not sufficient to perform a single metabolic flow analysis to map the state of the cells throughout the entire process. In addition, it is unfavorable with regard to process control if it is only descriptively determined that the cells of a bioreactor have already entered a metabolically unfavorable state. It would be better to predict this and, if necessary, take countermeasures at an early stage. The use of MFA for the analysis of metabolic fluxes is described in Ahn W S, Antoniewics M R (2012): "*Towards dynamic metabolic flux analysis in CHO cell cultures*", Biotechnology Journal 7, 61-74.

However, the attempt to predict the state of the cells in a cell culture at a future point in time is also very difficult for several reasons. Kinetic models are usually used to predict the course of time. These consist of a system of differential equations which describe the changes over time of substance concentrations or of substance quantities. The equations are usually based on mechanistic knowledge, which can be modelled, for example, using Michaelis-Menten kinetics. However, this kinetic knowledge is difficult to obtain. For the description of an entire intracellular metabolic network using kinetic expressions, the available mechanistic information is usually not sufficient and the number of parameters to be estimated would be enormous.

However, kinetic hybrid models that combine metabolic flux analysis with kinetic knowledge were in practice mostly not able to generate reliable predictions of the future behaviour of a cell culture. The generation of these models has proven to be extremely labor-intensive. Moreover, the models generated in this way are not very flexible and cannot be adapted to the metabolism of other cell types without considerable manual effort. The use of hybrid models is described for example inCovert M W, Xiao N, Chen T J, Karr J R (2008), "*Integrating metabolic, transcriptional regulatory and signal transduction models in Escherichia coli*", Bioinformatics Vol. 24 no. 18, 2044, and in Nolan R P, Lee K (2011) "*Dynamic model of CHO cell metabolism*", Metabolic Engineering 13, 108.

SUMMARY

In this context, there is a need for improved methods for predicting the metabolic state of cells and for correspondingly improved systems to the extent that the above-mentioned disadvantages are at least partially avoided.

The subject matter of the invention is stated in the independent claims. The embodiments of the invention are described in the dependent claims. The embodiments and examples of the invention described here may be freely combined with each other, provided they are not mutually exclusive.

In one aspect, the invention relates to a method for predicting the metabolic state of a cell culture of cells of a specific cell type. The method comprises providing a metabolic model of a cell of the specific cell type, wherein the metabolic model includes a plurality of intracellular and extracellular metabolites and a plurality of intracellular and extracellular fluxes, and wherein the metabolic model comprises stoichiometric equations specifying at least one stoichiometric relationship between one of the intracellular and one of the extracellular metabolites.

The method further comprises performing the following steps at each of a number of points in time during the cultivation of the cell culture:
 receiving a plurality of measurement values measured at that point in time, the measurement values comprising concentrations of a plurality of extracellular metabolites of the metabolic model in the culture medium of the cell culture and a measured cell density of the cells in the cell culture;
 inputting the received measured values as input parameter values into a trained machine learning program logic (MLP);
 predicting extracellular fluxes of the extracellular metabolites at a future point in time by the MLP using the received measurement values, the future point in time being a point in time subsequent to the point in time of receiving the measurement values, wherein the extracellular fluxes are uptake rates of the extracellular metabolites into a cell and/or release rates of the extracellular metabolites from a cell into the medium;
 performing metabolic flux analysis to calculate the intracellular fluxes at the future point in time using the predicted extracellular fluxes of the extracellular metabolites and the stoichiometric equations of the metabolic model.

This may be advantageous because in this way the knowledge, which for example in the form of stoichiometric reaction equations is already available in the literature for many important metabolic processes of cells, and which can be represented in the form of metabolic models, can be combined in a very advantageous way with the use of an MLP, which allows a high degree of flexibility. Some preliminary experimental studies have shown that the use of MLP-based approaches, for example the use of neural networks to predict future metabolic states of cells purely based on, for example, the concentration of their excretion products, is unreliable. The complexity and dynamics of cellular metabolism seem to make it impossible even for sophisticated, modern MLP methods to provide a reliable prediction of the metabolic state of a cell culture in the future purely based on current cell concentrations, especially in fed-batch bioreactors with eukaryotic cells. On the one hand, this might be due to the fact that the internal cell state is only very indirectly and insufficiently characterized by the measurement of extracellular metabolite concentrations. On the other hand, there is also the risk of "over-fitting" to the training data in the course of generating the MLP in the training phase. However, it has been shown that MLP-based methods, as described here for training forms, may provide very reliable predictions regarding the concentration and fluxes of extracellular metabolites at least for a point in time not too far in the future. By combining this knowledge with the knowledge of stoichiometric and transport dependencies between intracellular and extracellular metabolites and between each other, embodiments of the invention enables to accurately predict the metabolic state of the cells down to the level of individual intracellular fluxes.

Although a coarse characterization of the metabolic state of cells based on the substances excreted by them (such as lactate) has been possible up to now, the internal processes of the cell ultimately remained a "black box". A finegranular prediction of cell metabolism down to the level of individual cell-internal material fluxes was not possible with the currently known hybrid models.

In another advantageous aspect of the invention, a highly flexible method for predicting cell metabolism is provided. It has been shown that even by culturing a few cell cultures with the cells of a specific cell type, a sufficiently large training data set may be obtained to train an MLP which is capable of making reliable predictions regarding the metabolic state at a future point in time for cell cultures of that cell type. The acquisition of the training data and the subsequent training of the MLP may be largely automated. In contrast, the metabolic model used for metabolic flux analysis, which may require extensive literature study and manual adaptation steps, may often be reused for cells of different cell types. Thus, in contrast to the use of hybrid models known in the state of the art, it is often possible to provide a prediction method that takes into account specific metabolic characteristics of a specific cell type without the need for the complex creation of new models, simply by cultivating a few cell cultures to generate a training data set and then training an MLP on this training data set.

In another advantageous aspect, MFA is now successfully used to predict intracellular fluxes. Up to now, MFA has mainly been used for processes where the intracellular flux distribution is time-invariant. This is approximately given for the exponential phase in batch processes or for cultivation in chemostats. However, in the fed-batch processes and perfusion-like processes with cell retention that are predominantly used today, the cells are exposed to environmental conditions that are constantly changing. Therefore, the intracellular fluxes also vary during the process. Approaches that have tried to map the state of the cells throughout the entire process have failed. In contrast, an approach was found to accurately predict the metabolic state of fed-batch reactors at least for the coming hours and days by defining a dynamic metabolic model that describes the intracellular fluxes as a function of the (possibly discretized) process time.

In a further advantageous aspect, embodiments of the method according to the invention make it possible to control the quality of the prediction or the intermediate results obtained during this prediction during the cultivation of the cell culture. The method described above includes the prediction of extracellular fluxes. These can be easily determined from the change in concentration of extracellular metabolites during fermentation by repeated sampling and analysis of samples of the culture medium. Thus, the prediction of MLP may be checked during fermentation by repeatedly comparing the predicted and measured extracellular fluxes. If significant differences occur, the calculation may be stopped immediately and the causes of the deviation investigated. Other state-of-the-art metabolic flux prediction methods use 13C measurement data in the steady state to predict intracellular and extracellular material fluxes. These methods therefore require 13C-labelled analyses and experiments under steady-state conditions to directly predict intra- and extracellular fluxes. 13C analyses are complex and during operation of a fermenter, stationary conditions may not be assumed. In addition, the predicted intracellular fluxes cannot be empirically verified, so there is no intermediate step in such procedures that may be compared with real measured data.

According to the embodiments of the invention, the MLP receives input data in the form of extracellular concentrations of extracellular metabolites at a current point in time to predict the corresponding extracellular fluxes at a future point in time (next sampling time) under dynamic fermentation conditions. The intercellular MFA is calculated based on the stoichiometric metabolism model (for the future and optionally also the current sampling time). This allows to verify the prediction during fermentation by measured extracellular metabolite concentrations.

Embodiments of the invention thus provide a method for predicting the metabolic state of cell cultures which is both accurate (since it provides detailed information about intracellular metabolic processes and it has been shown experimentally that the predictions regarding extracellular fluxes correspond very well to the actually measured extracellular fluxes) and which is very flexible since it may be easily adapted to cells of another cell type.

According to embodiments, at least some of the extracellular and intracellular fluxes of the metabolic model are not based on a decomposition of a known metabolic network into elementary flux modes. In the literature, simple intracellular network fluxes have already been estimated using MLPs. First, the elementary flux modes of the network were generated. Elementary flux modes represent a set of permissible flux distributions from which all other possible flux distributions may be combined by different weightings. The MLP outputs the corresponding weightings. However, the number of these elementary flux modes is so large for most biochemical networks that an effective and robust estimation of the weightings is not possible.

However, according to the invention, only the extracellular fluxes via neural networks or other MLPs are estimated. The coupling to metabolic material flux analysis then established the link to intracellular flux distribution.

According to the embodiments of the invention, the machine learning program logic is thus designed to selectively predict only extracellular fluxes, but not intracellular fluxes.

This may be advantageous because the prediction is thus limited to values that can easily be measured even during operation of a bioreactor, so that the extracellular fluxes represent intermediate values for the prediction of intracellular fluxes, which can easily be compared with real measured data to quickly identify errors in the MLP.

In another aspect, the method may be advantageous for the following reasons: The metabolism of the cells depends largely on the conditions in the bioreactor. If factors such as pH value, pO2 value, pressure and temperature are kept constant, the metabolite concentrations in the reaction medium are particularly important for the behavior of the cells, which is why these were chosen as inputs for the MLP. The prediction of future metabolite fluxes has two major advantages over the prediction of future metabolite concentrations at the next sampling time:

On the one hand, the MLP trained in this way is more flexible with regard to the choice of time intervals. If networks with metabolite concentrations are trained as outputs, the prediction that may be made with such a trained MLP always refers to the same time interval as in the training data set. Already when generating the training data, it should therefore be ensured that the intervals are chosen as uniformly as possible, as otherwise inconsistencies may arise. If, on the other hand, flows are predicted, this results in a certain independence of the time interval for the current prediction from the time intervals used during MLP training. The method is therefore more robust and flexible with regard to the choice of time intervals for the prediction.

On the other hand, the metabolite concentration depends on continuous and/or pulse-like nutrient dosages, which may be handled variably in some cases. However, this variability does not exist in the prediction if the trained MLP does not treat the added doses, which were carried out in the training data set, separately but learns blindly. By using the extracellular metabolite fluxes, the future concentrations may be extrapolated using equation 4.4 of the appendix. There is some flexibility with regard to the time interval, provided that the fluxes are not subject to strong fluctuations in relation to the sampling intervals. According to preferred embodiments, the time interval between points in time used for the prediction of extracellular fluxes is less than or equal to, or at most 20% greater than, the time intervals used for the preparation of the training data set.

According to embodiments, the calculated extracellular fluxes are calculated so that they are adjusted for substance additions (e.g. glucose additions). Thus, when predicting the one or more extracellular fluxes, the information that a specific extracellular metabolite will be added in the next time interval may be used to adjust the prediction of the concentrations of this extracellular metabolite accordingly. It is also possible to adjust the feeding appropriately based on the prediction, if the MLP predicts that a deficiency of this extracellular metabolite is to be expected. It should be noted, however, that added doses may generally influence the mean flux, as this results in altered concentrations in the reactor. If the dosage profile deviates significantly from the training data, inaccuracies may result.

According to embodiments of the invention, the temporal and quantitative profile of the feeds of metabolites to a cell culture whose metabolic state is to be predicted is chosen to be identical or similar to the feed profile used to generate the training data with one or more training bioreactors, the MLP having been trained on these training data.

According to embodiments of the invention, the measurements for the acquisition of the measured data as well as the prediction of the extracellular fluxes are carried out in real time, i.e. during the operation of the bioreactor containing the cell culture. The time between the collection of the measurement data and the prediction of the metabolic state of the cells is typically small and in the range of a few seconds or minutes, typically less than 15 minutes, whereas the time intervals for individual predictions are typically in the range of 1-48 hours and in particular 6-24 hours.

In a further advantageous aspect, embodiments of the invention thus enable the prediction of the metabolic state of a cell culture in real time, since the information base on which the prediction is based consists of the already defined metabolic model, the already existing trained MLP and measurement data, which may be easily collected in real time. For example, by regularly taking a sample from the culture medium and determining the cell count and metabolite concentration in this sample, the measurement data required to perform the prediction may be obtained.

According to embodiments of the invention, the method for predicting the metabolic state of a cell culture is carried out at a future point in time in real time continuously during the operation of a bioreactor containing the cell culture.

According to embodiments, the method further comprises MLP generation by machine learning.

The generation of the MLP comprises generating a training data set, wherein the generation of the training data set comprises performing the following operations at each of a plurality of training points in time during the cultivation of at least one training cell culture of cells of the specific cell type:

receiving a plurality of measurement values measured at said training point in time, said measurement values comprising concentrations of a plurality of extracellular metabolites of the metabolic model in the culture medium of said at least one training cell culture and a measured cell density of the cells in said at least one training cell culture;

receiving the time indication of the current training point in time; and calculating extracellular fluxes of the extracellular metabolites as a function of the measured values received at that point in time and the measured values received at the respective preceding point in time, wherein the extracellular fluxes are uptake rates of the extracellular metabolites into the cell and/or release rates of the extracellular metabolites into the medium;

training the MLP, wherein the training comprises:

inputting the measured values received at each of the training points in time as input parameter values to the MLP, and inputting the extracellular fluxes calculated for that following point in time at each point in time following that training point in time as output parameter values associated with those input parameter values to the MLP; and performing a learning process by the MLP in such a way that the MLP learns to predict the respective associated output parameter values based on the input parameter values;

storing the trained MLP in a volatile or non-volatile storage medium.

The use and generation of an MLP according to embodiments of the invention may be advantageous, since on the one hand a high accuracy of the prediction can be achieved when choosing suitable machine learning algorithms, and on the other hand an adaptation to the metabolic conditions in other cell types can be carried out very easily and without major manual effort or literature study. The operation of some training cell cultures with continuous collection and recording of the above-mentioned measurement data and the extracellular fluxes calculated from them is sufficient to provide a training data set on the basis of which an MLP may be trained and generated specifically for the cell type of the cells used in the training cell cultures.

According to embodiments of the invention, the training data set is generated such that at each of a plurality of training points in time during the cultivation of multiple training cell cultures of cells of the specific cell type, the measured values and time specifications are received and the extracellular fluxes of the extracellular metabolites are calculated. For this purpose the cell cultures are preferably cultivated in bioreactors of different types. Preferably, these bioreactor types comprise at least two different types of bioreactors from the following set: a fed-batch bioreactor, a batch bioreactor, a perfusion reactor (including variants with cell retention), a chemostat and a split-batch bioreactor.

The use of bioreactors of different types in the generation of the training data set may be advantageous, as a broader data basis is generated and an "overfitting" of the MLP in the course of training can be avoided or reduced. In addition, it enables the use of the same MLP for the successful prediction of the future metabolic state of a cell culture in many different types of bioreactors. Preferably, the training data set is collected based on training cell cultures cultivated in different bioreactor types, whereby the bioreactor types include at least one fed-batch bioreactor and/or at least one perfusion reactor. This may be advantageous, since these reactor types are being used more and more frequently in practice and the representation of the metabolic state of cell cultures in these reactor types has so far been particularly difficult due to their great dynamics.

Preferably, the cell culture whose future metabolic state is to be predicted is cultivated in a type of bioreactor that was also used to generate the training data sets.

According to embodiments, the training data set is generated in such a way that at each of a plurality of training points in time during the cultivation of several training cell cultures of cells of the specific cell type, the measured values and time specifications are received and the extracellular fluxes of the extracellular metabolites are calculated, the cell cultures being cultivated in bioreactors of the same type or of different types, all bioreactors not belonging to the batch bioreactor type. For example, all bioreactors may be of the fed-batch type.

Due to the continuous or pulsed addition of additional culture medium during operation, the prediction of future metabolic states of cells in fed-batch bioreactors has proven to be a very technical challenge. Embodiments of the invention are particularly advantageous in the context of the use of fed-batch bioreactors, since it has been shown that predictions according to embodiments of the invention are accurate despite the metabolic complexity of cell cultures cultivated in this type of reactor.

According to some embodiments the MLP is a support vector machine or a system of several support vector machines.

According to other embodiments, the MLP is a neural network or a system of several neural networks (NNs).

Some initial tests suggest that other MLP methods may be used in addition to support vector machines and neural networks. However, particularly good prediction results have been achieved when using neural networks and a wide range of software solutions for different network architectures is already available that allow easy handling of the neural network during the training phase as well as during the application phase.

According to embodiments of the invention, the MLP is a system of several sub-MLPs (in particular individual NNs), wherein the individual sub-MLPs contained in the system have each been trained to predict the extracellular flux of a single extracellular metabolite and are selectively used to predict the extracellular flux of that single extracellular metabolite at the future point in time.

This may be advantageous, as it has been shown that the predictive power of measured concentrations of extracellular metabolites is different with respect to individual extracellular fluxes of other extracellular metabolites. The quality of the prediction may be improved by training individual sub-MLPs, for example individual neural networks, each based on a specific set of input parameter values with respect to the extracellular flux of the extracellular metabolite as an output parameter value. The results of the individual sub-MLPs may be linked by a higher-level MLP or other program logic so that an extracellular flow of one or more extracellular metabolites is returned as an overall result. A "sub-MLP" is an MLP that is functionally linked to one or more further "sub-MLPs" in such a way that the output of this and the further "sub-MLPs" is combined, e.g. aggregated, by a higher-level program logic, in particular by a further, higher-level MLP, to form an overall result.

According to embodiments of the invention, the MLP uses measured concentrations of several extracellular metabolites as input parameter values to predict the extracellular flux of a single one of the extracellular metabolites. In this respect, the multiple extracellular metabolites used as input parameter values for at least two of the extracellular metabolites whose extracellular flux is to be determined are different.

This may be advantageous, as it may lead to a higher accuracy of the prediction.

According to embodiments of the invention, the method further comprises a measurement of the concentrations of all input candidate metabolites over several points in time. In particular, the measurement may serve to establish metabolic concentration profiles over time. The set of input candidate metabolites comprises all extracellular metabolites which are metrologically available in a reference bioreactor with a cell culture of the specific type or all extracellular metabolites of the metabolic model. For example, the reference reactor may be one or more training bioreactors, i.e. reactors that were used to collect the training data for the generation of MLP. Alternatively, the reference reactor may also be another reactor with a cell culture of the same type as the bioreactor currently being monitored. The determination of those extracellular metabolites that are to serve as input parameter values for the MLP with regard to the prediction of the extracellular fluxes of individual extracellular metabolites of the model is therefore preferably done during or before the training of the MLP.

For each of the extracellular metabolites whose extracellular flux is to be predicted, a selection procedure is performed to identify the multiple extracellular metabolites to be used as input parameter values to predict the extracellular flux of that single metabolite. The selection procedure comprises with respect to this single metabolite in each case:
  (a) defining a first set of extracellular metabolites, the first set comprising all candidate input metabolites;

(b) calculating a first relevance score of each of the extracellular metabolites in the first set as a function of the measured concentrations of that metabolite, the first relevance score indicating the predictive power of the concentration of the respective extracellular metabolite with respect to the extracellular flux of that single extracellular metabolite;

(c) transferring only that one of the extracellular metabolites having the highest first relevance score from the first set to a still empty second set of extracellular metabolites, removing this metabolite from the first set;

d) calculating a further relevance score of each of the extracellular metabolites in the first set as a function of the measured concentrations of that metabolite and the measured concentrations of all extracellular metabolites contained in the second set, the further relevance score indicating the predictive power of the concentration of the respective candidate input metabolite with respect to the extracellular flux of that single extracellular metabolite taking into account the metabolites already contained in the second set;

(e) transferring only that one of the extracellular metabolites of the first set which has the highest further relevance score to the second set, removing this metabolite from the first set, the transfer taking place only if, by the inclusion of this metabolite, the second set does not exceed a maximum limit for informative redundancy of the metabolites contained therein with respect to the prediction of the extracellular flux of this single extracellular metabolite;

(f) repeating steps d) and e) until no more metabolites can be transferred from the first to the second set without the second set exceeding the maximum informative redundancy limit; and (g) using selectively only the metabolites transferred to the second set as input parameter values to predict the extracellular flux of that single extracellular metabolite.

According to embodiments, the first relevance score is calculated as a partial mutual information score—PMI score—between a metabolite of the first set and the single metabolite whose extracellular flow is to be predicted. The second relevance score is calculated as a PMI score—between a metabolite of the first set and the single metabolite whose extracellular flow is to be predicted, taking into account all metabolites already contained in the second set.

This may be advantageous, as it may allow the determination and use of input parameter values that have particularly high predictive power for the respective extracellular metabolite or its flux. Overfitting in the course of training and thus poor prediction quality may be avoided.

By identifying those metabolites that have the highest significance ("relevance" or "predictive relevance") for a specific extracellular flux of an extracellular metabolite, it is ensured that the selected input parameter values enable the generation of an MLP with good predictive power. Predictive relevance is preferably determined by determining the degree of correlation of a measured metabolite concentration profile of a specific extracellular metabolite with the metabolite concentration profile of the metabolite whose extracellular flux serves as the output parameter value of the MLP (i.e. whose extracellular flux is to be predicted). Predictive relevance may be determined by various methods, e.g. principal component analysis or PMI ("partial mutual information") as described below for embodiments of the invention. The fact that a metabolite is only included in the second set if the second set does not already contain a metabolite whose concentration profile strongly correlates with the concentration profile of this metabolite (which implies a high degree of informative redundancy of this metabolite with this metabolite already contained in the second set) protects against the fact that the second set also contains groups of two or more metabolites whose concentration profiles strongly correlate and would thus introduce redundant information into the second set. A high proportion of information-redundant metabolites in the second set would lead to overfitting effects.

For example, for the inclusion of further metabolites from the first to the second set, the reaching of a maximum value for informative redundancy or another termination criterion may be defined, so that normally only a part of the metabolites is transferred from the first to the second set.

Thus, according to embodiments of the invention, the selection of the input parameters (extracellular metabolites, whose concentration is measured and entered into the MLP) may be completely independent of the MLP.

However, it is also possible that the selection procedure is carried out in the form of a "wrapper" as described in chapter 4.7.3 of the appendix, e.g. as a functionality provided by the neural network.

According to embodiments, the first relevance score of each of the metabolites in the first set with respect to this single extracellular metabolite is calculated as PMI score between this metabolite and the single metabolites whose extracellular flux is to be predicted in each case.

A PMI score (in contrast to the simpler Mutual Information (MI)) may also be used in the further, iteratively executed steps to calculate the further relevance score of each metabolite remaining in the first set. The further PMI score indicates the predictive relevance of this metabolite with respect to the extracellular metabolite, whereby this relevance includes the informative redundancy of the metabolite to be tested from the first set with respect to all metabolites already included in the second set. Thus, before a metabolite is finally included in the second set, it is checked whether it has any "predictive added value" over and above the metabolites already contained in the second set in view of the metabolites already in the second set. If the measured concentration profile of this metabolite correlates strongly with a metabolite already present in the second set, this is negated. In this case, there will be no inclusion in the second set.

A test data set may be used to estimate the quality of the selection of input parameters and to optimize the architecture of the MLP (e.g. number of layers of a neural network).

The determination of the predictive relevance of a metabolite with respect to an output parameter metabolite by means of the PMI thus allows a measurement or estimation of the possible input variable and the dependency between each of the possible input variables with respect to the output variable. The stronger the dependency, the better the output variable may be predicted on the basis of the input variables, the higher the relevance score of the input value metabolite. This enables the calculation of the relevance score and score-based sorting of the metabolites of the first set.

In the PMI-based decision whether a metabolite is included in the second set, the PMI is used to determine the dependence of this metabolite on each metabolite already in the second set. Only those metabolites are included in the second set that contain enough relevant new information compared to the metabolites already in the second set to avoid redundancies.

Thus, when selecting the next relevant metabolite in the second set, the metabolites already selected in the second set are also taken into account.

The calculation of the dependency between extracellular metabolites in the form of PMI ("partial mutual information") may, for example, be carried out in order, in the course of the decision whether a metabolite of the first quantity should be included in the second quantity, to compare the calculated PMI with a PMI criterion, e.g. a PMI limit value for a still acceptable degree of dependence; however, the comparison with a PMI criterion usually does not consist of a simple comparison with a limit value, but consists of a statistical test or an alternative selection procedure such as a "wrapper", as explained in the appendix, for example, according to equations 2.22-2.27 and in chapter 4.7.3 of the appendix. According to the embodiment described in the Appendix, the "most relevant", i.e. the one with the highest PMI value, is always taken over into the first set. In this way an order of all metabolites is generated. Finally, however, ALL metabolites are in the first set. In a subsequent step (wrapper), it is then decided how many of the most relevant metabolites will be included in the "second list" of those used for prediction.

According to embodiments, the MLP uses measured concentrations of several extracellular metabolites as input parameter values to predict the extracellular flux of each of the extracellular metabolites, wherein the several extracellular metabolites comprise at least one, preferably at least two amino acids. The metabolites whose concentrations are used as input parameter values often, but not necessarily, contain the metabolite whose flux is used as the output parameter value.

The use of amino acid concentrations in the medium as input parameter values for the MLP or for the training of the MLP may be advantageous, since established methods for determining their concentration already exist and the sufficient presence of amino acids is often necessary for the efficient synthesis of many target proteins in a bioreactor.

It is possible that already during the training only the concentrations of this subset of metabolites are selectively used to train the MLP.

If one sorts the input parameter values of the first set according to their relevance (e.g. according to PMI), then in the end all available inputs are contained in this "set", but in the order that indicates relevance. An additional criterion is then used to determine from this list the number of input parameters (concentrations) that are to be used as inputs in the future. According to embodiments of the invention, the selection was made during the training itself (different numbers of input parameters were compared in terms of their predictive power, which was evaluated using a test data set).

Preferably, only the concentrations of this subset of metabolites measured in the cell culture, whose metabolic status is to be predicted, are selectively used as input parameter values for the already trained MLP. The selective use of predictively relevant and independent input variables (instead of all metabolically available concentrations of extracellular metabolites) may be advantageous as it reduces the problem of "overfitting", simplifies data collection (it may not be necessary to measure all extracellular metabolite concentrations of the model), and reduces the need for computer resources for prediction as fewer input parameter values need to be evaluated.

According to embodiments, the metabolic model for the intracellular metabolites of the model represents a steady state assumption that the amount of intracellular metabolites remains constant so that the sum of the incoming fluxes for each intracellular metabolite is equal to the sum of the outgoing fluxes of that metabolite.

According to embodiments, the plurality of points in time (used to predict the extracellular fluxes of the currently cultured cell culture) are separated by time intervals of 10 minutes to 48 hours, preferably 1-24 hours. According to preferred embodiments, the time interval between the points in time used for predicting extracellular fluxes is less than or equal to, or at most 20% greater than, the time intervals used in the preparation of the training data set.

According to embodiments, the plurality of points in time are separated by time intervals which are of equal length over the duration of the cell culture performance or whose length decreases towards the end of the cell culture performance. By preferred embodiments, the profile of the change in time intervals between points in time used to predict extracellular fluxes is identical or very similar to the profiles of the changes in time intervals used in the preparation of the training data set.

The specific cell type may be prokaryotic or eukaryotic.

In particular, the specific cell type may be a eukaryotic cell type.

It has been shown that despite the high complexity of eukaryotic metabolic processes, embodiments of the invention are capable of accurately predicting the metabolic state of the cell, especially for future time periods ranging from hours to 1-2 days in the future.

For example, the specific cell type may be a mammalian cell type, e.g. HELA cells and others.

According to one embodiment, the specific cell type is Chinese Hamster Ovary (CHO) cells.

According to embodiments, the specific cell type is a genetically modified cell type which is maintained and/or multiplied in a bioreactor for the purpose of obtaining a biomolecule. For example, it may be a genetically modified cell line that expresses a specific protein, e.g. an enzyme or a specific antibody, and/or expresses it in particularly high quantities.

After embodiments have been determined, the calculated intracellular fluxes are evaluated for plausibility and consistency and/or with regard to further quality criteria and, if necessary, modified by adding, removing or changing stoichiometric equations. The measured and/or predicted extracellular metabolite fluxes are then transferred to the modified metabolic model and the intracellular fluxes are recalculated and re-evaluated for plausibility and/or consistency. Thus the quality of the metabolic model may be improved and, if necessary, adapted to specific cell types or cell clones. Using these plausibility criteria, plausible reference values for the intracellular fluxes may also be obtained according to embodiments of the invention on the basis of several experimental tests.

According to embodiments, the calculation of the intracellular flux of one or more intracellular metabolites at each of the future points in time involves a calculation of several or preferably all intracellular fluxes of the metabolic model. Preferably, all intracellular fluxes of the model are calculated. The more intracellular fluxes are considered, e.g. in a plausibility estimate, the higher the reliability of the prediction.

According to embodiments, the method comprises an identification of all intracellular fluxes that deviate from a respective reference value or reference value range by more than the limit value. The reference values or reference value ranges may, for example, be obtained empirically and/or derived from the literature. The method further comprises an automatic identification of that intracellular flux which acts as a limiting factor for cell growth or the production of a desired biomolecule.

For many metabolites their approximate intracellular flux is known in the context of a specific metabolic state, e.g. by kinetic models, by 13C-labelled substrates and quantification via NMR of isotopomers of the metabolites or by the amino acid composition of the cell proteins etc. Strong deviations from these reference ranges thus indicate that the metabolism of the cells in the cell culture is in an unfavorable or at least unexpected state. The fact that embodiments of the invention compare intracellular fluxes with reference values and not, for example, the concentration of extracellular metabolites with reference values in order to draw conclusions about the metabolic state of a cell via these reference values, is advantageous, since this may allow a more fine-grained and better determination of (mostly undesired) deviations of the physiological state of a cell from physiologically usual or favorable reference values.

In a further aspect, the invention relates to a method for monitoring and/or controlling a bioreactor which includes the cell culture of cells of a specific cell type.

The method comprises a calculation of intracellular fluxes at a future point in time according to the embodiments and examples of the method for predicting the metabolic state of cells described herein. The method further comprises a comparison of the predicted intracellular fluxes with reference values or reference value ranges for acceptable intracellular fluxes of the respective one or more intracellular metabolites.

The method may be used to monitor the bioreactor and may include the issuing of a warning, the warning being issued if a deviation of the calculated intracellular flux from its respective reference value or reference value range exceeds a limit value.

The warning may, for example, be sent via a graphical user interface to a human and/or via another interface to machines or software programs that log the deviations.

In addition or alternatively, the method may be used to control the bioreactor and may involve sending a control command to the bioreactor. The control command is sent to automatically initiate steps to change the condition of the bioreactor or the medium it contains to reduce the deviation. For example, the control command may go to a valve, pump or other actuator in the reactor and cause the addition of culture media, trace elements, oxygen, CO2, pH-regulating acids or bases or a corresponding throttling of the addition. In particular, the automatic steps may involve a change in the quantity or composition of a culture medium. The control command may therefore be given to a mixer of a culture medium or a throttling unit at a feed line of the culture medium, for example, to change the amount of specific sugars, salts and/or amino acids in the culture medium or to reduce or increase the feed rate of the culture medium into the bioreactor, depending on the predicted fluxes.

For example, according to the embodiments of the method, it may be determined or predicted that a specific intracellular metabolic pathway is significantly weaker (indicated by low intracellular flux) than expected or desired. It may be known that this metabolic pathway is often limited by the amount of a specific vitamin or trace element in the medium, e.g. iron. Therefore, if it is detected that this specific intracellular flux is lower than expected, the targeted addition of iron to the bioreactor may be counteracted much more specifically than is possible if care is taken only to keep physical or extracellular parameters such as temperature, pH, glucose concentration etc. constant.

According to embodiments, the method for monitoring and/or controlling a bioreactor involves identifying the reaction within the metabolic model of the cells that acts as a limiting factor for cell growth or the production of a desired biomolecule according to the embodiments and examples of the method for predicting the metabolic state and several intracellular fluxes of cells described here. The method further comprises an automatic addition of selectively those substances (especially enzymes, co-enzymes, trace elements or nutrients) which (exclusively or especially) alter the intracellular flux acting as a limiting factor in such a way that cell growth or the production of the biomolecule or the quality of the biomolecule is promoted. In addition or alternatively, the method comprises an output of a request for such addition via a user interface.

This may be advantageous as it allows more detailed monitoring or the adoption of very specific control measures to control a bioreactor than is possible with methods known in the state of the art which are based on trying to keep only the operating parameters of the bioreactor constant, including some parameters measured in the medium. For example, a high uptake and metabolism of amino acids does not necessarily mean that the cell also utilizes the amino acids for the synthesis of the desired target protein. Depending on the state of the intracellular fluxes of the cell, it may also be that the absorbed amino acids are metabolized for completely different purposes. However, according to the invention, this may be achieved by metabolic flux analysis based on a specific metabolic model of the cell using the predictions of the MLP.

After embodiments of the method, the predicted extracellular and intracellular fluxes are also used to test the quality of the model. For example, if a model formulated for a specific CHO cell clone differs significantly from another clone or from another cell line (other tissue or animal species), the predicted fluxes (intracellular by MFA, extracellular by MLP) may be compared with measured rates of concentration change or plausibility criteria (no unrealistic or unphysiologically high fluxes, etc.). In case of high deviations of the predicted from the measured or plausible fluxes, the model is adjusted or regarded as an indication for the presence of an error in the metabolic model on the basis of which the model is corrected.

By comparing the predicted fluxes with the measured or plausible fluxes, measurement errors in the determination of concentrations of extracellular metabolites or biomass are identified according to embodiments, e.g. by means of statistical tests.

In a further aspect, the invention relates to a method for identifying a metabolically advantageous clone of cells of a specific cell type. The method comprises:
  culturing of different cell cultures in several bioreactors, whereby the different cell cultures contain different clones of cells of the specific cell type;
  calculating the intracellular flux of one or more intracellular metabolites at several points in time separately for each of the cell clones according to the embodiments and examples of the method for predicting the metabolic state of cells described herein;
  identifying that one of the cell clones whose calculated intracellular flux of the one or more intracellular metabolites is metabolically most favorable.

This may be advantageous, since in the context of pharmaceutical synthesis processes it is often necessary to identify and selectively propagate metabolically advantageous cell clones. Many known methods for the genetic modification of cells do not provide complete control over whether and at which position in the genome of a cell a specific gene encoding a target protein to be synthesized is inserted.

Depending on its position in the genome, the expression rate may vary. For example, the transfection of cells with viruses is a method in which many different cell clones are created, some of which do not contain the desired gene at all and others which have the desired gene inserted but at different positions in the genome. According to the invention, the parallel operation of several bioreactors with the different cell clones in real time may now reveal whether the intracellular fluxes indicate that the gene encoding the target protein has been incorporated into the genome of the cell and that the target protein is synthesised in the cell to a considerable extent. For example, a comparison of the amino acid composition of the target protein with the intracellular fluxes for the synthesis or degradation of individual amino acids may give an indication as to whether the target protein has been incorporated. In addition or alternatively, the intracellular fluxes may provide information as to whether a specific cell clone reproduces sufficiently fast and is vital, whether it has a low formation rate of toxic or otherwise undesirable metabolites, etc.

However, embodiments of the method according to the invention may not only be used to predict the future metabolic state of cells, but also to describe the current metabolic state of a cell.

According to embodiments, the method comprises:
calculating the current extracellular flux of one or more of the extracellular metabolites from the concentrations of the extracellular metabolites measured at the current point in time and at the previous point in time;
performing a further metabolic flux analysis to calculate the current intracellular fluxes at the current point in time using the calculated current extracellular fluxes of the extracellular metabolites and the stoichiometric equations of the metabolic model; and
using the calculated current intracellular fluxes as a description of a current metabolic state of the cells of the cell culture.

This may be advantageous because it provides a very accurate assessment of the current metabolic state of the cells in a cell culture down to the level of individual intracellular fluxes.

According to embodiments the measurements also comprise a lactate dehydrogenase (LDH) concentration and at each point in time during the cultivation of the cell culture a LDH concentration measured in the medium of the cell culture is received. The predictions of the extracellular fluxes of the extracellular metabolites at each of the future points in time are made by the MLP using a corrected instead of the measured cell density.

Preferably, the calculation of the corrected cell density for each of the points in time comprises a calculation of the density of lysed cells in the medium of the cell culture as a function of the measured LDH concentration. This function may in particular be an empirically determined heuristic and linear function representing the dependence of the LDH concentration in the medium on the number of lysed cells of that specific cell type. The corrected cell density is then calculated as the sum of the measured cell density in the medium and the calculated density of the lysed cells.

This may be advantageous because cells that are completely or partially lysed are often not or only poorly detectable with optical methods for determining cell density, but the lysed cells may have had an influence on the concentration of extracellular metabolites until shortly before their lysis. Current methods for determining cell density only detect cells whose structure is still intact. This leads to a falsification of the total cell density determination if cell decay occurs, which tends to happen at later points in time in fermentation. It was observed that in some cases a systematic error was observed in the prediction of the fluxes with the method described here by embodiments, so that the predicted fluxes were not in agreement with the measurable fluxes but rather showed a systematic error. It was observed that this error correlated with the LDH concentration in the medium, which is an indicator for the presence of lysed cells in the medium. This enzyme is not released into the medium by an intact cell. The detection of LDH in the reaction medium thus indicates destroyed cells.

With the exception of batch fermentation, a similar, approximately linear relationship between the LDH concentration and the number of lysed cells has been demonstrated in many fermentation approaches. According to embodiments, the LDH concentration in the medium is used as a further measured value to calculate a corrected cell density.

According to embodiments of the invention, the corrected cell densities are used as input parameter values during training or application of the trained MLP.

According to embodiments, in the MLP-based predictions of the extracellular fluxes, in addition to the concentrations of the extracellular metabolites, the LDH concentration is used as an input variable to predict at least some of the extracellular fluxes of the model. According to embodiments, the LDH corrected value of cell density is used as an output variable in addition or alternatively to the concentrations of extracellular metabolites. Accordingly, according to embodiments of the invention, cell densities corrected by measured LDH concentration are used in the MLP training to calculate extracellular fluxes and/or an LDH concentration is used as a further input parameter value or as a concentration of an extracellular metabolite.

In another aspect, the invention relates to a system for predicting the metabolic state of a cell culture of cells of a specific cell type. The system comprises one or more processors, a first interface for receiving measurements from a bioreactor containing the cell culture and a volatile or non-volatile storage medium.

The storage medium includes a metabolic model of a cell of the specific cell type, the metabolic model including a plurality of intracellular and extracellular metabolites and a plurality of intracellular and extracellular fluxes, the metabolic model comprising stoichiometric equations specifying at least one stoichiometric relationship between one of the intracellular and one of the extracellular metabolites.

The storage medium further includes trained machine learning program logic (MLP) and program logic adapted to perform a method for predicting the metabolic state of the cells at each of a plurality of points in time during the cultivation of the cell culture. This method comprises:
receiving a plurality of measurement values measured at that point in time via the first interface, said measurement values comprising concentrations of a plurality of extracellular metabolites of the metabolic model in the culture medium of the cell culture and a measured cell density of the cells in the cell culture;
inputting the received measured values as input parameter values to the MLP;
predictions of extracellular fluxes of said extracellular metabolites at a future point in time by said MLP using said received measurement values, said future point in time being a point in time subsequent to the time of receipt of said measurement values, wherein said extracellular fluxes are uptake rates of said extracellular metabolites into a cell and/or release rates of said extracellular metabolites from a cell into said medium;

performing metabolic flux analysis to calculate the intracellular fluxes at the future point in time using the predicted extracellular fluxes and the stoichiometric equations of the metabolic model.

The metabolic model may, for example, be stored in the storage medium in the form of a set of stoichiometric reaction equations defined in MatLab. The storage medium may be the main memory of a computer or an electromagnetic or optical storage medium, e.g. a hard disk. The storage medium may also be a distributed system of several hardware storage units, for example a cloud storage area offered by a cloud service or the IT infrastructure of a laboratory. The system may, for example, be implemented as a standard computer, or as a notebook or portable mobile device of a user. The system may be integrated into a Laboratory Information System (LIS) or operationally connected to it. However, the system may also be a control computer for one or more bioreactors or a control module that is reversibly or irreversibly coupled to a single bioreactor, for example as an integral part of the bioreactor.

For example, the first interface may be a network interface that establishes a wireless or wire-based connection to one or more sensors of the bioreactor. In addition or alternatively, the first interface may also be an interface for manual input of the corresponding measured values. For example, it is possible that the measured values are obtained by taking a sample from the bioreactor at specific points in time in a manual, semi-automatic or fully automatic method, which is then transported to one or more further analysis devices, where the cell density and/or the concentration of extracellular metabolites is then determined. The measured values obtained in this way may in turn be automatically transferred from these analyzing devices to the system via the first interface or a user may enter the measured values manually into the system via a first interface designed as a graphical user interface.

According to embodiments, the system is a control unit for monitoring and/or control of one or more bioreactors or is operatively linked to such a control unit. Preferably, the system further comprises a user interface for outputting the calculated intracellular flux to a user. For example, the predicted flows may be displayed in tabular form or the flows may be dynamically visualized by means of a dynamic image, e.g. a dynamic image based on a graphical representation of the metabolic model underlying the prediction of the intracellular flows.

According to embodiments of the system, the system also comprises a second interface for sending control commands to the bioreactor. This program logic is adapted to:
  comparing the predicted intracellular flux with reference values or reference value ranges for an acceptable intracellular flux of the respective intracellular metabolite(s);
  issuing a warning via the user interface if a deviation of the calculated intracellular flux of at least one of the intracellular metabolites from its respective reference value or reference value range exceeds a limit value; and/or
  sending a control command to the bioreactor via the second interface, the control command being adapted to change the state of the bioreactor or the medium contained therein in such a way that the deviation is reduced.

The user interface may, for example, be a graphical user interface (GUI) and/or an acoustic user interface. For example, a warning tone may be given via the acoustic user interface or a warning in the form of a text, preferably with a qualified indication of the intracellular flux for which the deviation has been detected, may be displayed on a screen via the GUI. The screen may be a screen coupled to the bioreactor or the screen of a computer connected to one or more bioreactors via a network, for example a desktop computer, a server or a mobile communication device, for example a user's smartphone.

The second interface may, for example, be physically adapted as a wireless or wire-based connection between the system and the bioreactor or bioreactor actuators. The actuators may be pumps, valves for various nutrients, buffers, pH-regulating liquids, trace elements, gases and/or stirrers or temperature controllers.

A "training point in time" is a point in time during the generation of the training record. In contrast, the "point in time" according to claim 1 refers to a later point in time when the MLP trained on the training data set is applied to predict the metabolic state of a currently monitored and/or controlled bioreactor.

A "metabolite" in the narrow sense of the term is an intermediate product (intermediate) in a biochemical metabolic pathway. However, a metabolite in the sense of the present invention shall be broader than any substance which, in the form of an educt, product or intermediate, is involved in a biochemical reaction of a cell. In particular, a metabolite may be an amino acid, a sugar, fats, peptides, antibodies, proteins, components of the citrate cycle, components of glycolysis, components of protein synthesis or degradation pathways and similar substances.

An "extracellular metabolite" is understood here to be a metabolite that is known or assumed to occur in the medium of a cell culture according to a metabolic model of the cell type under investigation, e.g. because it is secreted into the medium of the cell culture by cells of the specific cell type (e.g. lactate) or because it is added to the cell culture as a component of the medium or a culture medium (e.g. glucose).

An "intracellular metabolite" is defined here as a metabolite that is known or assumed, according to a metabolic model of the cell type under investigation, to occur within cells of the specific cell type, e.g. because it is taken up from the medium of the cell culture or is produced by the cells.

A "flux" is a quantity of a substance that changes per time in a specific volume due to a specific transport or reaction process. A flux is therefore also called a "reaction rate" or "transport rate". If several processes take place simultaneously in a specific volume, it is possible that the net concentration of a substance does not change due to the counter-rotational nature of some processes. e.g. through substance conversion, uptake or release.

According to embodiments, the volume to which a flux indication refers is the volume of a cell for intracellular as well as extracellular metabolites.

Because the change in the amount of substance caused by the specific process is related to the cell or the cell volume, a flux implicitly also indicates a change in the concentration of this substance per time in this volume caused by the specific process, which is caused by this specific reaction or transport process. Since, for a given volume, the flux of a substance implicitly also indicates a change in concentration of this substance in the volume caused by the specific process and vice versa, the concept of a flux here should equally comprise a change in a quantity of substance per time in a volume as well as a quantity of concentration per time.

Preferably, the metabolic model used after embodiments of the invention assumes that the amount or concentration of intracellular metabolites remains approximately constant. However, this does not mean that the intracellular fluxes remain constant. Rather, a cell in whose cytosol the concentration of an intracellular metabolite increases rapidly may compensate for this, e.g. by increasing the reaction rate of one or more chemical reactions which metabolize this metabolite.

An "extracellular flux" is understood here to be the rate at which an extracellular metabolite is taken up or released by the cell via a specific transport process. More precisely, it is the amount of the metabolite that is taken up into the cell per cell and per time by this specific transport process, or is released by the cell into the surrounding medium. According to the embodiments of the invention, the extracellular flux v of a component at time t is determined on the basis of the measured change in the concentration of the corresponding metabolite in the reactor medium, which is normalized with the living cell density.

According to embodiments, for example, the change in concentration of the extracellular metabolite in the culture medium is measured over a time interval. This may be used to calculate the absolute change in the amount of metabolite in the medium (using the volume of the medium in the reactor). The live cell count in the medium may be measured. By normalizing the absolute change in the amount of the extracellular metabolite to the cell number, the extracellular flux may be given as a specific (biomass related) quantity. Since the average volume of a single cell of the cultured cell type is usually known from literature or may be measured, a conversion of the measured change in concentration to the average cell volume is performed according to embodiments of the invention.

For example, the metabolic model of cell metabolism used for metabolic flux analysis (also "flow analysis" or "material flow analysis") may include extracellular stoichiometric reaction equations, each of which is associated with an extracellular flux. Thus, extracellular fluxes describe in particular uptake rates of extracellular metabolites into the cells of a cell culture, so that these then function as intracellular metabolites, and release rates of extracellular metabolites of the cells of the cell culture to the surrounding medium, so that these then occur there as extracellular metabolites.

Via these extracellular fluxes, which represent transport fluxes into and out of the cell, the purely intracellular fluxes are linked to the concentrations and concentration changes of the extracellular metabolites in the metabolic model and allow the determination of plausibility criteria based on the stoichiometries specified in the model and the empirically determined or allow descriptive assessments of current intracellular fluxes of the cell and/or predictions of future intracellular fluxes of the cell on the basis of the extracellular fluxes using the stoichiometries, plausibility criteria and the empirically determined or predicted concentration changes of the extracellular metabolites in the medium specified in the model.

The intracellular and extracellular fluxes are thus coupled together in the metabolic model via one or more intracellular metabolites, since some substances occur both as intracellular metabolites, whose rate of formation from or metabolization into one or more intracellular metabolites is described, and whose rate of import into the cell or release from the cell is described by extracellular fluxes of the model.

A change in the concentration of an extracellular metabolite and thus an extracellular flux may also be caused in some types of bioreactors by an external addition or feeding of this metabolite into the cell culture medium. An extracellular flux may be calculated approximately, e.g. by first determining the absolute difference in the metabolite concentration measured at two consecutive points in time and then converting this difference to the measured cell density. The higher the cell density, the lower the flux per cell, since the absolute measured change in metabolite concentration is distributed over a larger number of cells. The uptake flux of an extracellular metabolite at the future point in time may therefore be calculated as the difference in metabolite concentration measured in the time interval between the two points in time divided by the duration of the time interval, the result then being divided by the measured cell density.

An "intracellular flux" is understood here to be the rate (a quantity related to a time interval) at which a reaction takes place within a cell, whereby the reaction may consist of: a transport between intracellular compartments (e.g. transport from the cytosol into the mitochondria and vice versa) or a conversion of one or more intracellular metabolites (educts) into one or more other metabolites (products) in the cell. In case of an intracellular flux, all educts and products are intracellular metabolites.

Intracellular fluxes are formulated in the metabolic model for stoichiometric equations that specify a reversible or irreversible reaction of the above categories (intracellular transport between cell compartments, metabolic transformation).

"Unmeasurable fluxes" are fluxes which may not be readily determined from the fermentation data. In general, intracellular fluxes are not measurable because of the difficulty in observing intracellular metabolites.

According to preferred embodiments of the invention, MFA for the determination of intracellular fluxes based on provided extracellular fluxes is based on the assumption that the concentration of an intracellular metabolite does not change. Concentrations of intracellular metabolites are very difficult or impossible to measure. Embodiments of the invention are based in MFA on the assumption that the sum of input and output flows at an intracellular metabolite (whose concentration is unknown) is identical and therefore its concentration does not change. Depending on the operating mode of the reactor, this is not exactly correct, but at least approximately sufficiently correct with regard to the time intervals described here, since the cell metabolism returns to its chemical equilibrium quite quickly.

According to embodiments, the metabolic model used in MFA comprises at least 10, preferably at least 20 stoichiometric equations. The model is preferably adapted to describe metabolic processes in the cell completely or at least approximately completely.

The use of a metabolic model which comprises the cell metabolism as comprehensively as possible may be advantageous, since for the selection of specific cell clones it is important to have as complete a picture as possible of the individual metabolic activities and particularities of each cell clone investigated. A pure plausibility check of the extracellular fluxes predicted by MLP by means of individual stoichiometric equations would generally not provide sufficient data to be able to select specific cell clones based on this model due to their advantageous metabolic properties.

In another advantageous aspect, the use of the metabolic model with a large number of stoichiometric equations in MFA may also be used to monitor cell cultures and, in case of deviation of one or more metabolite fluxes from a set point range, to make specific changes in the amount and/or composition of the nutrient solution supplied or other control parameters (temperature, pH, partial pressure oxygen, partial pressure CO2, speed stirrer etc) automatically and/or manually.

A "metabolic model" is understood here to be a descriptive model of the current metabolic state of cells of a specific cell type. The metabolic model is preferably reduced in complexity compared to the real reactions taking place in the cell and is restricted to those parts of the cell metabolism which are of particular interest for the respective application. Preferably, the model includes several extracellular and intracellular metabolites, reaction and transport equations with stoichiometric factors, and extracellular and intracellular fluxes. The metabolic state of a cell may be characterized, at least in part, by indicating the level of the individual intracellular fluxes at a specific point in time. Preferably, the temporal change of metabolite amounts in the cell results from the balancing of incoming and outgoing material flows, as specified in the extracellular and intracellular reaction equations of the model. The model is an MFA model suitable for performing metabolic flux analysis and is based on the so-called steady-state assumption that the amount of intracellular metabolites remains constant, which means that the sum of the incoming fluxes for each intracellular metabolite is equal to the sum of the outgoing ones.

The concentrations of extracellular metabolites measured and used as input parameter values of a trained MLP are, according to embodiments of the invention, metabolite concentrations in the strict sense. A metabolite concentration in the narrow sense of the term is understood here to be a content specification related to a volume. The concentration thus indicates how much of a metabolite is present in a reference volume (e.g. cell culture medium). The metabolite concentration may, for example, be indicated as mass concentration in the unit g/l or as substance quantity concentration in the unit mol/l.

According to other embodiments, the concentrations of extracellular metabolites measured and used as input parameter values of a trained MLP are metabolite concentrations in the broad sense. A metabolite concentration in the broader sense here means measured values and values derived therefrom which are known to correlate with a metabolite concentration in the narrower sense of the respective metabolite in a linear manner or at least approximately (at least 90% in the concentration range in question) in a linear manner. For example, an extracellular flux of an extracellular metabolite may be understood as a metabolite concentration in a broader sense. The measured extracellular flux refers to the change in the concentration of the metabolite in the medium in the period between a point in time in the past, e.g. the last measurement of the metabolite concentration, and a current point in time at which the measured values are currently collected and used as input for the MLP. The essentially linear relationship between measured flux and extracellular concentration results from the fact that an increase in the extracellular flux of a metabolite by a specific amount causes a corresponding change in the concentration of the metabolite in the extracellular medium. Furthermore, according to embodiments of the invention, the measured metabolite concentrations may still be modified in various ways by offsetting with correction and normalization factors, so that these modified values ultimately also represent metabolite concentrations in the broader sense, i.e. correlate in a linear manner with the originally measured values, but are not identical to them. Since the actually measured metabolite concentration and the metabolite concentration in the broader sense correlate linearly with each other or the metabolite concentration may be derived from the measured metabolite concentration in the narrower sense, both types of metabolite concentration data may ultimately be used equally as input for an MLP.

A "descriptive model" is a model that describes the current static and dynamic metabolic state of a cell.

A "predictive model" is a model that allows the prediction of a future static and dynamic metabolic state of a cell. By embodiment, the metabolic model used for flux analysis is a descriptive metabolic model.

A "metabolic hybrid model" is a combination of a mechanistic model, which represents reaction kinetic knowledge, and an empirical model, which relates measured values from a bioreactor to metabolic states of a cell.

A "metabolic flux analysis" (MFA) is a computational method that may be used to estimate intracellular fluxes from extracellular fluxes. The extracellular material flux describes the amount of material that is absorbed or released by a cell over time.

The intracellular material flux describes the reaction rate with which an intracellular metabolite is converted or formed. MFA comprises different approaches to determine the rate of metabolic reactions within a biological unit. Metabolism is a dynamic process and may be regarded as a kind of "cellular phenotype" described by MFA.

A "batch bioreactor" is a bioreactor which is operated in a "batch process" or is adapted to operate in a batch process. The batch method is characterized by the fact that all substrates (especially sugar and amino acids) are presented in the bioreactor before being inoculated. Gases and PH correction agents, on the other hand, are also introduced into the system during the process. Approximately, however, the batch process may be regarded as a closed system with a constant reaction volume. Due to the gradual consumption of the substrates by the cells, an initial unlimited growth phase (so-called exponential phase) is followed by a phase of stagnation (stationary phase) in which the growth and death of the cells are in equilibrium. This is followed by the death phase with a decrease in cell density as a result of a severe lack of nutrients. Among the usual methods of bioreactor operation, the batch method is the least costly and least likely to cause contamination. However, the batch process does not usually result in an optimal product yield; the process duration is limited by the consumption of the substrates.

A "fed-batch bioreactor" is a bioreactor which is operated in an inlet method ("fed-batch method") or is adapted to operate in a fed-batch method. In the fed-batch method, additional culture medium is added during the process (often only after an initial batch phase). The feed may be continuous or in the form of one or more highly concentrated boluses (i.e., pulsed). Compared to the batch method, the process time can be extended, since used substrates may be re-dosed. Furthermore, a better process control may be achieved. For example, inhibition phenomena and the formation of toxic by-products can be contained by keeping educt concentrations continuously lower. Overall, the fed-batch method may achieve significantly higher cell densities and product yields than the batch method.

A "chemostat" ("continuous reactor") is a bioreactor to which a constant flow of culture medium is supplied and from which reaction medium containing cells and products is withdrawn in equal measure. Thus the reaction volume does not change during fermentation. If the volume flows are chosen appropriately, a steady state equilibrium is established in the reactor, in which the cell density and the nutrient concentrations remain constant.

A "perfusion bioreactor" or "perfusion reactor" is a bioreactor in which a continuous stream of culture medium is added and a continuous stream of (usually cell-free) reaction medium is withdrawn. A continuous stream of cell-containing reaction medium may also be removed by means of directed "bleeding". The choice of volume flows is linked to one or more process control parameters and adjusted so that the reaction volume in the reactor remains constant. Cell density and nutrient concentrations may be constant (related to the cell density) or variable (similar to fed-batch operation) depending on the process design.

A "split-batch bioreactor" is a bioreactor of the batch or fed-batch type operated in such a way that a substantial part of its medium, e.g. more than 10% or more than 30%, has been removed from the reactor one or more times for the purpose of harvesting the cells contained therein.

The "PMI" (partial mutual information) is a data value which quantifies non-linear direct dependencies of two parameters. In the context of some machine learning approaches, e.g. neural networks, the PMI is a measure for the dependence between a random input variable X and a random output variable Y, taking into account already selected inputs. Different approaches to calculate the PMI of two variables are known, e.g. Sharma A (2000): "Seasonal to interannual rainfall probabilistic forecasts for improved water supply management: Part 1—A strategy for system predictor identification", Journal of Hydrology Vol. 239, Issues 1-4, 232-239.

A "PMI criterion" thus refers to a feature or characteristic that has been established with regard to PMI in order to make a decision. For example, a PMI criterion may be a limit value, the exceeding or falling below of which influences the course of a method.

Some examples of the invention are explained in greater detail in the appendix attached to this application, the disclosure content of which is part of this application. In order to ensure consistency between the description and the appendix, the meaning of the variables as specified in the variable directory of the appendix has been retained. With regard to the meaning of the variables, reference is made to the list of variables in the appendix. Examples and embodiments as well as further explanations described in the Appendix can be freely combined with the embodiments, examples and features described in the application text, provided they are not mutually exclusive.

SHORT DESCRIPTION OF THE FIGURES

In the following, embodiments of the invention are described in more detail in an exemplary manner, whereby reference is made to the figures which each represent embodiments of the invention or individual aspects of these embodiments.

Figure 3A:
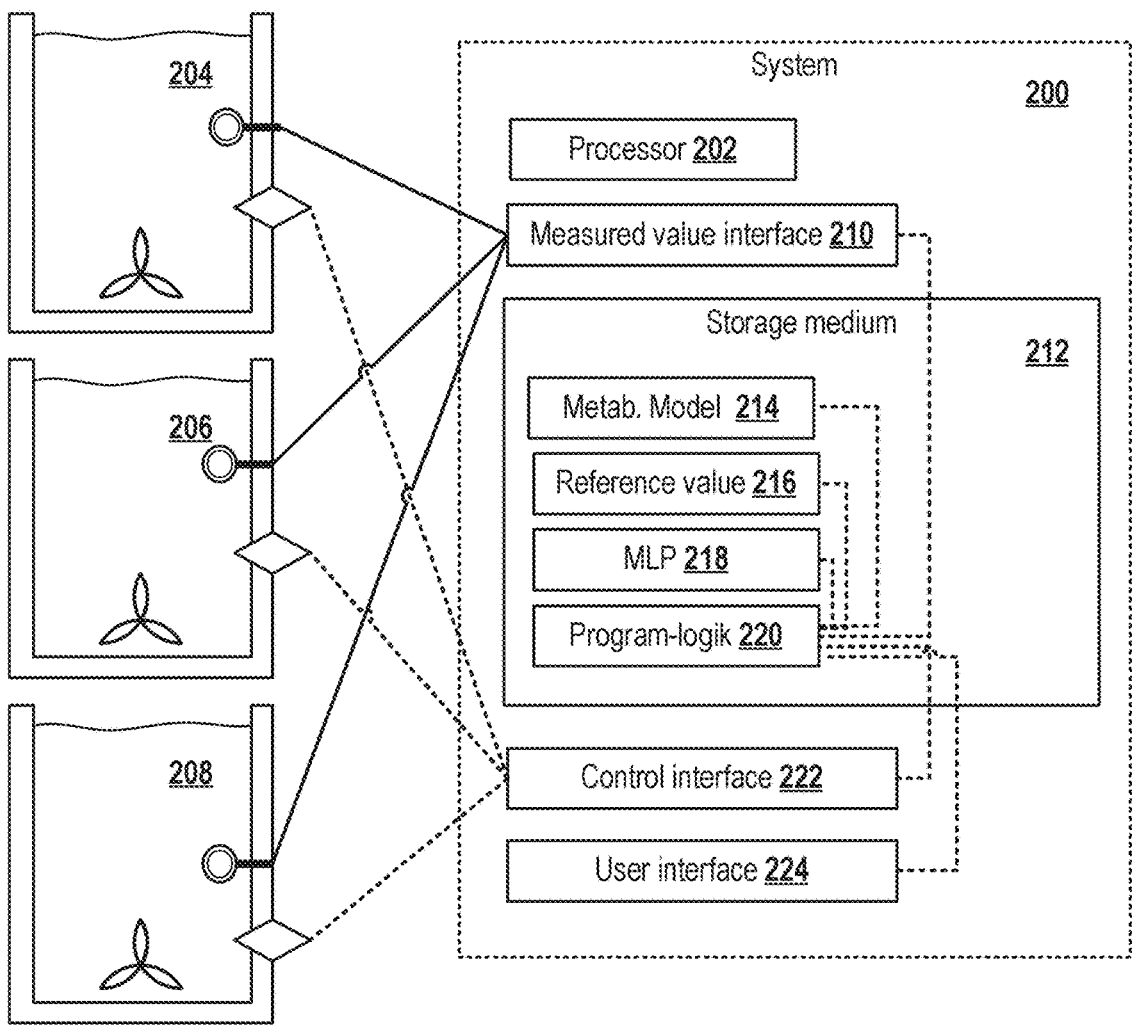
Figure 4A:
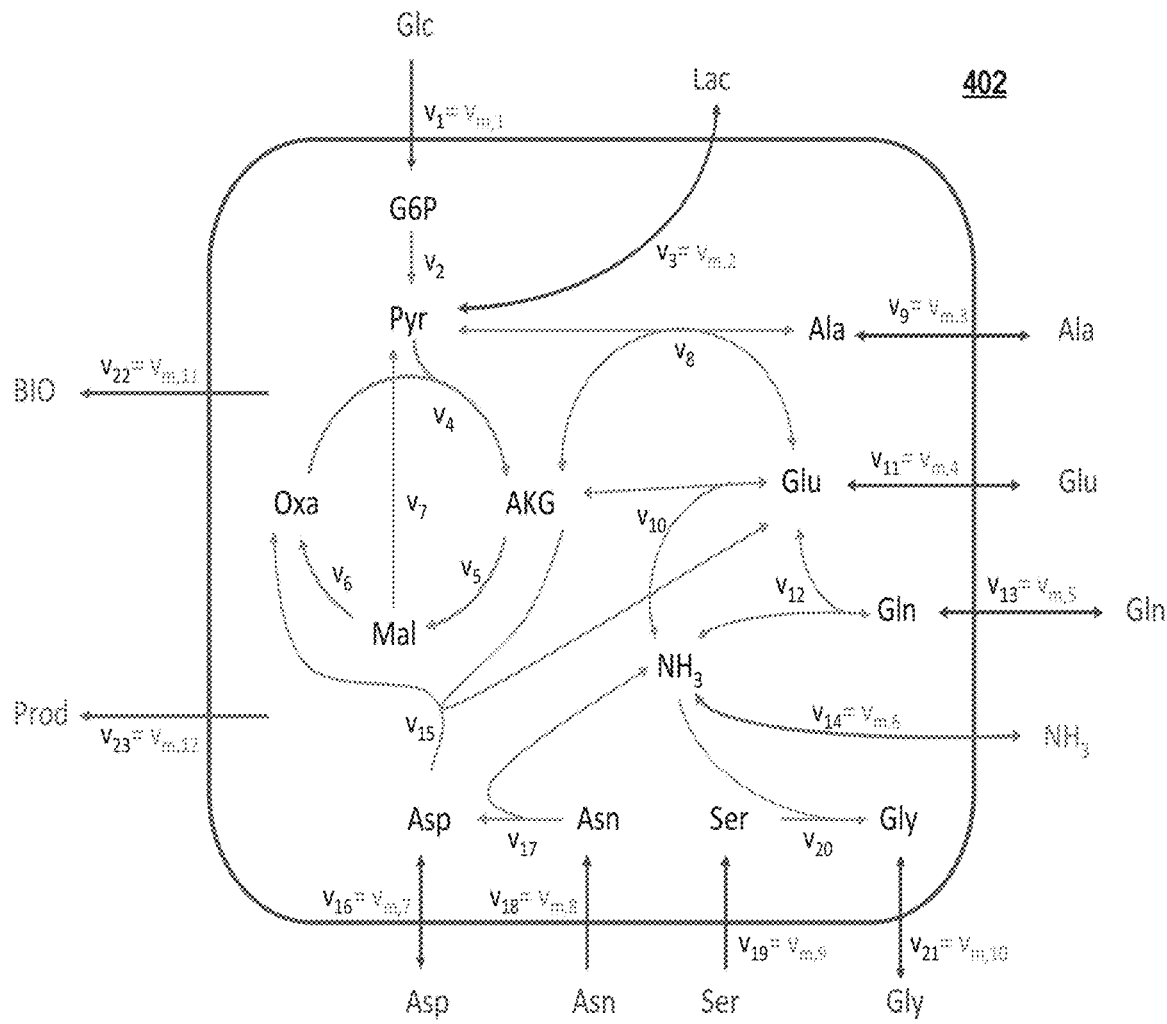
Figure 5:
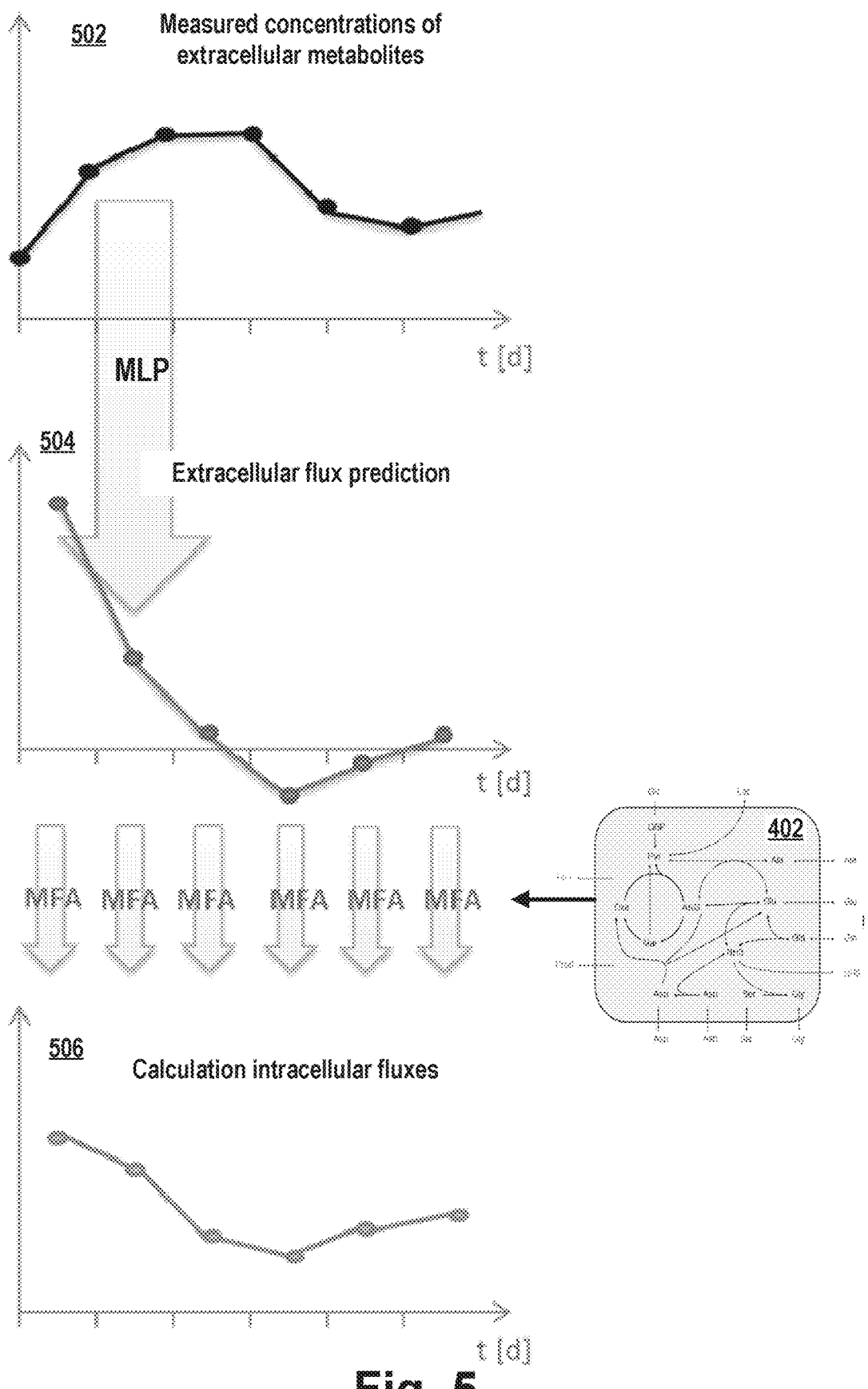
Figure 6:
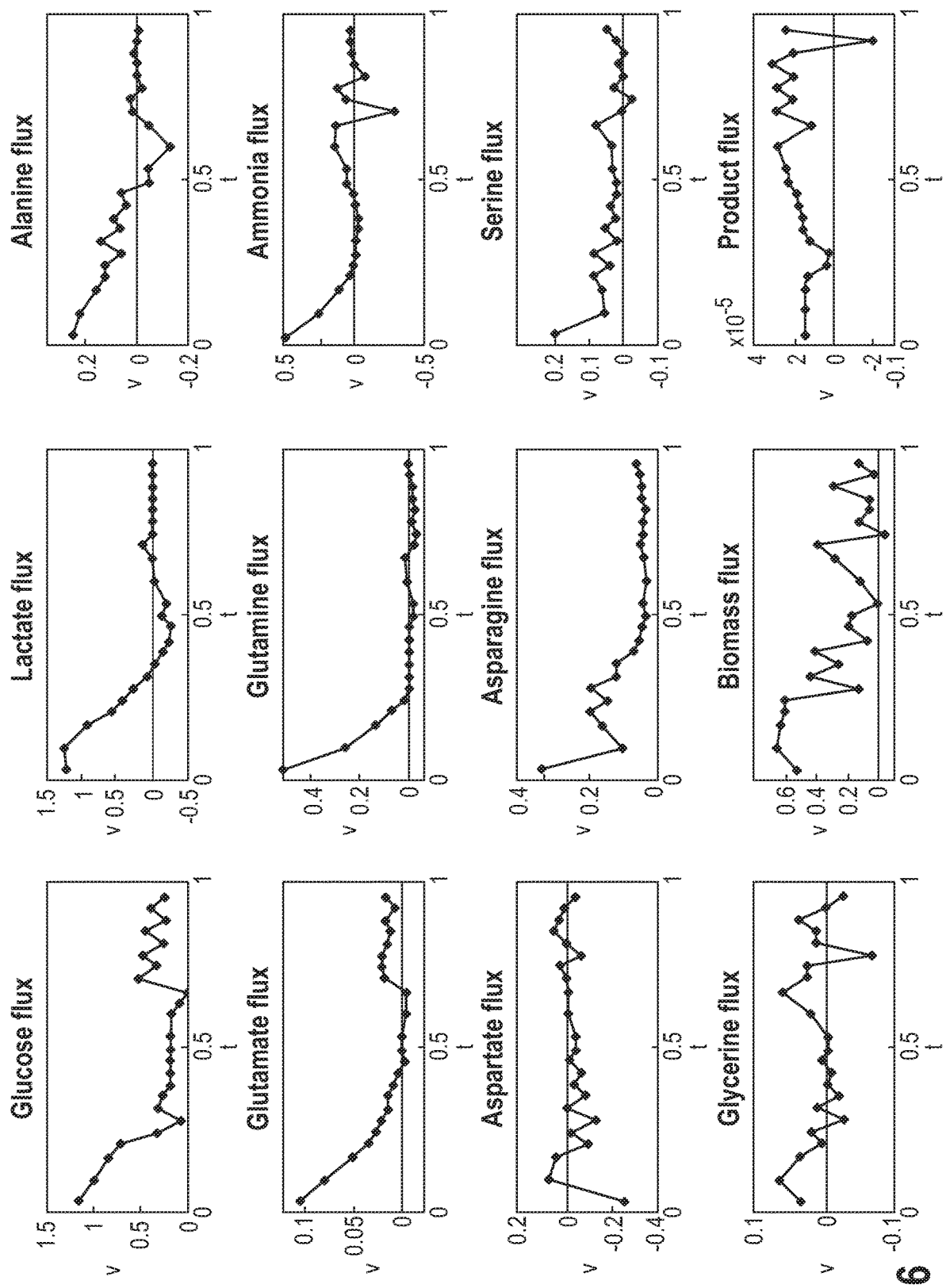
Figure 7:
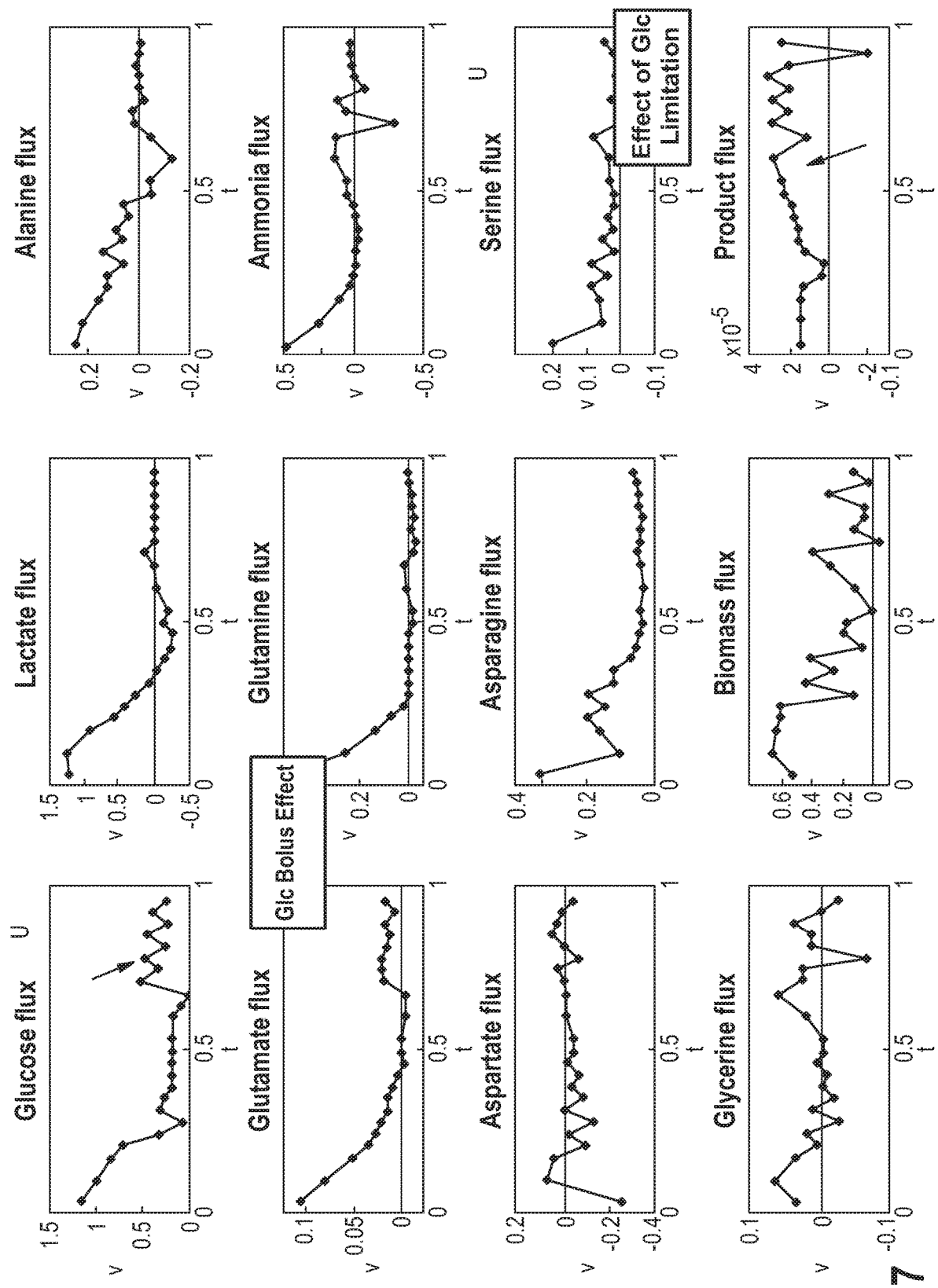
Figure 8:
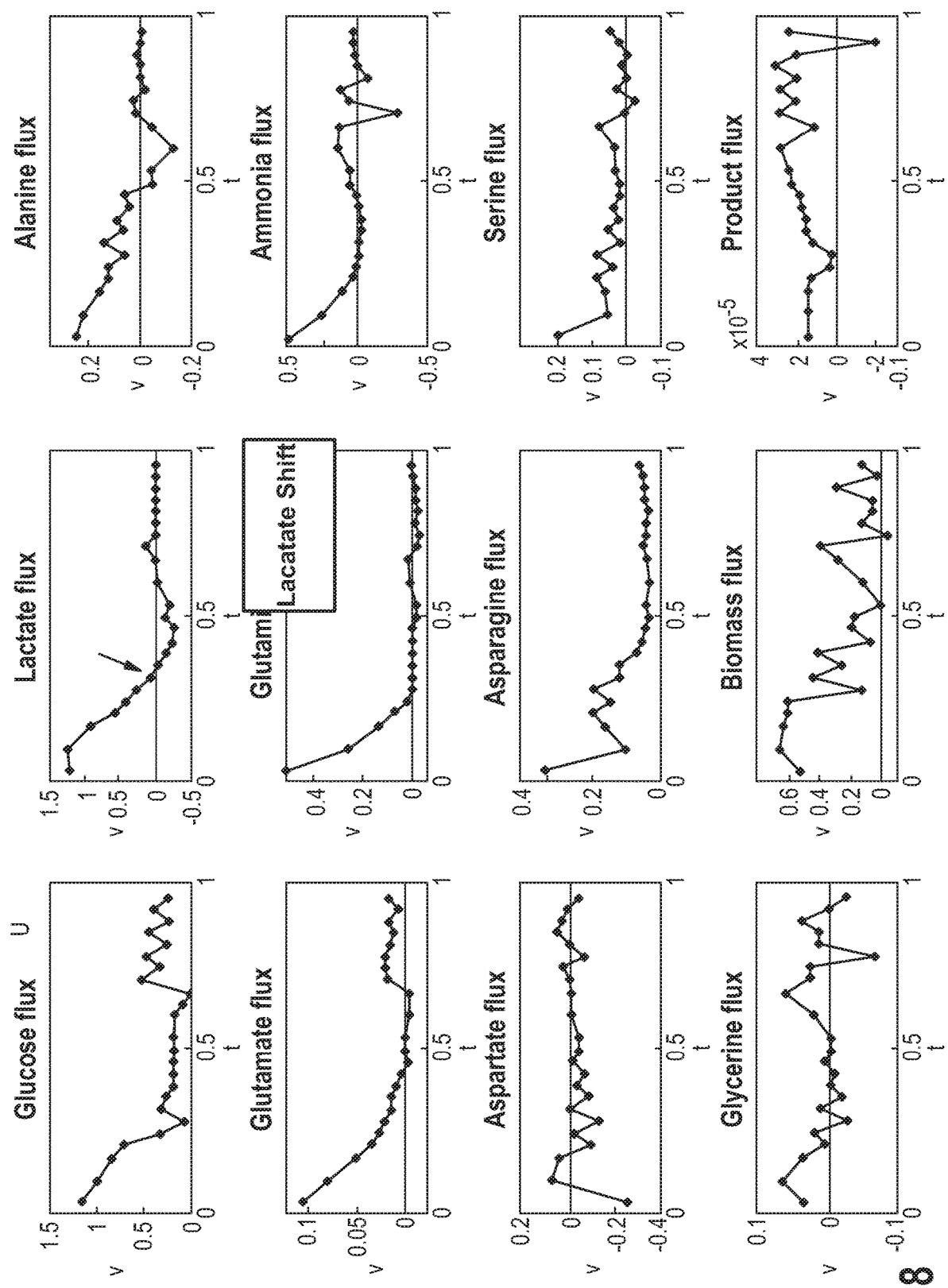
Figure 10:
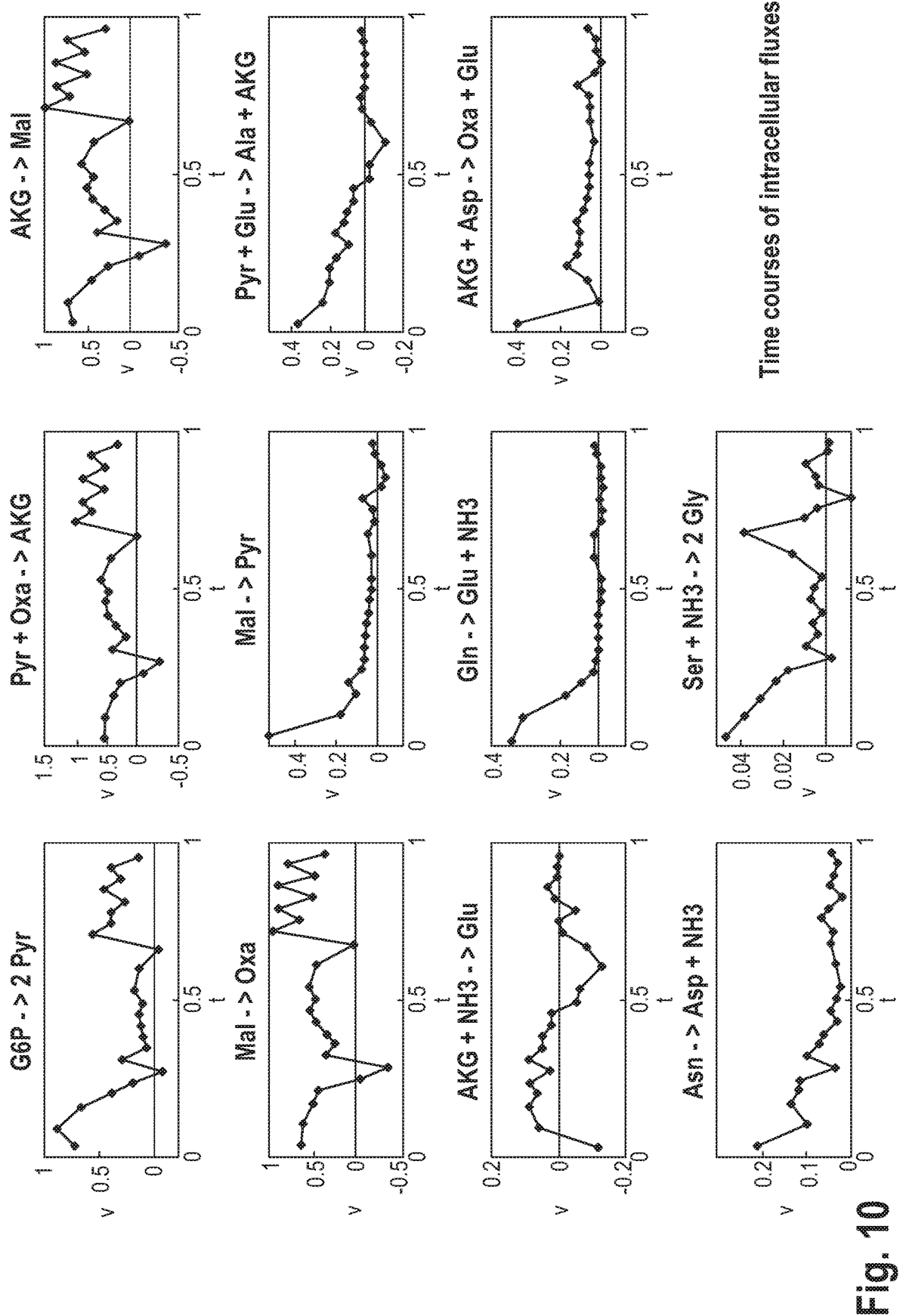
Figure 12:
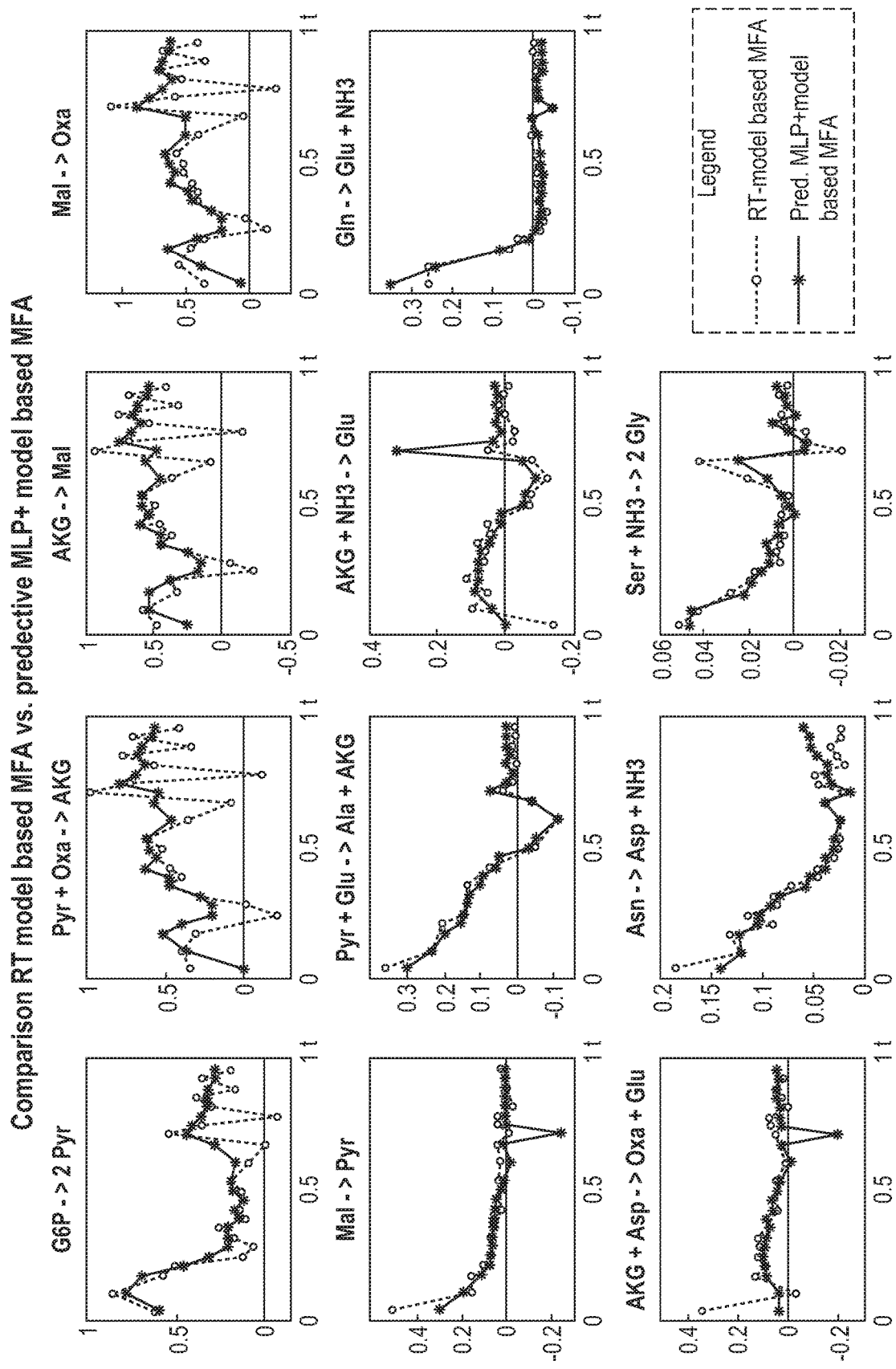
Figure 14:
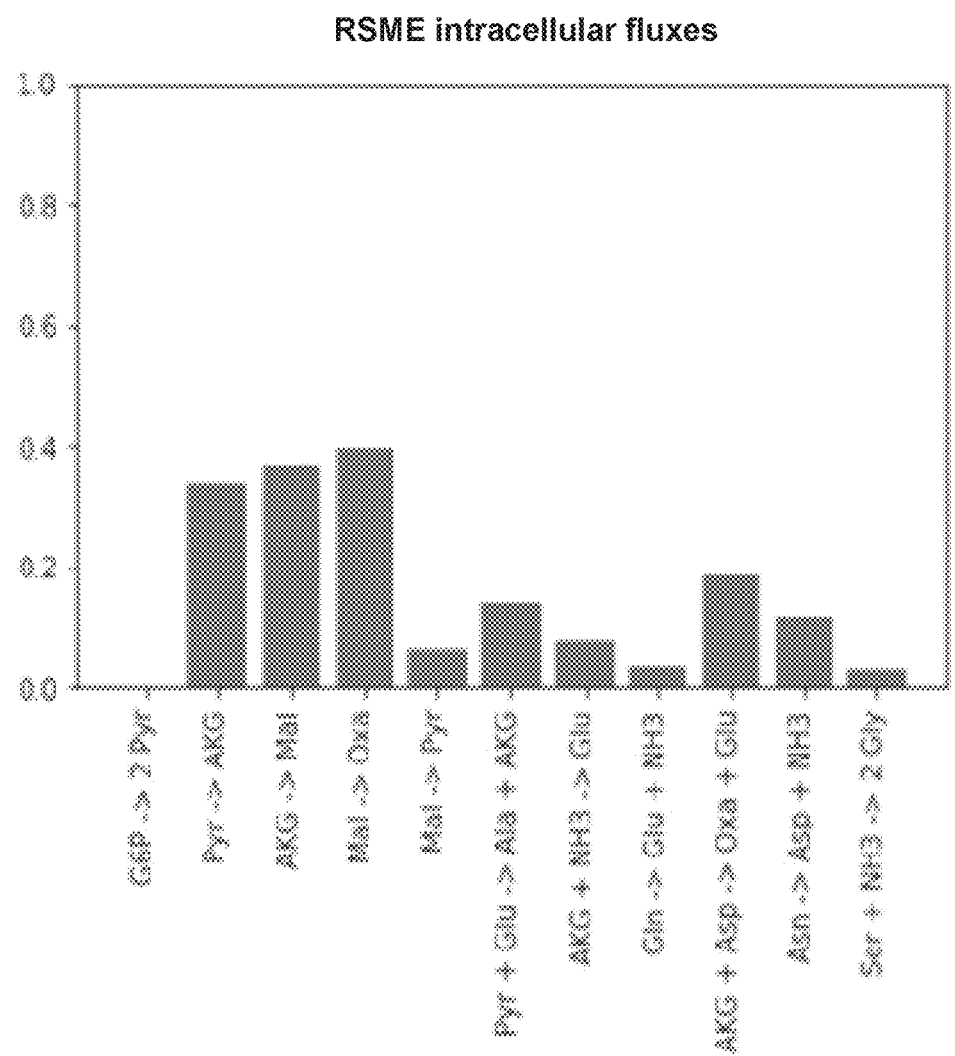
Figure 15:
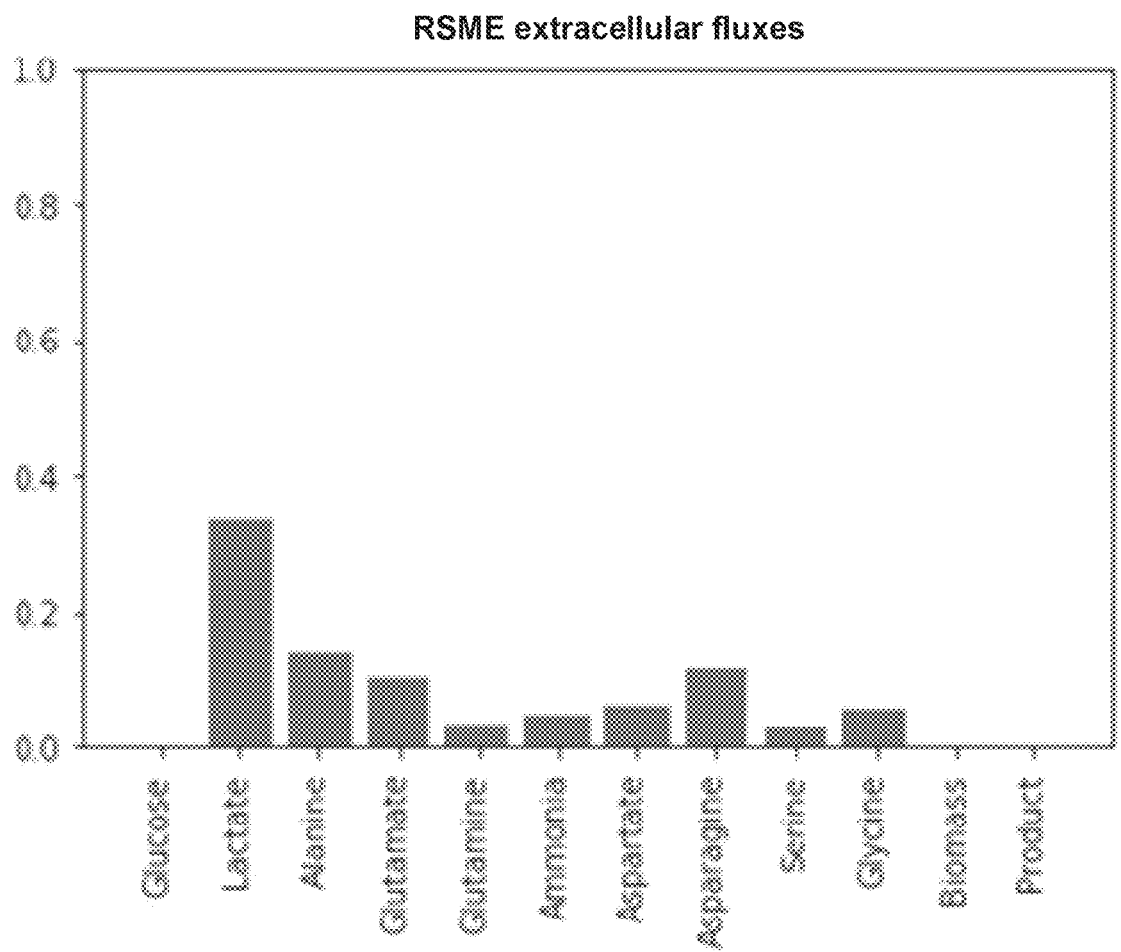
Figure 16:
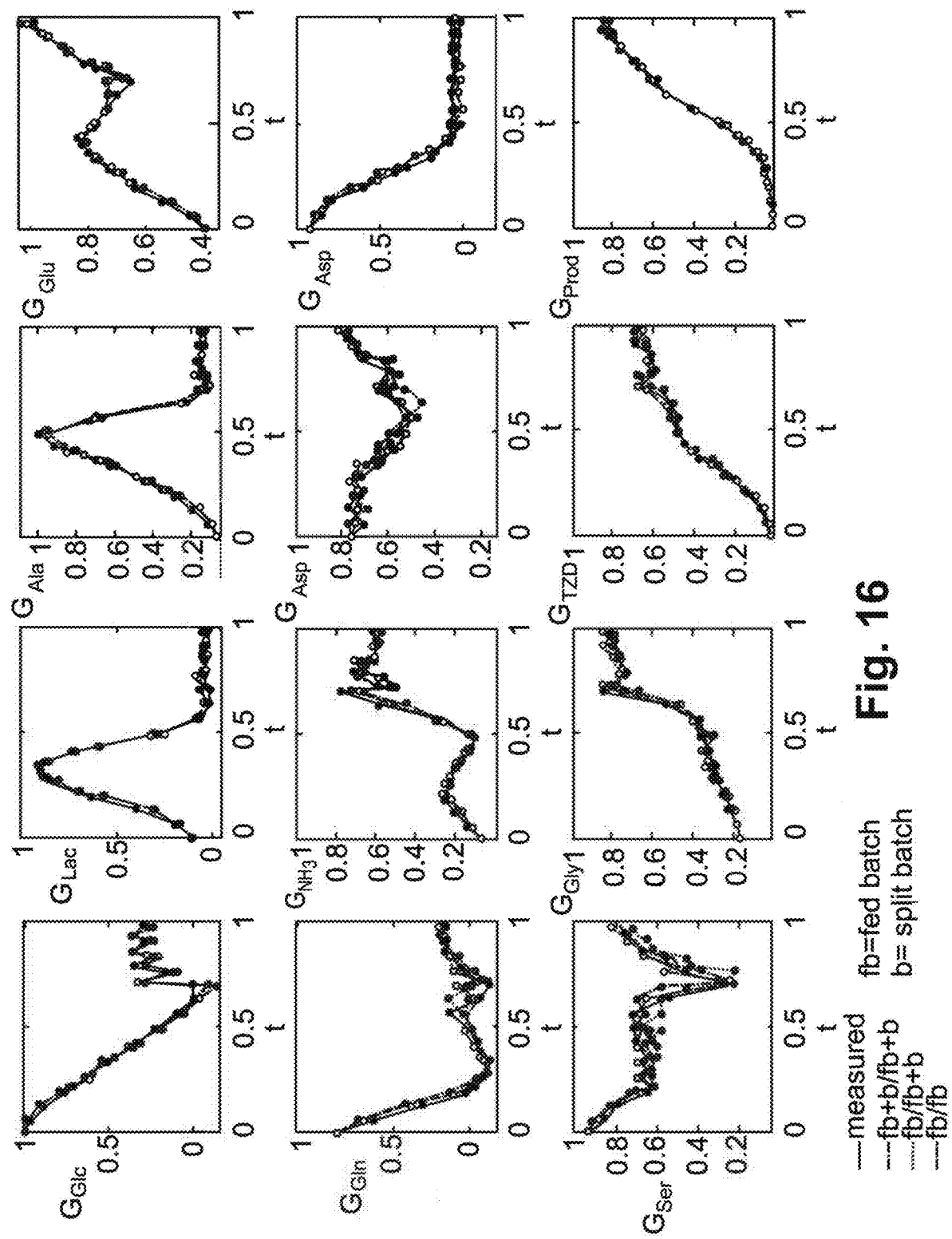
Figure 17:
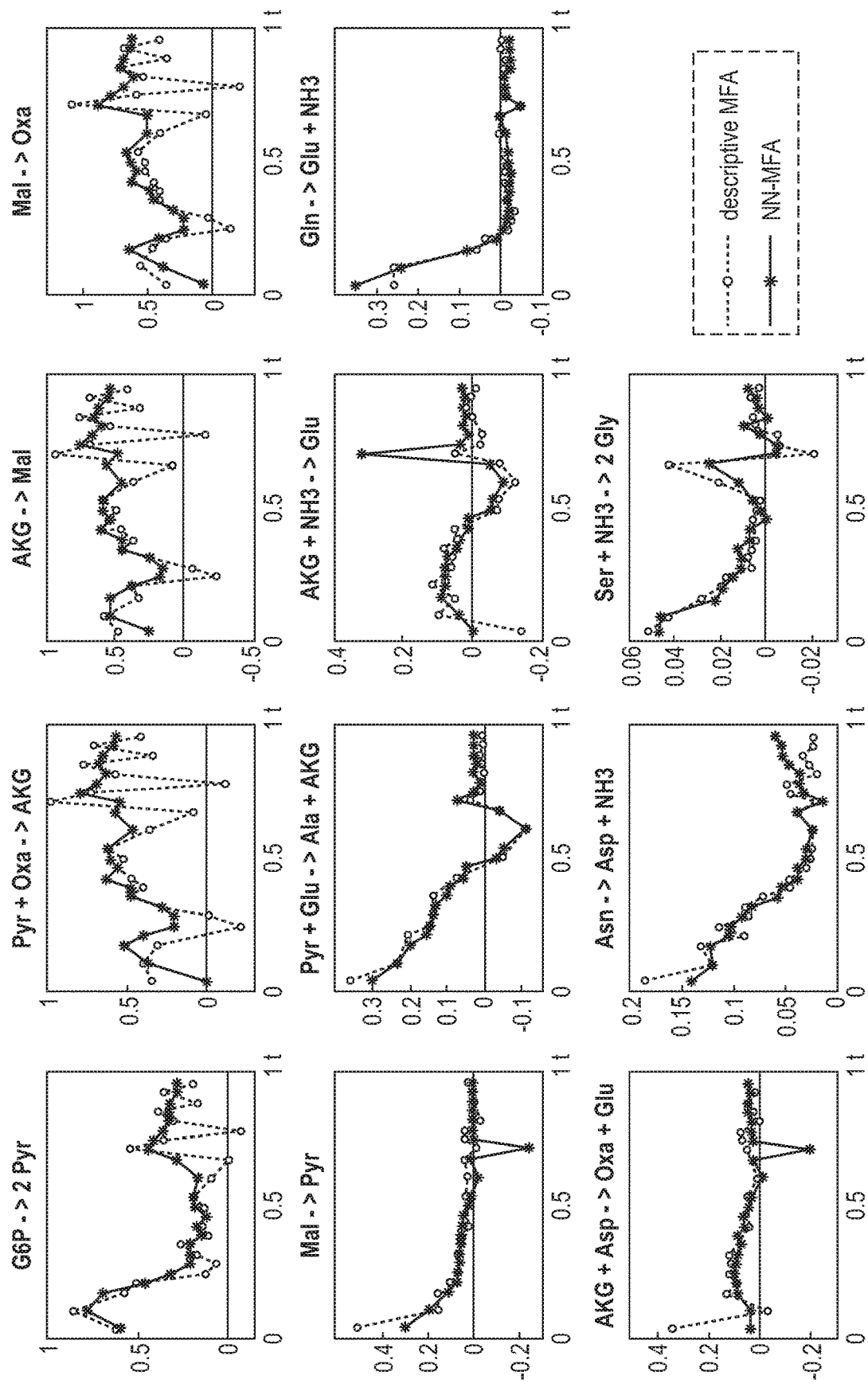
Figure 18A:
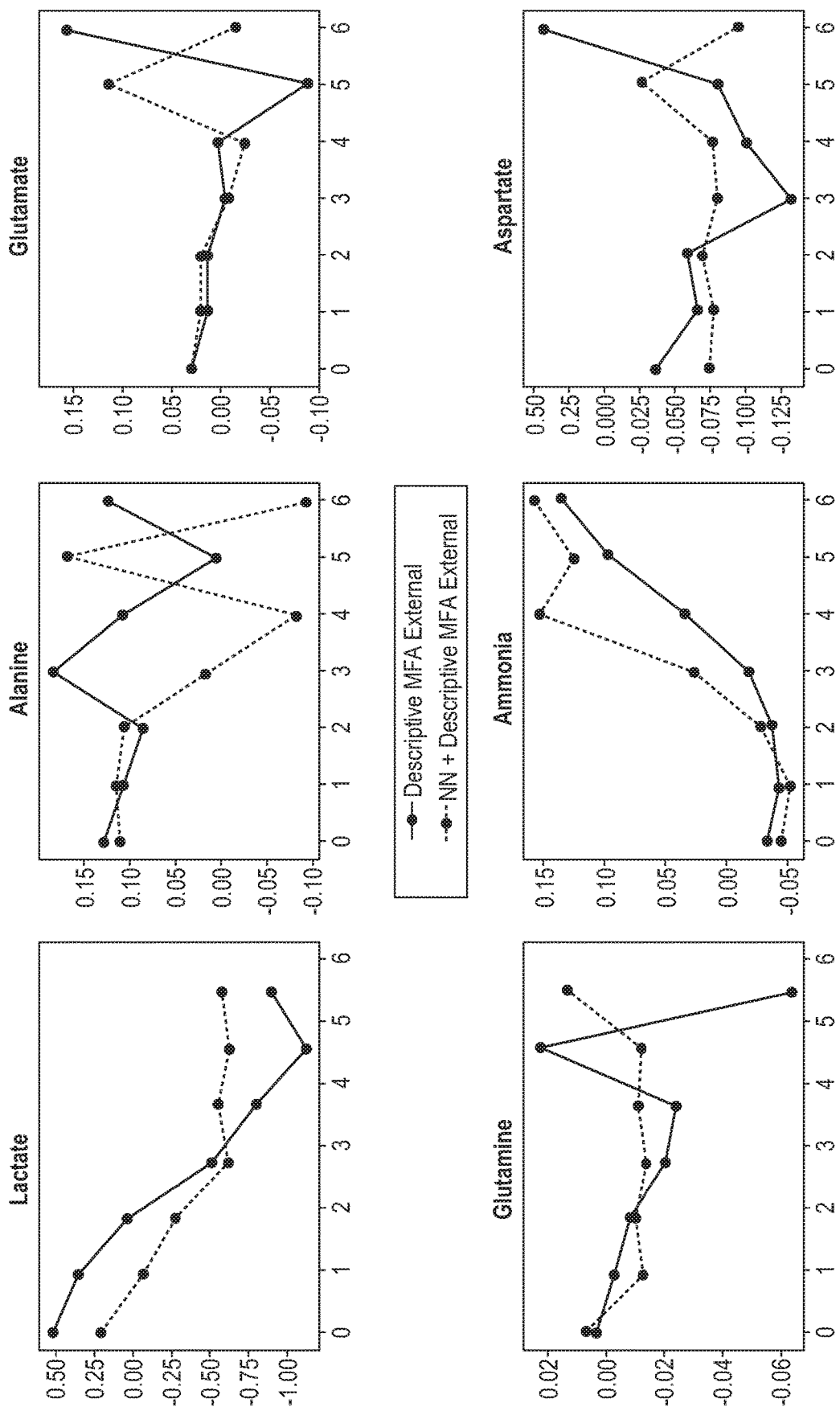
Figure 18B:
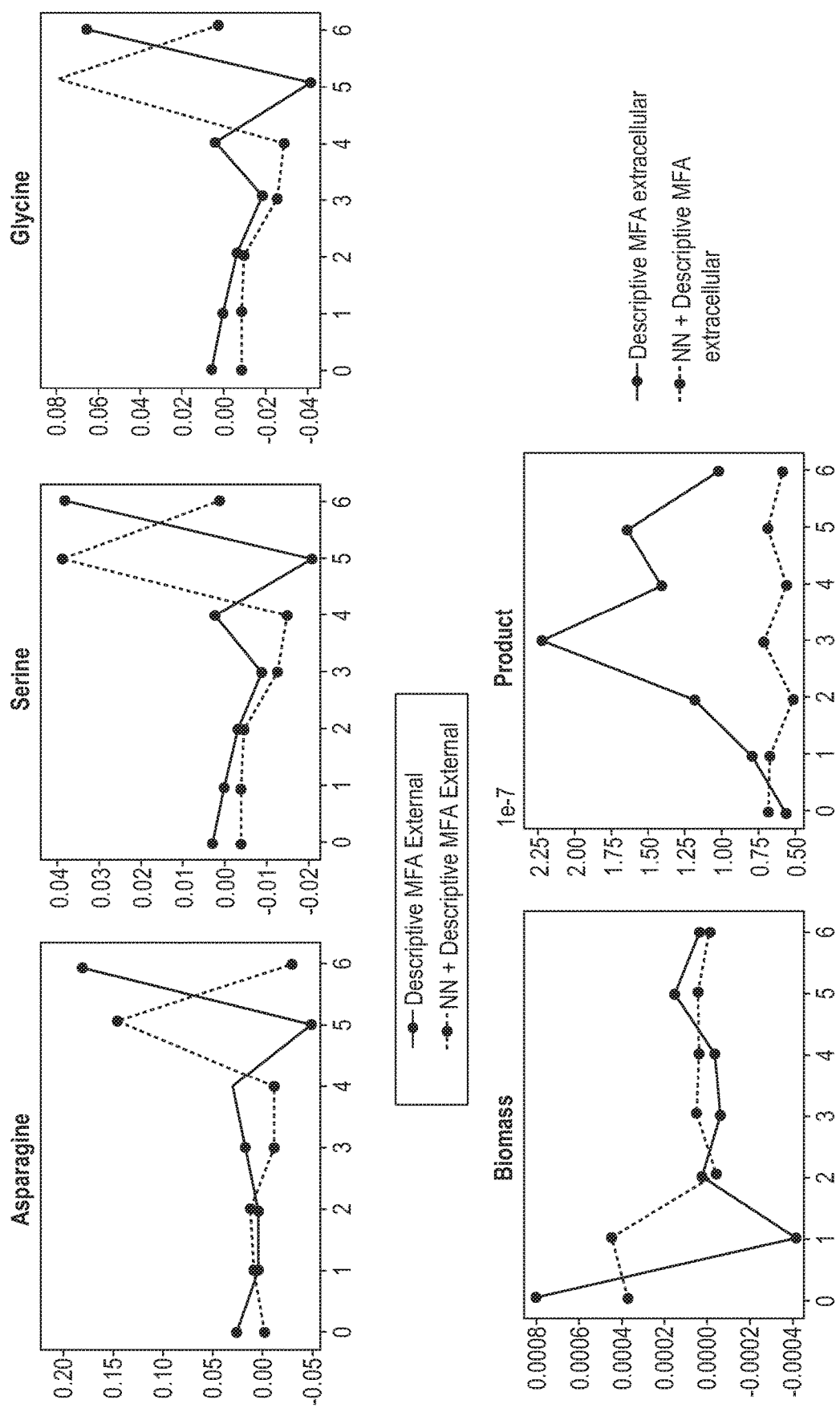
Figure 19A:
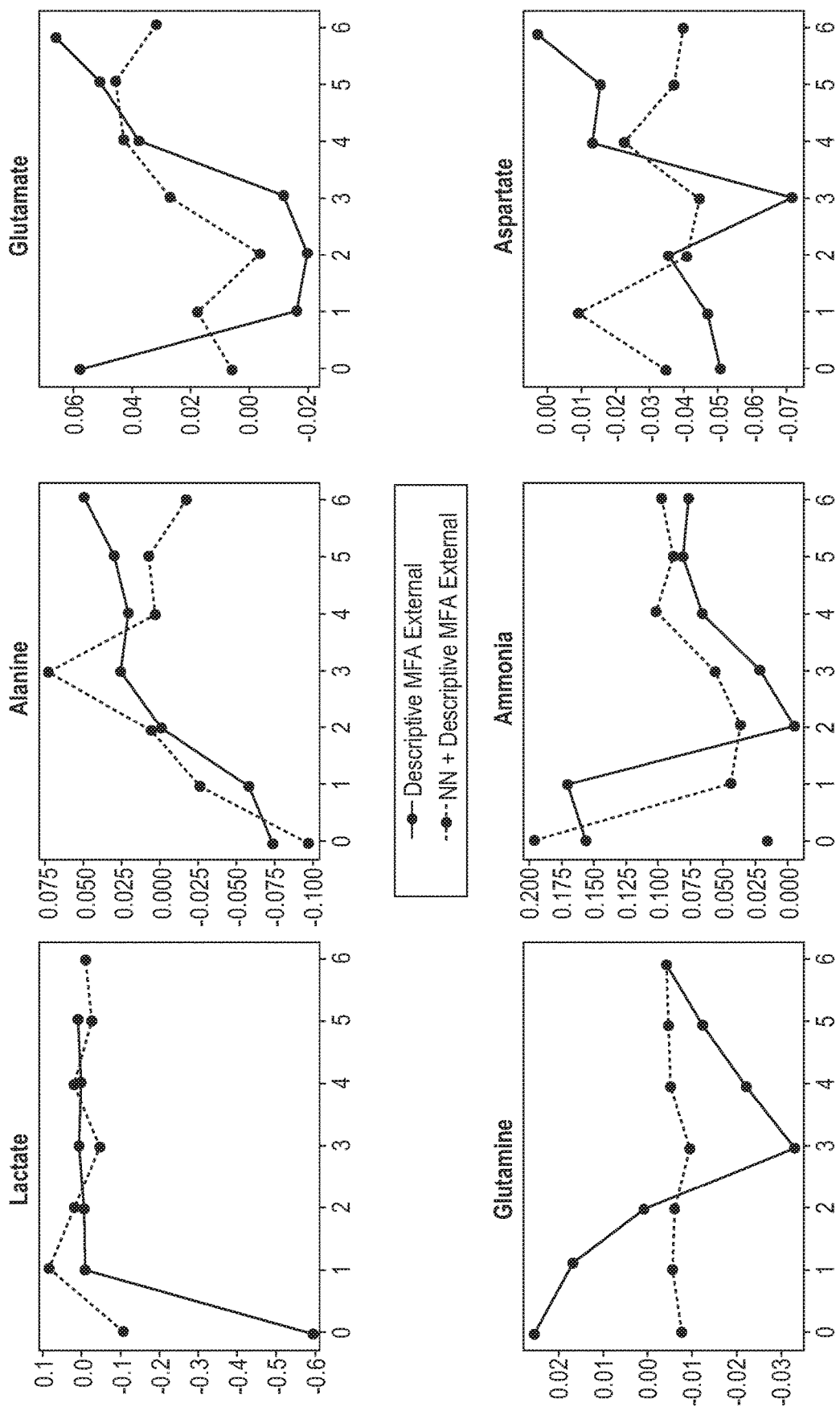
Figure 19B:
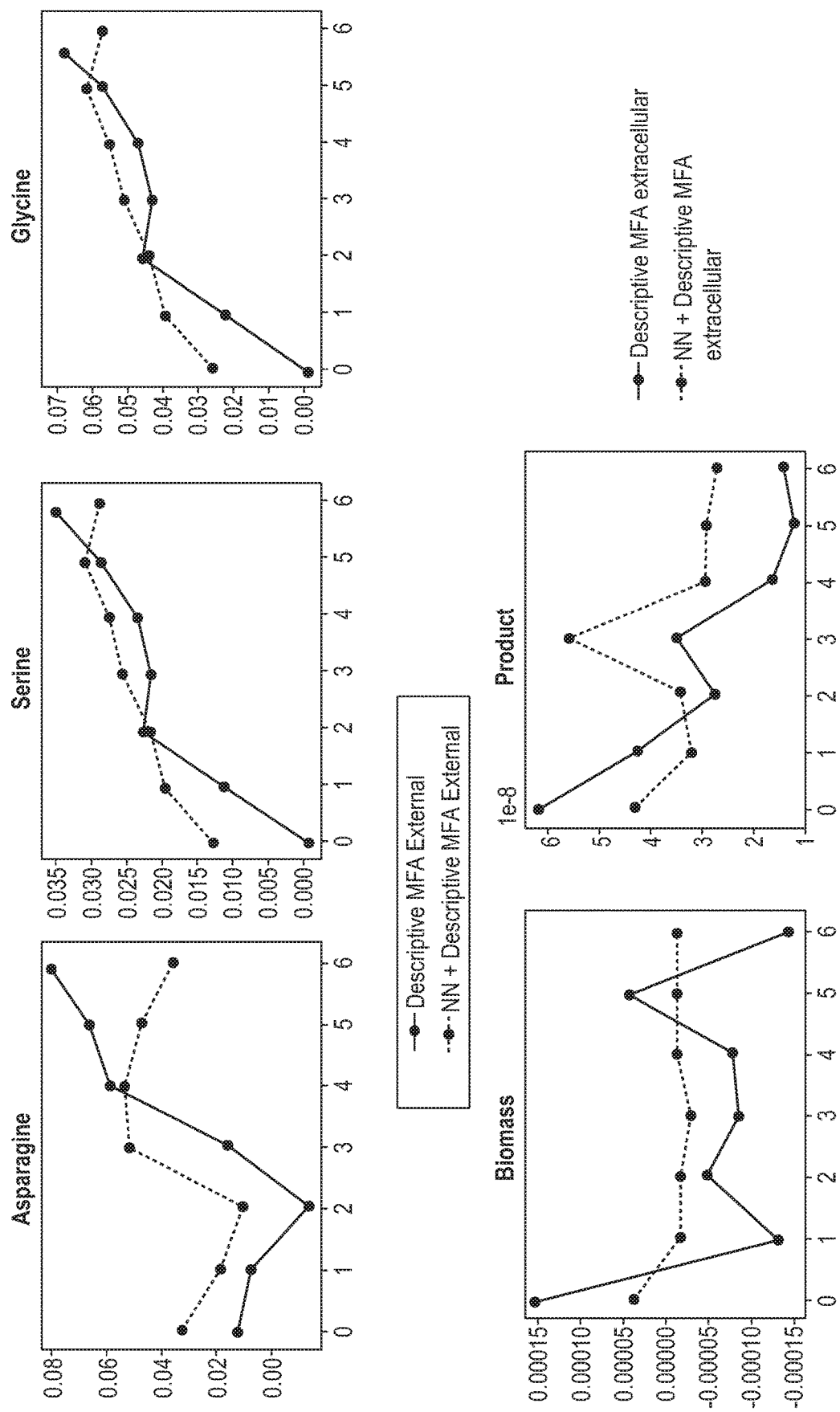
Figure 20A:
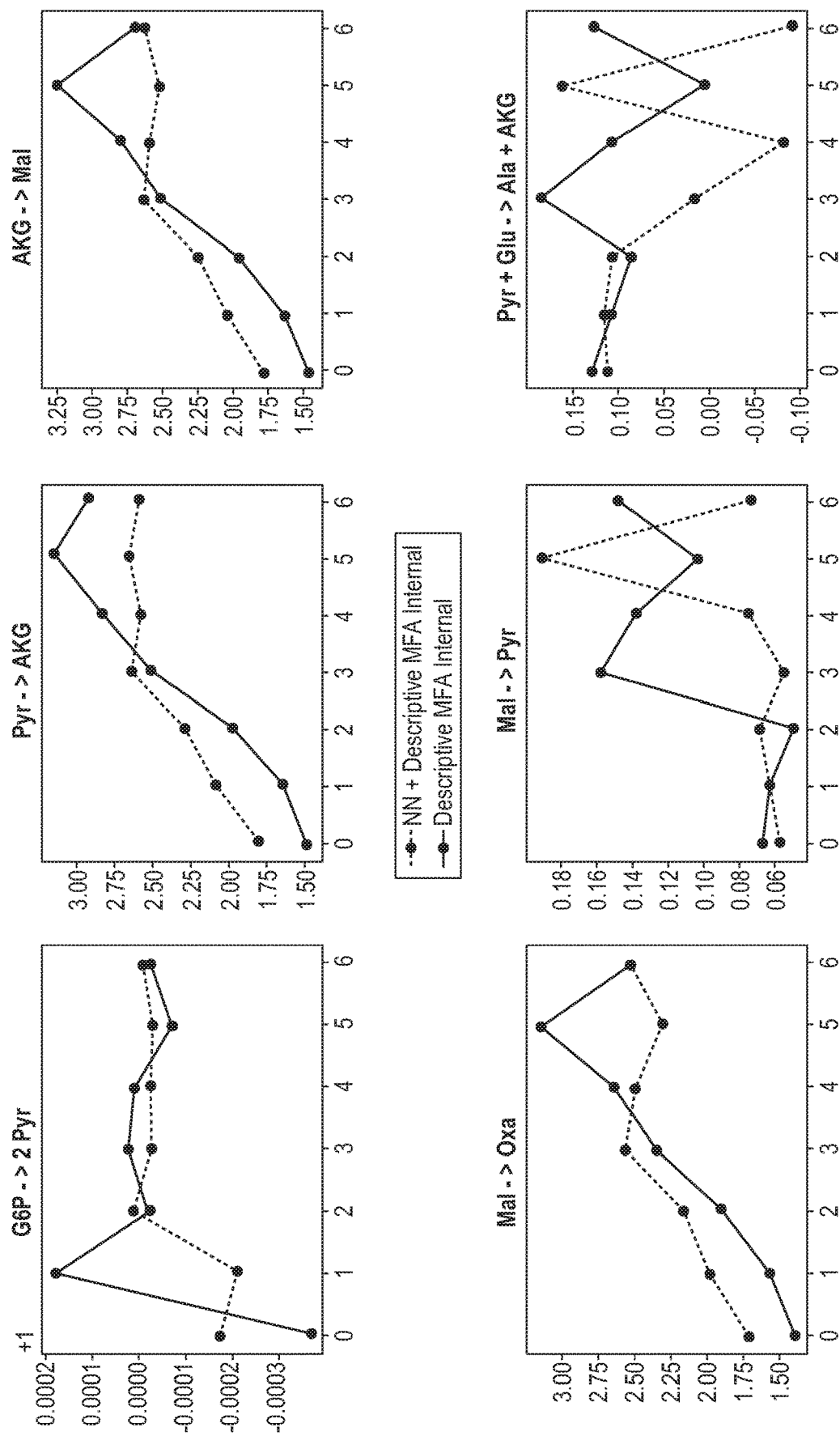
Figure 20B:
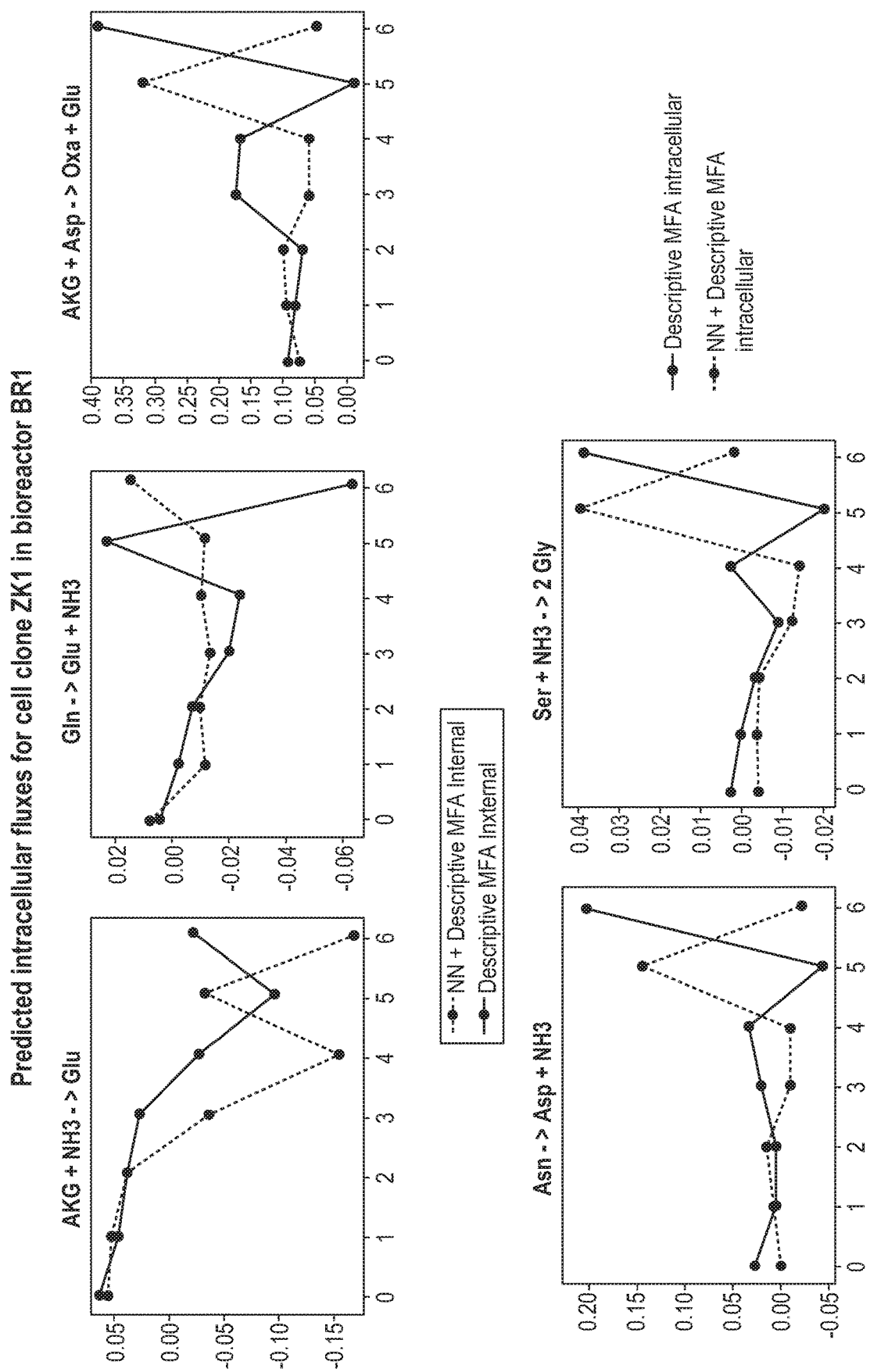
Figure 21B:
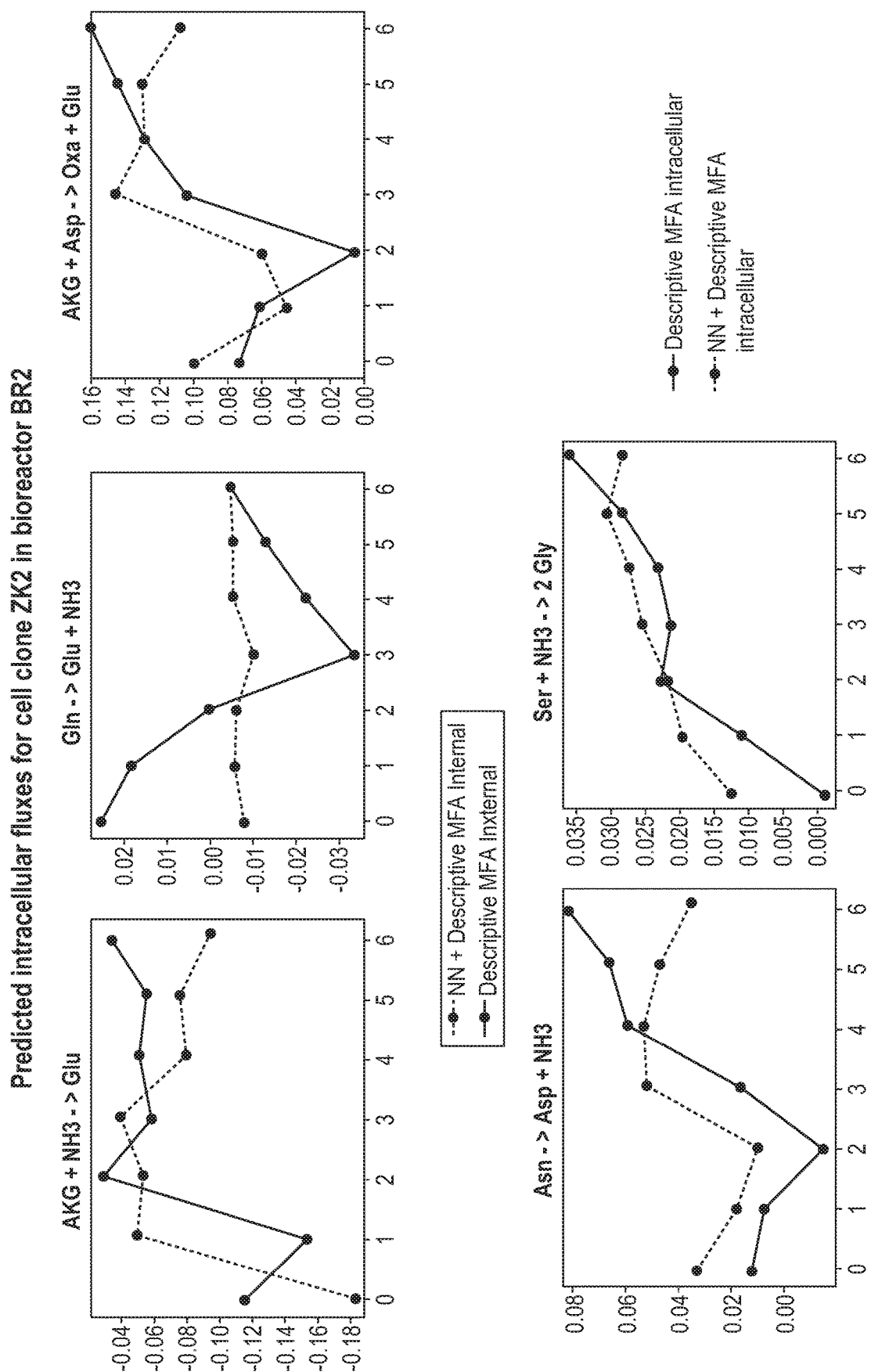

FIGS. 3A and B shows a block diagram of a system for predicting the metabolic state of a cell, which may be used to monitor and/or control one or more bioreactors;

FIGS. 4a and 4b shows a metabolic model of a cell with multiple intracellular and extracellular fluxes of intracellular and extracellular metabolites;

FIG. 5 shows the calculation of intracellular fluxes at several consecutive points in time during the operation of a bioreactor;

FIG. 6 shows fluxes of different metabolites according to the metabolic model shown in FIG. 4;

FIG. 7 shows several metabolite flows illustrating the successful use of the method for generating biological knowledge;

FIG. 8 shows several metabolite flows illustrating the successful use of the method for generating biological knowledge;

FIG. 9 shows plots with lactate fluxes and glutamine concentrations;

FIG. 10 shows time courses of intracellular fluxes;

FIGS. 11A-11D shows several intracellular and extracellular fluxes at different points in time during the cultivation of a cell culture;

FIG. 12 shows the strongly correlated course of intracellular fluxes, which were calculated for the current point in time by descriptive MFA and predicted for a point in time in the future by a combination of the MLP and MFA;

FIG. 13 shows input parameter values and output parameter values of an NN;

FIG. 14 shows a histogram of the obtained RMSE for intracellular fluxes in 12 fed-batch fermentation runs;

FIG. 15 shows a histogram of the obtained RMSE for extracellular fluxes in 12 fed-batch fermentation runs;

FIG. 16 shows 12 plots each with one predicted extracellular metabolite flux and two extracellular metabolite fluxes measured for identical cell clones in two different bioreactors (fed-batch and split batch);

FIG. 17 shows 11 plots, each with two curves, all obtained for a fed batch bioreactor using two different calculation methods;

FIGS. 18A and 18B shows 11 plots, each with two curves of calculated extracellular fluxes of a cell clone ZK1;

FIGS. 19A and 19B shows 11 plots with two curves each of calculated extracellular fluxes of a cell clone ZK2;

FIGS. 20A and 20B shows 11 plots with two curves each of calculated intracellular fluxes of a cell clone ZK1; and FIGS. 21A and 21B shows 11 plots with two curves each of calculated intracellular fluxes of a cell clone ZK1.

Figure 1:
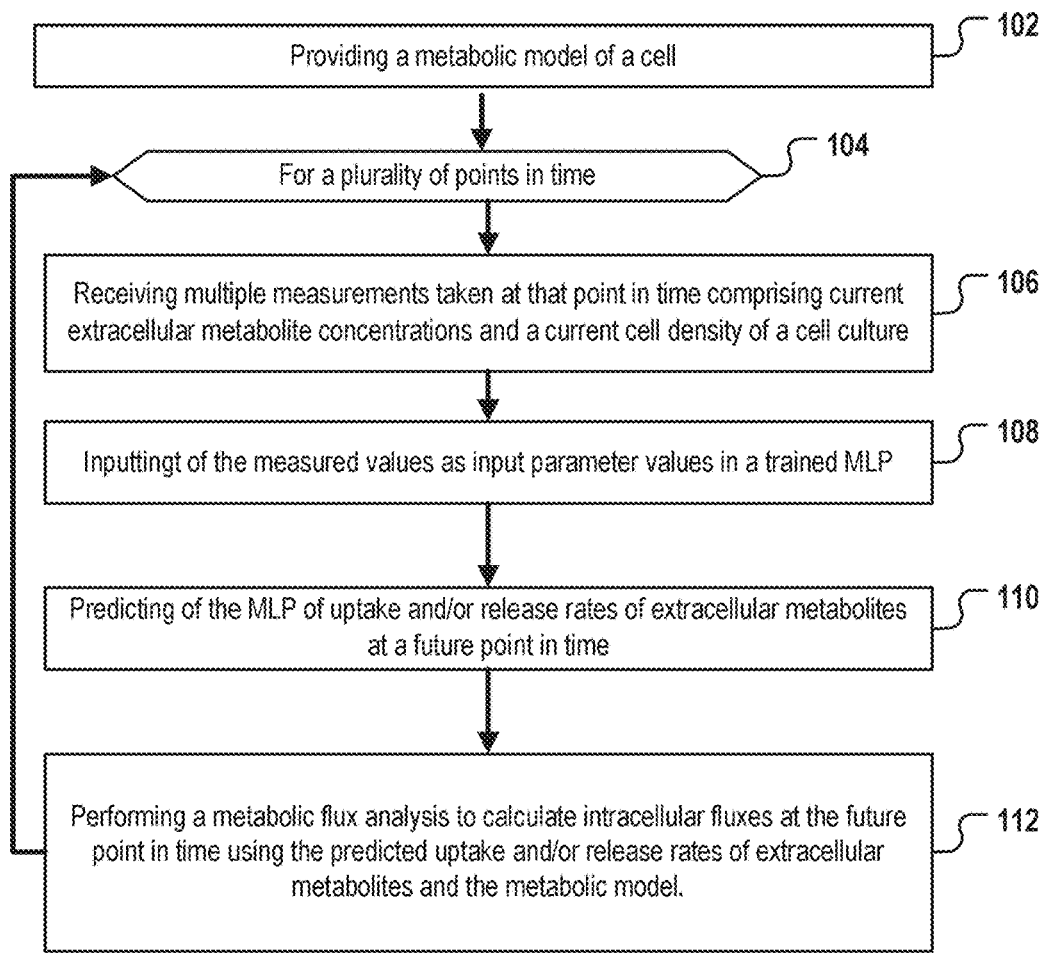
FIG. 1 shows a flow chart of a method for predicting the metabolic state of a cell.

FIG. 1 shows a flow chart of a method for predicting the metabolic state of a cell culture of CHO cells according to an embodiment, which method is equally suitable for other cell types.

Step 102: Model Generation

The processes in a bioreactor can be described mathematically. First of all, the mapping of the temporal changes of relevant substance concentrations or quantities in the reaction medium should be considered (e.g. courses of substrate quantities, product quantities, cell densities). The formulation is based on mass balances and consists of a term that describes the reaction of the substance and a convection term that comprises any material flows into and out of the reactor. It applies in general (see [51], section 4.2 in the Appendix):

$$\text{time-related change in the substance amount of a component in the system} =$$

-continued $$\underbrace{\begin{matrix}\text{component}\\\text{added to}\\\text{the system}\\\text{over time}\end{matrix} - \begin{matrix}\text{amount of the}\\\text{component}\\\text{withdrawn from the}\\\text{system over time}\end{matrix}}_{\text{convection term}} + \underbrace{\begin{matrix}\text{amount of the}\\\text{component}\\\text{converted in the}\\\text{system over time}\end{matrix}}_{\text{reaction term}}$$

or in equations:

$$\frac{dm}{dt} = \dot{V}_{zu} \cdot c_{zu} - \dot{V}_{ab} \cdot c_{ab} + Q, \quad (2.1)$$

wherein m the amount of substance in the reaction medium, t the process time, $\dot{V}_{su}$ or $\dot{V}_{ab}$ the volume flow of the inlet or outlet, $c_{cu}$ or $c_{ab}$ the concentrations of the corresponding substance in the inlet or outlet and Q the amount of substance that is converted per time and volume. In the case that quantities of extracellular metabolites are considered, the reaction term primarily comprises the uptake or release of the substance by the cells. If the cell density in the fermenter is to be described, it includes the formation and death of the cells.

According to embodiments, the metabolic model is based on the assumption according to the above equation that the temporal course of the amount of substance is differentiable. This is justified provided that all incoming and outgoing fluxes are continuous. In the case of bolus feeding or sampling during fermentation, the result is a continuous piece-wise curve. The above equation then applies to the areas between the discontinuities.

On this differential equation numerous mathematical models may be specified for process description, control and optimization. These play an ever-increasing role due to the growing desire to better understand bioprocesses and improve them in silico while saving expensive and time-consuming laboratory experiments. Models that are based only on such mass balances and do not describe intracellular processes are known as black box models. They may not be able to explain dependencies between the considered processes in a mechanistic way. To do so, it would be necessary to model the metabolism as a link between the different extracellular substances.

Ultimately, the metabolic model should enable a metabolic material flow analysis to be carried out, so that the model may be used to draw conclusions from extracellular fluxes to intracellular fluxes. While easy-to-use methods are generally established for determining cell density and measuring extracellular substance concentrations, the observation of intracellular reaction rates is much more complex. To avoid such experiments, metabolic flux analysis (MFA) has been developed—a computational method that may be used to estimate intracellular fluxes from extracellular fluxes. The extracellular material flux describes the amount of material that is absorbed or released by a cell over time. The intracellular material flux is the amount of material that is converted in an intracellular reaction per time and cell.

Thus, in order to be able to perform metabolic material flow analysis, a (preferably or usually simplified) biochemical, stoichiometric metabolic network of the organism under consideration is generated first, which comprises the most important intra- and extracellular reactions. Extracellular reactions are—analogous to fluxes—those in which metabolites are taken up or released by the cell.

It is assumed that the network consists of k reactions of which $k_m$ the results are measurable and therefore known (these are usually the extracellular reactions) and of l intracellular metabolites. The reactions can then be recorded in a stoichiometric matrix $A \in \mathbb{R}^{l \times k}$ in which the stoichiometric coefficients (negative for educts, positive for products of the individual reactions) are entered, with the rows corresponding to the various metabolites and the columns corresponding to the reactions. The extracellular metabolites are omitted. A concrete example is given in section 2 of the Appendix.

The material flux of the j-th reaction is designated with $v_j$. Furthermore, $m_i$ is the amount of the i-th intracellular metabolite in a single cell. If the fluxes and metabolite quantities are combined to vectors v or m, the following applies:

$$\frac{dm}{dt} = Av \quad (2.2)$$

The equation states that the temporal change of metabolite quantities in the cell results from the balancing of incoming and outgoing material flows.

The MFA is then based on the so-called steady-state assumption that the amount of intracellular metabolites remains constant, which means that the sum of the incoming fluxes for each intracellular metabolite equals the sum of the outgoing ones. This simplifies equation (2.2) to $$0 = Av \quad (2.3)$$

Dividing the vector v into the sub-vector $v_m \in \mathbb{R}^{k_m}$ of known (measurable) and the sub-vector $v_u \in \mathbb{R}^{k-k_n}$ of unknown fluxes and the matrix A correspondingly into the submatrices $A_m \in \mathbb{R}^{l \times k_m}$ and $A_u \in \mathbb{R}^{l \times (k-k_n)}$ so that $Av = A_m v_m + A_u v_u$, equation (2.3) becomes $$A_u v_u = -A_m V_m. \quad (2.4)$$

The determination of unknown fluxes $v_u$ by MFA may thus be carried out by solving a linear system of equations.

The next step is to classify the system of equations. The obvious formulation for the solution of the system of equations $$v_u = -A_u^{-1} A_m v_m$$

is usually not applicable, since the matrix $A_u$ is usually not invertible. In such cases the solution space may be infinite or contradictions may occur so that no solution exists. The following terms were introduced by van der Heijden et al. (1994), which classify the system of equations or material fluxes according to criteria of solubility and consistency [17, 39, 40], and which are also used for the generation of the model according to the embodiments of the invention:

Determination: The system (2.4) is under-determined, if $\text{Rang}(A_u) < k - k_m$ is applicable. In this case not all unknown fluxes may be calculated unambiguously, because the metabolic network contains too few restrictions. If $\text{Rang}(A_u) = k - k_m$, then the system has at most one solution and is called determined.

Redundancy: If $\text{Rang}(A_u) < l$, the system is redundant. This means that linearly dependent lines exist in $A_u$. Due to measurement errors in the determination of $v_m$ or inaccuracies in the metabolic network model, this usually leads to an inconsistent system for which no solution exists (it applies then $\text{Rang}(A_u) < \text{Rang}((A_u | -A_m v_m)$, the latter term represents the extended coefficient matrix). If $\text{Rang}(A_u)=1$, the system is not redundant and therefore always consistent.

Calculability: A flux $v_u$ is called calculable if it may be unambiguously calculated using equation (2.4), otherwise it is not calculable. A consistent system is assumed here. If the system is under-determined, there is at least one flux that is not calculable.

Balanceability: A flux $v_m$ is called balanceable if its value has an influence on the consistency of the system, otherwise not balanceable. Balanceable flows only occur in redundant systems.

As mentioned above, MFA systems are often under-determined and/or redundant (although a system may be under-determined and redundant at the same time). A solution can then be formulated using the Moore-Penrose pseudo-inverse $A_u^*$, which is defined for all $A_u$:

$$v_u = -A_u^* A_m v_m. \tag{2.5}$$

In the case of underdeterminedness, this expression yields one of the infinitely many solutions to the system of equations; in the case of inconsistency, it yields a least-squares solution.

In the following, methods will be presented with which it may be checked which of the unknown fluxes are nevertheless calculable in the case of underdetermination, and which of the measured fluxes can be balanced in the case of redundancy.

Identification of Calculable Fluxes

The method for the identification of calculable fluxes published by Klamt et al. is presented [17]. Be $T \in \mathbb{R}^{(k-k_m) \times (k-k_m-\text{Rang}(A_u))}$ a matrix whose columns form a base of the core of $A_u$. Then it applies:

$$A_u T = 0.$$

Each vector $p \in \text{Kern}(A_u)$ can be represented as a linear combination of the base vectors. So there is a $a \in \mathbb{R}^{k-k_m-\text{Rang}(A_u)}$, so that applies $$p = Ta.$$

Equation (2.4) can be extended:

$$A_u v_u = -A_m v_m + A_u Ta,$$

where $a \in \mathbb{R}^{k-k_m-\text{Rang}(A_u)}$ is arbitrary. The left-sided application of the pseudo-inverse then results in $$v_u = -A_u^H A_m v_m + Ta.$$

By variation of the vector a one obtains the space of the solutions of the system of equations (2.4). $\tau$ has a rank greater than 0 exactly if the system is underdetermined. From this it can be concluded that the calculable fluxes $v_u$ are exactly those on which variation of a has no influence. This is exactly the case if the corresponding row in the matrix T is a zero row.

Preferably, according to the embodiments of the invention, the next step is the identification of calculable fluxes.

For a non-redundant system, inserting (2.5) into (2.4) yields the formulation $$R v_m = 0 \tag{2.6}$$

with the redundancy matrix $R := A_m - A_u A_u^\# A_m$ (see references [17, 39] in the appendix).

However, if the system is redundant, equation (2.6) is only fulfilled for determined ones, which is equivalent to the solvability of equation (2.4). The column notation illustrates that a measured flux has no influence on the solvability of equation (2.4) if the corresponding column vector R is of the null vector. $r_j$ denotes in the above formulation the j-th column vector of R and $v_{m,j}$ the j-th measured flux.

In the following, possibilities are presented for treating underdetermined and redundant Treatment of Under-Determined Systems If the system is under-determined, i.e. has an infinite number of solutions, there are several ways to modify the problem in order to arrive at a unique solution. One option would be, if possible, to tighten the resulting restrictions by extending the metabolic network model, thus creating a determined system. Furthermore, one may try to increase the number of known fluxes by additional experimental quantifications. The determination of intracellular fluxes may be achieved by $^{13}C$ labelling experiments (see literature [43] in the appendix).

f one wants to avoid this experimental effort, the widespread method of Flux Balance Analysis (FBA) is a good choice. Here, a target function to be optimised is defined, which is selected according to biological plausibility and which depends on the material fluxes. For example, it can be assumed that the host organisms direct their material fluxes towards maximising their growth rate, as this represents a significant evolutionary advantage. If the target function is designated F, then the FBA results in the general formulation:

$$\max F(v)$$
$$\text{s.t.} \quad Av = 0$$

By formulating it as an optimization problem with equation constraints, a clear flux distribution is usually provided as the solution. If information about irreversibilities of reactions is available, the allowable range (allowable range: set of points for which all constraints of the optimization problem are fulfilled) can be further restricted by the additional inequality conditions $$v_{irrev} \geq 0$$

whereby $v_{irrev}$ is the vector of all irreversible fluxes.

The main problem in FBA is the correct choice of the objective function on which the solution depends. It is quite possible that cells change their biological target during fermentation (see literature [33] in the appendix).

Management of a Redundant System

In the case of a redundant system of equations, there is usually no flux distribution that solves equation (2.4) due to contradictions in the flows that can be balanced. Even in a completely correctly defined network model, inconsistencies usually occur, caused by measurement errors in the determination of $v_m$. The actually measured flow values should be designated in the following as $\bar{v}_m = (\bar{v}_{m,1}, \ldots, \bar{v}_{m,k_m})^T$ in order to clearly distinguish them from the true measurable values. In the literature there are several methods to calculate an approximate solution $\hat{v} = [\hat{v}_m, \hat{v}_u]$ of a redundant MFA problem:

One possibility would be to set $\hat{v}_m = \bar{v}_m$ and select the vector $\hat{v}_u$ so that the mean square distance between the vectors $A_u \hat{v}_u$ and $-A_m \hat{v}_m$ is minimized. The formulation as optimization problem is then $$\min_{v_u} \|A_u v_u + A_m \bar{v}_m\|^2. \tag{2.7}$$

The corresponding solution $\hat{v}_u = -A_u^{\#} A_m \bar{v}_m$ only approximately fulfils the steady-state assumption. If the system is determined, then $A_u^{\#} = (A_u' A_u)^{-2} A_u'$ applies.

A second possibility is the determination of a least-squares solution for the vector v, which minimizes the relative squares distance to the measured fluxes (see literature [39] in the appendix) and fulfills the steady-state condition. The formulation for this is:

$$\min_{v} \frac{1}{2} \sum_{j=1}^{k_m} \left( \frac{v_{m,j} - \bar{v}_{m,j}}{\bar{v}_{m,j}} \right)^2 \quad (2.8)$$
$$\text{s.t. } Av = 0$$

Irreversibilities may also be included as additional constraints.

The second method differs from the first one mainly in that its solution fulfils the steady-state assumption (the measured fluxes are then called balanced). For this, the values of the measurable fluxes in the solution only approximately correspond to the values actually measured. This may be considered reasonable if the steady-state assumption is considered to be more reliable than the measured values for the fluxes, which are always subject to errors. In the solution of (2.8) all those measured fluxes are adjusted which can be balanced. Those that cannot be balanced remain unchanged.

A generalization of the method just described for adjusting balanceable fluxes results from a more statistically motivated approach, which is explained in the literature cited in the appendix [39, 40]. It is based on a weighted least squares approach:

Be $\bar{v}_m$ again the vector of the measured, faulty fluxes and be $v_m$ the vector of the corresponding true values. The measurement error vector $\delta$ denotes the difference between the true and the measured values:

$$\delta := v_m - \bar{v}_m.$$

It is assumed that $\delta$ is to o be normally distributed with expectation vector 0 and covariance matrix $$C_{\bar{v}_m} := \mathbb{E}[\delta \delta^T].$$

Since $v_m$ is unknown, a plausible, experience-based estimate of the covariance matrix must be used for further calculations.

The goal is now an estimate of $v_m$, which fulfills the steady-state assumption and at the same time is close to $\bar{v}_m$, taking into account the information about covariances. This is achieved by using the Mahalanobis distance. The optimization problem for this is:

$$\min_{v_m} \delta^T C_{v_m}^{-1} \delta \quad (2.9)$$
$$\text{s.t. } Rv_m = 0$$
$$\delta = v_m - \bar{v}_m$$

The solution $\hat{v}_m$ of the optimization problem has the form $$\hat{v}_m = (1 - C_{\bar{v}_m} R'^T (R' C_{\bar{v}_m} R'^T)^{-1} R') \bar{v}_m \quad (2.10)$$

(see literature reference [23] according to appendix). I is the unit matrix. R' is the reduced form of R, which is generated by elimination of linear dependent lines and therefore has full rank (this is not unique). It may be generated by multiplication with a non-square matrix $\Gamma$, which carries out the corresponding line transformations:

$$R' = \Gamma R. \quad (2.11)$$

These balanced values may now be used in equation (2.5) to calculate the unknown fluxes.

Assuming that the measurements of the fluxes are independent (i.e. the covariance matrix $C_{\bar{v}_m}$ is diagonal) and the standard deviation of $v_{m,j} - \bar{v}_{m,j}$ is proportional to the magnitude of the measured value $\bar{v}_{m,j}$ with a uniform proportional constant $b > 0$, the optimization problem (2.9) is equivalent to (2.8). It applies:

$$\delta^T C_{v_m}^{-1} \delta =$$

$$(v_m - \bar{v}_m)^T \frac{1}{b^2} \begin{pmatrix} \frac{1}{\bar{v}_{m,1}^2} & & 0 \\ & \ddots & \\ 0 & & \frac{1}{\bar{v}_{m,k_m}^2} \end{pmatrix} (v_m - \bar{v}_m) = \frac{1}{b^2} \sum_{j=1}^{k_m} \left( \frac{v_{m,j} - \bar{v}_{m,j}}{\bar{v}_{m,j}} \right)^2.$$

The formulation (2.9) offers the advantage over (2.8) that the covariance matrix may be flexibly adapted to the quality of the measured data. When balancing fluxes whose measured values are classified as unreliable, this allows greater changes in the values than is the case with presumably more accurately measured fluxes.

Before illustrating the application of MFA in bioprocess engineering issues, the statistical validation of metabolic metabolic models, as carried out according to embodiments of the invention, will first be dealt with in the following section, as this builds on the considerations just explained.

Validation of the Biochemical Metabolic Model

The quality of the postulated biochemical network model has not yet been addressed in the previous remarks. However, it is obvious that an insufficient quality in its formulation may lead to severe deficits in the results of MFA. Validation methods are needed to generate a meaningful model as a compromise between high significance and the greatest possible simplification. In a publication by van der Heijden et al. from 1994, statistically motivated tests are presented and the detection of possible systematic sources of error is explained (see bibliography [40] of the appendix). The investigations are based on the analysis of flows that can be balanced and their influence on inconsistencies in the model. They are therefore only applicable if a redundant system is present.

A Test for the Evaluation of Inconsistencies

In the previous section in equation (2.11) the reduced form R' of the redundancy matrix was already introduced. The residual vector is defined by $$\varepsilon := R' \bar{v}_m.$$

For a redundant system, the following generally applies $\varepsilon \neq 0$. The covariance matrix $C_\varepsilon$ of $\varepsilon$ may be calculated by $$C_\varepsilon := R' C_{\bar{v}_m} R'^T.$$

It is therefore dependent on the covariance matrix of the measured fluxes, which takes into account the uncertainties in the measurements. For the test, the test statistics $H_s$ are used, whose observations are given by:

$$h_s := \varepsilon^T C_\varepsilon^{-1} \varepsilon.$$

It may be shown that the test statistics are subject to a $\chi^2$-distribution (see [40] in the Appendix). The degrees of freedom correspond to the rank of $C_g$.

Overall, the following hypothesis test is obtained:

Test $H_0$: The inconsistency of the considered metabolic model is not significant against $H_1$: The inconsistency of the considered metabolic model is significant:

$$\text{Reject } H_0 \text{ at significance level } \alpha \Leftrightarrow \chi^2_{Rang(C_g), 1-\alpha^*} \quad (2.12)$$

$\chi^2_{Rang(C_g), 1-\alpha^*}$ denotes the $(1-u) \cdot 100\%$-quantile of the $\chi^2$-distribution with $Rang(C_g)$ degrees of freedom.

Detection of Possible, Systematic Sources of Error

If the previously defined test indicates inconsistencies, this may be due to an underestimation of the measurement noise, which is reflected in the matrix $C_{\bar{v}_m}$ and thus influences the outcome of the test. Three further possible sources of error are discussed in the literature [40] of the appendix:

Systematic measurement errors: The measurement of the j-th flux $\bar{v}_{m,j}$ is subject to a systematic error $\pi = \bar{v}_{m,j} - v_{m,j}$.

Absence of an important reaction in the metabolic network: An (k+1)-th important reaction is missing in the network model; the stoichiometric matrix A would have to be extended by another column $a_{k+1}$. The corresponding flux is also indicated as $v_{k+1}$.

Incorrect definition of a reaction in the metabolic network: The j-th reaction is incorrectly defined; the vector $a_j + \Delta a_j$ should be used instead of the column vector $a_j$ in the stoichiometric matrix.

The investigation of the error is based on the structure of the residual vector E: for each of the above errors, a characteristic comparison vector v may be defined, whose direction is approximately the same as the direction of $\varepsilon$, provided that the source of the error is actually present. A statistical test which evaluates the similarity between the directions of the vectors is also presented. The length of $\varepsilon$ gives an indication of the size of the error s. In the following table the corresponding comparison vectors are listed. $r_j'$ denotes here the j-th column vector of R'. The derivation of the comparison vectors shall be demonstrated here only for the first of the listed error sources. For the further cases please refer to [40].

The following applies $$r_1' \bar{v}_{m,1} + r_2' \bar{v}_{m,2} + \ldots + r_{k_m}' \bar{v}_{m,k_m} = \varepsilon.$$

n case of a correctly defined network model, the following applies $\mathbb{E}[\varepsilon] - 0$. If the true value for the j-th flux differs from the measured one by the systematic error $\pi$, i.e.

$$v_{m,j} = \bar{v}_{m,j} \pi,$$

then $$\mathbb{E}[\varepsilon] = E[r_1' \bar{v}_{m,1} + r_2' \bar{v}_{m,2} + \ldots + r_j'(v_{m,j} + \pi) + \ldots + r_{k_m}' \bar{v}_{m,k_m}] =$$
$$\mathbb{E}[r_1' \bar{v}_{m,1} + r_2' \bar{v}_{m,2} + \ldots + r_j' v_{m,j} + \ldots + r_{k_m}' \bar{v}_{m,k_m}] + \mathbb{E}[r_j' \pi] = r_j' \pi.$$

It is therefore to be expected that $\varepsilon$ and $r_j'$ have the same directions.

TABLE 1

Comparison vectors and associated error sizes for three different error sources.

| Error source | Comparison vector r υ | Error size s |
|---|---|---|
| Measurement of the j-th flux $\bar{v}_{m,j}$ is false | $r_j'$ | $\pi$ |
| One (k + 1)-th reaction is missing | $\Gamma(A_u A_u^{\#} - 1)a_{k+1}$ | $v_{k+1}$ |
| The j-th reaction is defined incorrectly | $\Gamma(A_u A_u^{\#} - 1)\Delta a_j$ | $v_j$ |

To assess the similarity between $\varepsilon$ and $\upsilon$, the test statistics $$\Delta^2 = \varepsilon^T C_\varepsilon^{-1} \varepsilon - \frac{(\varepsilon^T C_\varepsilon^{-1} v)^2}{v^T C_\varepsilon^{-1} v}$$

are used, which are $\chi^2$-distributed with a degree of freedom of $Rang(C_s)-1$.

The following hypothesis test assesses the similarity of $\varepsilon$ and $\upsilon$:

Test $H_0$: The vectors $\varepsilon$ and $\upsilon$ are similar against $H_1$: The vectors are not similar:

$$\text{Reject } H_0 \text{ at significance level}$$
$$\alpha \Leftrightarrow \Delta^2 \geq \chi^2_{Rang(C_g)-1, 1-\alpha'} \quad (2.13)$$

The statistical derivation can be found in the appendix of reference [40].

According to embodiments, the metabolic model generated according to embodiments of the invention comprises a network, which should comprise the central intracellular material fluxes and yet have a complexity as low as possible. The model explained here as an example is essentially based on the network stoichiometries proposed in the following publications: Altamirano C, Illanes A, Becerra S, Cairo J J, Godia F (2006): "Considerations on the lactate consumption by CHO cells in the presence of galactose", Journal of Biotechnology 125, 547-556; Llaneras F, Pico J (2007): "A procedure for the estimation over time of metabolic fluxes in scenarios where measurements are uncertain and/or insufficient", BMC Bioinformatics 8:421; and Nolan R P, Lee K (2011): "Dynamic model of CHO cell metabolism", Metabolic Engineering 13, 108-124.

Compartments of the cells were not considered, however. Due to their large number, not all reactions involving redox and energy equivalents may be included in the metabolic model. Therefore, NAD(P)H and ATP were not included in the formulation of the stoichiometry. In addition, some metabolic branches were not considered in detail but were integrated into the biomass formation (e.g. the pentose phosphate pathway). In most cases, the formulated reactions are a summary of several successive biochemical reactions without branches, which should have identical material fluxes according to the steady-state assumption (for example, only a few intermediates of glycolysis or the citrate cycle are explicitly listed).

The biomass balance was taken from the above mentioned publication by Nolan (2011), as well as the conversion of the live and total cell density into the unit mol/l. The formulation of stoichiometry for product formation follows from the amino acid composition of the target protein. The above mentioned publications were also used to determine the reversibility of the reactions.

The resulting metabolic model is shown in detail in FIG. 4. This shows in FIG. 4a a biochemical network model of intra- and extracellular material fluxes of CHO cells]{Biochemical network model of intra- and extracellular material fluxes of CHO cells It models the central fluxes of metabolism, which are the transport and conversion of glucose (Glc), lactate (Lac), alanine (Ala), glutamate (Glu), glutamine (Gln), ammonia (NH3), aspartate (Asp), comprise asparagine (Asn), serine (Ser), glycine (Gly), total cell density (BIO), product (Prod), glucose-6-phosphate (G6P), pyruvate (Pyr), alpha-ketoglutarate (AKG), malate (Mal) and oxaloacetate (Oxa) Reversibility is indicated by the shape of the arrows.

The table in FIG. 4b lists the individual stoichiometric reactions of the metabolic model. Of these, reactions 1, 3, 9, 11, 13, 14, 16, 18, 20, 21, 22 and 23 are extracellular. The model comprises 13 intracellular metabolites for which the steady-state assumption is to apply. The index "e" here refers to extracellular substances. The reversibility/reversibility of reactions is indicated by the reaction arrow.

The network model contained in the metabolic model should comprise the central intracellular material fluxes and yet be as simple as possible. The formulation chosen in this thesis is essentially based on the network stoichiometries proposed in the above mentioned publications by Altamirano et al (2006), Llaneras et al (2007) and Nolan et al (2011). Compartments of the cells were not considered, however. Due to their large number, not all reactions involving redox and energy equivalents may be included in the metabolic model. Therefore, NAD(P)H and ATP were not included in the formulation of the stoichiometry. In addition, some metabolic branches were not considered in detail but were integrated into the biomass formation (e.g. the pentose phosphate pathway). In most cases, the formulated reactions are a summary of several successive biochemical reactions without branches, which should have identical material fluxes according to the steady-state assumption (for example, only a few intermediates of glycolysis or the citrate cycle are explicitly listed).

The biomass balance was taken from the above mentioned publication by Nolan (2011), as well as the conversion of the live and total cell density into the unit mol/l.

The formulation of stoichiometry for product formation follows from the amino acid composition of the target protein.

The above-mentioned publications were also consulted regarding the reversibility of the reactions.

The stoichiometric matrix A was formulated for the metabolic network shown in the table above. The columns corresponding to the known (in this case extracellular) material fluxes were combined to form the submatrix $A_m$, the others to the submatrix $A_v$.

The characterization of the metabolic network may be carried out according to a scheme which is shown and explained in the appendix as FIG. 4.2.

The metabolic network may be validated and, if necessary, modified as described in the appendix.

Thus, a metabolic model 402 of CHO cells has been provided as shown in FIG. 4. The metabolic model includes a variety of intracellular 410 and extracellular 408 fluxes, and the metabolic model specifies at least one stoichiometric relationship between an intracellular 406 and an extracellular 404 metabolite.

The following steps 106-112 are performed for a plurality of points in time during the cultivation of a cell culture in a bioreactor. A profile of actually measured extracellular material fluxes and extracellular fluxes predicted for the next point in time (after an interval of defined length, e.g. 24h) may be generated. The deviation of these two profiles from each other indicates the quality of the prediction.

Step 106: Receiving Measured Values

Figure 2:
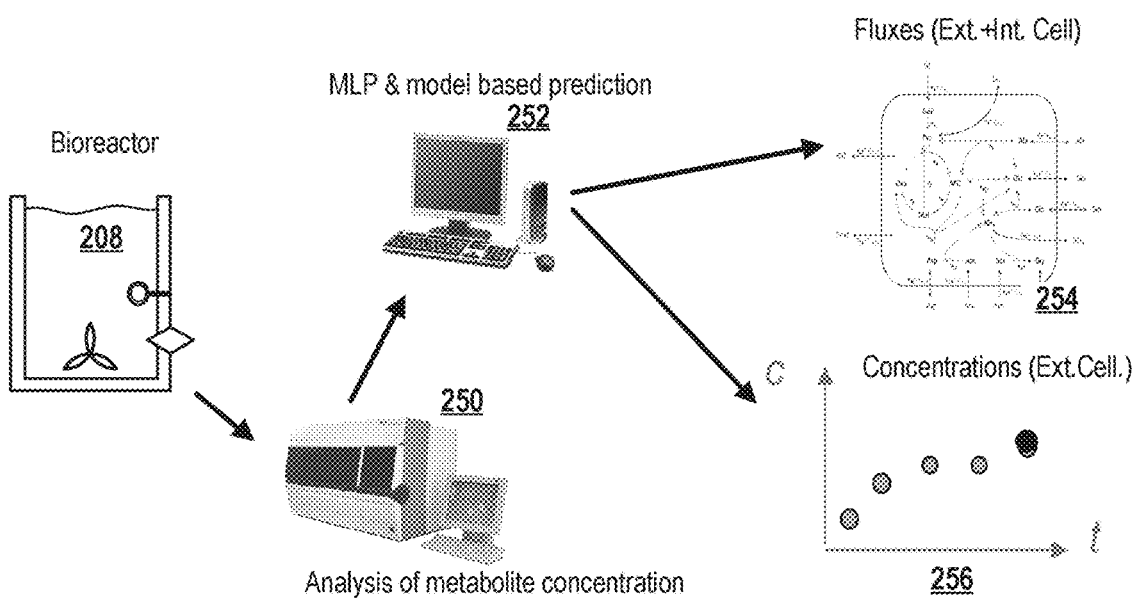
FIG. 2 shows an example of the process of obtaining information in several stages using different devices and data sources.

In one embodiment, a sample is taken at several points in time during the cultivation of a cell culture in a bioreactor 208 of that cell culture and transferred automatically or manually to one or more analysing devices 250 as shown in FIG. 2. The analysing device may be a system of one or more analysers, for example a Thomas chamber or an optical counting station for determining cell density. For example, a high performance liquid chromatograph or other suitable methods known in the state of the art may be used to determine the concentration of individual amino acids. Samples may be taken, for example, at 24-hour intervals. The measured data obtained in this way are transmitted to a data processing system 252. The data processing system 252 may, for example, be a computer which, as a control unit, monitors and/or controls one or more bioreactors.

According to some embodiments, at least some of the measured values, for example the cell density, are also determined by corresponding sensors of the bioreactor 208 itself and transmitted to a data processing system 252.

In addition to the concentrations of selected extracellular metabolites which are known or expected to have a certain predictive power with respect to the concentration and flux of this or another extracellular metabolite at a future point in time, other input parameter values may also be determined, in particular the current time, the current cell density, and, if appropriate, other parameters such as the LDH concentration, which may be used as a correction factor for the lysed cells not included in the cell density determination. The measured data thus obtained empirically at a determined point in time may now be used for the predictions of extracellular fluxes at a subsequent point in time, for example the next day, by means of an MLP, as described in the following step.

Step 108: Input of the Measured Values into a Trained MLP

The data processing system 252 includes an MLP, for example a neural network (NN) or a cooperating system of several neural networks, which has been trained to predict or estimate one or more extracellular fluxes of the metabolic model 254 on the basis of input parameter values (in particular concentrations of extracellular metabolites and cell density) measured at a determined point in time. For example, the data processing system 252 may include a program logic which automatically transfers the measured data obtained at a point in time as input to an MLP trained on test data sets obtained from cell cultures of the same type of cells as the cells of the cell culture whose metabolic state is to be predicted at a future point in time (for example, next day).

Step 110: Predictions of the MLP's Future Intake and Release Rates

Using the neural network, extracellular fluxes are predicted or estimated in a one-step-prediction based on currently measured concentrations of extracellular metabolites $\bar{c}_{m,j}^{(n)}$ at the point in time $t^{(n)}$ at a future point in time $t^{(n+1)}$ chosen at will. Thus, in this step, in response to the input of the measured input parameter values into the MLP, the MLP calculates and returns one or more extracellular fluxes for the future point in time.

Optional: Predictions of the MLP of Concentrations of Extracellular Metabolites

The extracellular fluxes estimated via the neural network are, according to embodiments of the invention, also used for one-step predictions of metabolite concentrations at an arbitrarily chosen future point in time $t_{(n+1)}$ based on the current concentrations $\bar{c}_{m,j}^{(n)}$ at that point in time $t^{(n)}$.

For this purpose, equation (4.1) of the appendix is solved according to c2. Since the live cell density at the future point in time $VCD^{(n+1)}$ is unknown, it is replaced by the currently measured and, if necessary, corrected cell density. The reformulated equation is:

$$\tilde{c}_{m,j}^{(n+1)} = \tilde{v}_{m,j}^{(n)}(t^{(n+1)} - t^{(n)}) \frac{VCD^{(n)}(V^{(n)} + V^{(n+1)})}{2V(n+1)} + \frac{\bar{c}_{m,j}^{(n)} V^{(n)} + c_{zu_{m,j}}^{(n)} V_{zu}^{(n)}}{V^{(n+1)}}. \quad (4.4)$$

If feedings are carried out during the operation of the bioreactor, they should preferably be considered in $c_{xu_{m,j}}^{(n)}$, $V_{su}^{(n)}$ and $V^{(n+1)}$.

Step 112: Implementation of a MFA

Based on the uptake and release rates of the extracellular metabolites (extracellular fluxes) as predicted by the MLP for the future point in time, a metabolic flux analysis is then carried out in accordance with the embodiments of the invention, which also incorporates the intracellular fluxes and stoichiometric equations as formulated in the metabolic model. Since in the metabolic model extracellular and intracellular fluxes are coupled to each other via one or more intracellular metabolites, it is mathematically possible to also predict the intracellular fluxes at the future point in time on the basis of the predicted extracellular fluxes. Corresponding program routines for performing metabolic flux analysis can be implemented in Matlab and other software solutions available on the market.

Since the predictions of the intracellular fluxes include both the predictions of the MLP trained on dynamic, empirical data and the knowledge of stoichiometric relationships and reaction equations specified in the metabolic model, this prediction step may also be described as a prediction of a hybrid model relationship.

For example, the coupling of the results of the predictions of the MLP with the information of the metabolic model in the course of material flow analysis may be implemented as follows After the prediction of the extracellular fluxes in the following time interval using the neural network, a metabolic material flow analysis is performed to estimate the flux distribution in the next time interval.

First, an estimate of a covariance matrix of the fluxes of the metabolic model is generated:

$$C_{\tilde{v}m} = \mathbb{E}[(v_m - \check{v}_m)(v_m - \check{v}_m)^T]$$

The Formulation $$\mathbb{E}\left[(v_m - \check{v}_m)(v_m - \check{v}_m)^T\right]$$
$$= \mathbb{E}\left[(v_m - \bar{v}_m + \bar{v}_m - \check{v}_m)(v_m - \bar{v}_m + \bar{v}_m - \check{v}_m)^T\right]$$
$$= \underbrace{\mathbb{E}\left[(v_m - \bar{v}_m)(v_m - \bar{v}_m)^T\right]}_{=C_{\check{v}_m}} - 2\mathbb{E}\left[(v_m - \bar{v}_m)(\check{v}_m - \bar{v}_m)^T\right] + \mathbb{E}\left[(\bar{v}_m - \check{v}_m)(\bar{v}_m - \check{v}_m)^T\right]$$

shows, that both the quality of the measurements and the quality of the estimates of the measured values by the neural network are incorporated into the covariance matrix. However, the rewording may not facilitate the estimation, since the differences $(v_m - \bar{v}_m)$ and $(\hat{v}_m - \bar{v}_m)$ do not represent independent random variables and the expected value in the middle term of the right side and thus the expected value in the middle term of the right side is unknown. Therefore, the expression used in this paper according to Equation 4.5 in the Appendix, which will be explained in the following, is only a rough approximation of the actual covariance matrix.

According to embodiments, the covariance matrix is chosen as a diagonal matrix for the purpose of predicting future intracellular fluxes, since the different metabolite fluxes are estimated over separate networks and the errors may therefore be considered largely independent of each other. By definition, the diagonal entries should reflect, or at least be proportional to, the variations in the errors of the estimated fluxes (the proportionality factor does not play a role in solving the MFA problem as shown in Equation 2.9 of the Appendix).

In contrast, according to embodiments of the invention for descriptive metabolic material flow analysis of the current metabolic state of a cell, a covariance matrix $C_{v_m}$ is used in which the diagonal entries are not dependent on the amount of fluxes.

Be $\check{v}_{m,j}^{(n)}$ the j-th measured predictive flux in the n-th time interval. The covariance matrix was formulated as a diagonal matrix and has the structure:

$$C_{\check{v}_m} = \begin{pmatrix} \psi_1 & & 0 \\ & \ddots & \\ 0 & & \psi_{k_m} \end{pmatrix}. \quad (4.5)$$

The diagonal $\psi_j$ entries were chosen as the medians of the quantities $$\{(\bar{v}_{m,j}^{(n)} - \check{v}_{m,j}^{(n)})^2 \ln \text{Zeitinterval in Trainigsdatenisatz}\} \quad (4.6)$$

In this embodiment it is assumed that the "time interval in the training data set" is identical or similar to the time interval to be used for the current prediction.

A flow analysis is then performed on the basis of this covariance matrix as is known per se in the state of the art. The covariance matrix is used to balance the fluxes according to equation (2.10) of the appendix. Equation 2.10 of the Appendix refers to the descriptive MFA, where a different covariance matrix was used according to the embodiment described in the Appendix. However, the balancing or calculation of the fluxes by MFA is done in the same way in the case of predictive MFA.

Optionally, an error analysis of the model based e.g. on a Gaussian error propagation may be performed as described in section 4.7.8 of the Appendix.

Generation and Training of a Neural Network

Compared to the specification of reaction-kinetic models for the prediction of future material fluxes, the use of trained MLPs has the advantage that their generation is usually easier and faster in a semi-automatic method. An example of how an MLP in the form of an NN may be generated by training is described below.

a) Cultivation of Several Training Cell Cultures

In order to obtain the broadest possible database for MLP training, several training cultures are preferably cultivated in several bioreactors. Preferably, these bioreactors comprise one or more fed-batch reactors and one or more additional bioreactors from other reactor types.

Eight fermentations of a clone of recombinant CHO-cells in an embodiment have been carried out on a one-litre scale. The initial conditions (volume, media composition, inoculum concentration) were chosen identically for each bioreactor, but different operation modes were used:

A bioreactor was operated in a batch mode until the viability of the cells dropped below 50%.

In a second bioreactor, the batch method was also used initially. Towards the end of the exponential growth phase, a partial harvest was carried out and the reactor was filled up with fresh medium, so that conditions similar to those at the beginning of the fermentation were achieved (in terms of volume and inoculum concentration). Subsequently, the batch method was continued (so-called split-batch method).

The fermentation in the remaining six reactors was carried out as a fed-batch with an initial batch phase. Both continuous feeding and a pulse-like nutrient addition took place towards the end of the fermentation. The fed-batch fermentations differed in the glucose concentrations in the medium, which were adjusted by different feeding strategies. In the following explanations, the fed-batch approaches will often be numbered. According to this numbering, in the first two approaches a short term complete glucose limitation took place in the second half of the process before the bolus additions were made. The third and fourth approaches had the same limitation, but the subsequent boluses set higher glucose concentrations. In the fifth and sixth approaches there was always a positive minimum glucose concentration.

Temperature, pO2 value and pH value were kept constant during the entire fermentation. Regular sampling was carried out throughout the process. The samples were examined with regard to their live and total cell density, using a staining method that distinguishes between living and dead cells. Lysed cells were not recorded. In addition, the content of various substances in the reaction medium was examined using a COBAS INTEGRA analyzing device or high-performance liquid chromatography. These included glucose, lactate and ammonium as well as the amino acids alanine, glutamine, glutamate, asparagine, aspartate, serine, glycine and the enzyme lactate dehydrogenase. The product concentration was also determined.

At the sampling points, the volume of liquid in the bioreactor was measured using a fermenter scale.

b) Determination of the Network Architecture

A neural network was generated which was to estimate the mean fluxes of extracellular metabolites between the current and the next sampling time from the current state in the bioreactor (so-called one-step prediction). According to some embodiments, a separate network was trained for each extracellular material flux as an output variable. A selection of the currently prevailing extracellular metabolite concentrations served as input variables.

The neural network consisted of a two-layer perceptron with linear activation function in the output layer and sigmoidal activation function in the hidden layer (see Figure 2.4 in the appendix). For the latter, both the sigmoid function and the hyperbolic tangent were tested. There were no significant differences to the results obtained using the sigmoid function. The training was performed according to the sequential gradient descent method (as exemplified in equations (2.16), (2.17) and (2.18) in the appendix).

c) Selection of Input Variables

According to preferred embodiments of the invention, several or all extracellular metabolites mentioned in the metabolic model are sorted according to their relevance for the prediction of the respective flux in order to select the input parameter values. Preferably, extracellular metabolites with redundant information content were not considered.

A detailed description for the selection of the input parameter values according to the embodiments of the invention is given in the description of FIG. 13.

d) Selection of Training Parameters, Initialization of Weights and Normalization of Data After the number of iterations and hidden neurons has been determined, the values $\eta=0.1$ in the output layer and $\eta=0.02$ in the hidden layer are now selected for the initial learning step in each net. After each tenth of the total number of iterations, the step sizes are reduced by $1/10$ of the initial value. Initial values for the weights were generated to $[-1/10, 1/10]$ equally distributed random numbers. The input and output training data were standardized separately by metabolite so that the adjusted values had the empirical mean 0 and the empirical standard deviation 0.5.

The test data were transformed in the same way with the mean values and standard deviations of the training data set.

e) Selection of Training and Test Data Sets

The estimates were made by three different neural networks, which differ in the grouping of the data into training and test data sets:

1. network 1: The training data set of the first network consisted of the data from three of the fed-batch fermentations and the batch fermentation, the test data set consisted of the data from the other three fed-batch fermentations and the split-batch fermentation.
2. network 2: The second network had data from three of the fed-batch fermentations in the training data set and the data from the remaining three of the fed-batch fermentations, batch fermentation and split-batch fermentation in the test data set.
3. network 3: The training data set of the third network comprised the data from three of the fed-batch fermentations and the test data set comprised the data from the remaining three fed-batch fermentations.

f) One-Step Prediction of Extracellular Metabolite Concentrations

The goal is the generation of a trained MLP, which allows the most accurate predictions of the metabolism of a cell.

If low-frequency data is generated during the generation of the training data set, it may happen that averaging/filtering of the data would lead to a too large loss of information. Therefore, in this case, mean extracellular fluxes between two consecutive measurement points should be approximated. The calculation is based on equation $$\dot{m} = \dot{V}_{zu} \cdot c_{zu} - \dot{V}_{ab} \cdot c_{ab} + Q$$

and will be explained in the following:

Since the batch and the fed-batch method are to be considered and there is therefore no liquid discharge, the following applies in any case $\dot{V}_{ab}=0$. The extracellular flux v of a component at time t is, as already mentioned in section 2.2.2 of the Appendix, the amount of substance that is absorbed or released by a cell per time. It is therefore given by $$v(t) := \frac{Q(t)}{VC(t)}$$

where VC(t) is the number of living cells in the reaction medium at time t. According to equation 2.1 in the appendix, the following therefore applies in the area between two discontinuities $$\upsilon(t) = \frac{\dot{m}(t) - \dot{V}_{zu}(t) \cdot c_{zu}}{VC(t)}.$$

The concentration of the substance in the feed $c_{zu}$ is constant over time or is assumed to be approximately constant.

Unsteadiness may occur at the sampling times, and during bolus additions.

Initially it should be assumed that the addition of nutrients is always continuous and that therefore the quantities m and $V_{zu}$ can be differentiated between two measuring points. If one wants to determine the mean flux $\upsilon_{avg}$ between two consecutive measuring points t1 and t2, one may estimate it—at first seemingly trivial—by:

$$\upsilon_{avg} = \frac{\frac{\Delta m}{\Delta t} - \frac{\Delta V}{\Delta t} c_{zu}}{VC_{avg}} = \tag{4.1}$$

$$\frac{m_2 - m_1 - m_{zu}}{(t_2 - t_1)\frac{VC_1 + VC_2}{2}} = \frac{c_2 V_2 - c_1 V_1 - c_{zu} V_{zu}}{(t_2 - t_1)\frac{VCD_1 V_1 + VCD_2 V_2}{2}}$$

Here, the indexed variables denote the value at point in time t1 or t2, $m_{zu}$ is the amount of substance that is fed into the reaction medium via the feed in the considered time interval and VCD denotes the living cell density. The operator $\Delta$ symbolizes the difference of the corresponding quantities between t1 and t2.

The above estimation (4.1) shall be mathematically substantiated in the following. It is obtained by integration over the time interval $(t_1, t_2)$, whereby the individual measured quantities are linearly interpolated between the two sampling times, and by additional Taylor development:

With linear interpolation, the following applies to all $t \in (t_1, t_2)$:

$$\dot{m}(t) = \frac{m_2 - m_1}{t_2 - t_1}$$

-continued $$\dot{V}_{zu} = \frac{V_2 - V_1}{t_2 - t_1}$$

$$VC(t) = VC_1 + (VC_2 - VC_1)\frac{t - t_1}{t_2 - t_1} = \frac{(t_2 - t)VC_1 + (t - t_1)VC_2}{t_2 - t_1}.$$

Therefore $$\upsilon_{avg} = \frac{1}{t_2 - t_1} \int_{t_1}^{t_2} \frac{Q(t)}{VC(t)} dt$$

$$= \frac{1}{t_2 - t_1} \int_{t_1}^{t_2} \frac{\dot{m}(t) - \dot{V}_{zu}(t) \cdot c_{zu}}{VC(t)} dt$$

$$= \frac{1}{t_2 - t_1} \int_{t_1}^{t_2} \frac{\frac{m_2 - m_1}{t_2 - t_1} - c_{zu}\frac{V_2 - V_1}{t_2 - t_1}}{VC(t)} dt$$

$$= \frac{m_2 - m_1 - c_{zu}(V_2 - V_1)}{t_2 - t_1} \cdot \frac{1}{t_2 - t_1} \int_{t_1}^{t_2} \frac{1}{VC(t)} dt$$

$$= \frac{m_2 - m_1 - m_{zu}}{t_2 - t_1} \cdot \frac{1}{t_2 - t_1} \int_{t_1}^{t_2} \frac{1}{VC(t)} dt$$

The following applies to the remaining integral:

$$\frac{1}{t_2 - t_1} \int_{t_1}^{t_2} \frac{1}{VC(t)} dt = \int_{t_1}^{t_2} \frac{1}{(t_2 - t)VC_1 + (t - t_1)VC_2} dt$$

$$= \int_{t_1}^{t_2} \frac{1}{t_2 VC_1 - t_1 VC_2 + t(VC_2 - VC_1)} dt$$

$$= \frac{1}{VC_2 - VC_1} [\ln|t_2 VC_1 - t_1 VC_2 + t(VC_2 - VC_1)|]_{t_1}^{t_2}$$

$$= \frac{\ln((t_2 - t_1)VC_2) - \ln((t_2 - t_1)VC_1)}{VC_2 - VC_1}$$

$$= \frac{\ln(VC_2) - \ln(VC_1)}{VC_2 - VC_1}$$

A Taylor expansion of the logarithms by $$\frac{VC_1 + VC_2}{2}$$

up to the first order is performed, which results in:

$$\frac{\ln(VC_2) - \ln(VC_1)}{VC_2 - VC_1} = \frac{\ln\left(\frac{VC_1 + VC_2}{2} + \frac{VC_2 - VC_1}{2}\right) - \ln\left(\frac{VC_1 + VC_2}{2} + \frac{VC_1 - VC_2}{2}\right)}{VC_1 - VC_2}$$

$$\approx \frac{\ln\left(\frac{VC_1 + VC_2}{2}\right) + \frac{VC_2 - VC_1}{2}\frac{2}{VC_1 + VC_2} - \ln\left(\frac{VC_1 + VC_2}{2}\right) - \frac{VC_1 - VC_2}{2}\frac{2}{VC_1 + VC_2}}{VC_1 - VC_2}$$

$$= \frac{\frac{2VC_2 - 2VC_1}{VC_1 + VC_2}}{VC_1 - VC_2}$$

$$= \frac{1}{\frac{VC_1 + VC_2}{2}}$$

Using this expression for the above integral gives the estimate of the flux according to equation 4.1 above or the appendix).

If, between two sampling points in time t1 and t2, a bolus containing the substance under consideration is added at time tB, the mean flux between t1 and tB and between tB and t2 is assumed to be the same. It may then easily be shown that equation (4.1) may also be applied in this case, with the amount of substance added via the bolus being included in the expression $m_{zu}$.

Thus, at the point in time of a current sampling from a training bioreactor, both the concentrations of extracellular metabolites in the previous sampling and the calculated extracellular fluxes calculated on the basis of the extracellular fluxes calculated since the last sampling are known and may be transferred together as reference value quantities to the MLP to be trained, which thereby learns, on the basis of the concentrations of extracellular metabolites measured in the last sampling, to predict the calculated extracellular ones in such a way that there is the smallest possible deviation from the calculated extracellular fluxes.

The trained MLP or the trained neural network may now be stored and used for one-step predictions of extracellular metabolite concentrations at any chosen future point in time $t^{(n+1)}$, for example the next day, based on the current concentrations $\bar{c}_{m,j}^{(n)}$ at that point in time $t^{(n)}$.

In summary, the idea of training the neuronal network is based on the fact that the concentrations of extracellular metabolites are easily measurable and from these, at least in retrospect, extracellular fluxes can be determined empirically. By using the concentrations of extracellular metabolites measured at a determined point in time as input parameter values and the extracellular fluxes, as they can be calculated over the time interval between this current point in time and a future point in time based on the concentration difference of an extracellular metabolite, as output parameter values, a neural network or in other machine learning algorithms may be trained to predict at least the extracellular fluxes for the one future point in time. The determination of the cell density allows an allocation of the total concentration difference in the medium to the individual cells of the cell culture contained in the medium.

The uptake/discharge rate of extracellular metabolite (reaction term) is calculated according to preferred embodiments from the difference of the total change of concentration of the substance in the bioreactor minus the substance added to/removed from the bioreactor (convection term). It was found that the reaction term for extracellular metabolites is determined primarily from the uptake or release into or through cells, so that the measured concentration changes of the extracellular metabolites may be essentially equated with the uptake or release rates of these extracellular metabolites into or from the cells. However, in some embodiments which provide for a significant supply or removal of certain extracellular metabolites during operation of the bioreactor, a corrective calculation may be made by subtracting from the measured concentration changes those parts of the concentration changes which are due to the external supply or removal of the extracellular metabolites to or from the culture medium when calculating the uptake or removal rates of these extracellular metabolites. However, this correction does not necessarily have to be made even in the Fed-Batch method. Also in the Fed-Batch method the incoming and outgoing flows are continuous. In the case of bolus feeding or sampling during fermentation, one obtains curves which are continuous over long distances and thus differentiable. This justifies the assumption of a differentiable course of the changes in concentration also for fed-batch reactors.

However, it is preferable to correct the measured cell density during training and/or in the predictions of the extracellular fluxes using the trained MLP. With the exception of batch fermentation, there seems to be a similar, approximately linear relationship between LDH concentration and cell density difference in fermentation approaches.

According to the design of the invention, a measured total cell density is continuously recorded in a fermenter and presented in a plot. In parallel, the cell density is calculated. The predictions may be calculated, for example, by a trained MLP trained according to embodiments of the invention, using the measured cell concentration as a further output parameter value. This "predicted" cell density is also plotted in the plot. Thus, according to embodiments of the invention, a first temporal profile of the measured cell density of a cell culture of a certain cell type is empirically determined and also a second temporal profile of a predicted cell density based on the metabolic model and the extracellular metabolite concentrations. Thus, a plot is obtained which contains a temporal profile of the measured and predicted cell densities and their deviation from each other.

It has been shown that there is often a considerable deviation between measured cell density and the cell density predicted by MLP, especially towards the end of a cell culture. The discrepancy between measured and predicted cell density is referred to in the following as the "density discrepancy profile" and may optionally also be shown graphically in the plot. The density discrepancy profile represents the temporal profile of the occurrence of lysed cells, which are not measurable as cells but still have an influence on the concentrations of extracellular metabolites. An empirical function, e.g. with the help of inner linear compensation lines over the density discrepancy profile characterized by two parameters and, is then generated, which sets the density of lysed cells according to the density discrepancy profile in linear relation to the LDH concentration in the medium measured at a determined point in time. This function allows an approximate conversion from the LDH concentration to the density difference and thus to the lysed cells. The corrected cell density is therefore the sum of the measured cell density and the number of lysed cells calculated by the linear function based on the measured LDH concentration. In other words, the measured cell densities $\bar{c}_{m,11}^{(n)}$ are supplemented by the density difference using this $$\bar{c}_{lys,11}^{(n)} := \bar{c}_{m,11}^{(n)} + a_1 \bar{c}_{LDH}^{(n)} + a'_0,$$

where $\bar{c}_{LDH}^{(n)}$ the LDH concentration at the n-th point in time is designated and $a'_0$ chosen so that $\bar{c}_{lys,11}^{(n_0)} = \bar{c}_{m,11}^{(n_0)}$ is applied if $n_0$ is a point in time when a fermentation was started.

These corrected cell density values are used to calculate the corrected biomass fluxes $\bar{v}_{lys,11}^{(n)}$ according to preferred execution forms. This has the advantage that the proportion of inconsistent flux distributions as a result of MFA is significantly reduced.

FIG. 2 shows an example of the process of information acquisition in several stages using different devices and data sources.

Cells whose metabolic state is to be predicted at a future point in time are kept in a bioreactor 208, for example in a fed-batch fermenter. The fermenter may contain some sensors or be operationally coupled to them, for example sensors for determining cell density. Instead of or in addition to these sensors, samples may be taken regularly from the cell culture and transferred to one or more analytical instruments. There the concentration of extracellular metabolites is measured. The measured cell density, the measured extracellular metabolite concentrations and, where appropriate, the point in time and amount of external supply of metabolites (e.g. glucose boli) are transferred to a data processing system 252. This system 252 comprises a metabolic model of the cell and an MLP trained to make predictions of the extracellular fluxes based on currently measured extracellular metabolite concentrations for the currently used cell type. The measured values received and measured at a determined point in time are transmitted as input to the trained MLP, which then predicts extracellular fluxes at a future point in time. In the course of a subsequent MFA, the extracellular fluxes and the stoichiometric equations of the model are also used to predict the intracellular fluxes for the future point in time. The complete model including the predicted extracellular and intracellular fluxes may be displayed and/or stored as a "snapshot" image 254 of the metabolic state of a cell via a graphical user interface.

If the bioreactor 208 contains a training cell culture, i.e. a cell culture from which data are regularly collected over a longer period of time in order to generate a training data set, the data processing system 252 is additionally adapted to calculate an extracellular flux for the future time interval (i.e. the time interval from the current point in time to the next point in time for which a prediction of the metabolic state is to be made) on the basis of a plot of the measured concentrations of extracellular metabolites and to transfer this to the MLP as an output parameter value during training.

Figure 3B:
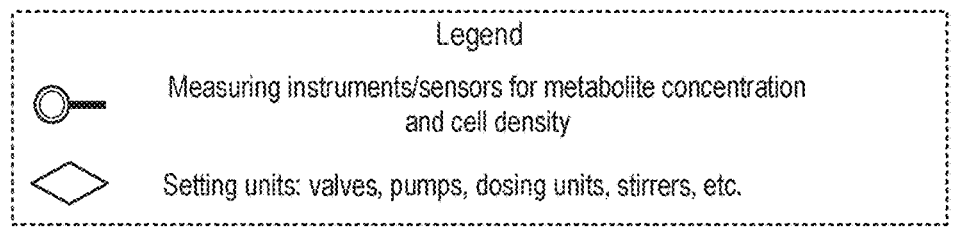

FIG. 3 shows a block diagram of a system for predicting the metabolic state of a cell, which may be used to monitor and/or control one or more bioreactors.

The System 200 may be a data processing system of various types. For example, it may be a desktop computer, a server computer, a notebook or a user's portable mobile device. The System 200 may be a control module that is part of or connected to a bioreactor or bioreactor plant with multiple bioreactors. In the embodiment shown here, the system is coupled to three bioreactors 204, 206, 208 and is configured to monitor the metabolic state of the cells in the respective cell culture in real time and to predict for a future point in time, for example a point 12 hours or 24 hours in the future. Each of the bioreactors may have one or more measuring devices or sensors for determining cell density and/or metabolite concentration or a mechanism that allows for sample naming so that the metabolite concentration can be determined by other devices by analysing the sample. Preferably, the 204-208 bioreactors have various control units such as valves, pumps, dosing units for boluses, stirrers, etc. which are coupled to the system and may receive and execute control commands from the system if necessary.

The System 200 includes one or more processors 202 as well as a first interface 210 for receiving measurement data from the one or more bioreactors. The interface 210 may be adapted as a direct interface to the bioreactors or as an interface to analyzing devices in which samples from the bioreactors are analyzed, or to a graphical user interface that allows a user to enter the obtained measurement data manually or by other means.

In addition, the system comprises or is coupled to 201 volatile or non-volatile storage medium 212. The storage medium may be, for example, main memory, hard disk, or memory of a cloud service, or network storage, or combinations of the above types of storage. The storage medium contains a metabolic model 214 of the cells held and proliferated in the bioreactors, for example a model as shown in FIG. 4.

The storage medium comprises a trained MLP 218, for example a trained neural network, adapted to predict one or more extracellular fluxes at a future point in time from the measured concentrations of several extracellular metabolites received at a future point in time.

In addition, the storage medium comprises a program logic 220, which is adapted to transfer the received measured values to the MLP 218 in order to perform a prediction of extracellular fluxes. Furthermore, the program logic is adapted to perform a real-time metabolic flux analysis (MFA) based on the metabolic model 214 and the predicted extracellular fluxes in order to predict intracellular fluxes for the future point in time. The program logic 220 may be implemented in any programming language, e.g. C++, Java, Matlab, or in the form of several program modules in different or the same programming language that are interoperable with each other.

Optionally, the storage medium may contain several reference values and reference value ranges. These reference values or reference value ranges indicate acceptable or desirable intracellular fluxes of different intracellular metabolites. By real-time comparison of the predicted intracellular fluxes with the reference values 216, program logic 220 may detect whether the cells in one or more of the bioreactors are heading towards an undesirable metabolic state and, if necessary, take countermeasures by issuing appropriate control commands to the respective reactor via a second interface 222 to counteract the predicted trend. Alternatively or in addition, in this case a warning may be given to a user via a user interface 224, for example a display device, for example an LCD display. The display device may inform the user of the predicted extracellular and intracellular fluxes and also of any predicted deviations of these fluxes from desirable reference ranges.

FIG. 5 shows the calculation of intracellular fluxes at several successive points in time during the operation of a bioreactor. The upper plot 502 shows a profile of the concentration of an extracellular metabolite determined at six measurement points (one measurement per day). The middle plot 504 shows that a trained MLP uses these measurements to predict one or more extracellular fluxes for a future point in time. A comparison of the positions of the points in the upper and middle plot shows that the points in time at which the measurement data were collected and the points in time at which the extracellular fluxes were predicted are about half a day apart.

This means that if, for example, the concentrations of extracellular metabolites are measured daily at 12:00 noon, these data are used to predict the extracellular fluxes at midnight. The lower plot 506 shows that by performing an MFA at each of these future points in time the predicted extracellular fluxes were supplemented by predicted intracellular fluxes.

FIG. 6 shows different fluxes that are represented in the metabolic model shown in FIG. 4. The fluxes were calculated on the basis of the measured change in metabolite concentrations over a time interval and the measured cell density and show that the fluxes for different metabolites have a very different and partly characteristic course.

FIG. 7 illustrates the successful use of the method for generating biological knowledge. The plot of the glucose flux on the upper left shows that in the profile of the glucose flux at about point in time 0.65 the glucose flow comes to a virtual standstill. Effects of this glucose deficiency can be observed for alanine, series and glycine: Alanine is absorbed at higher rates in the case of the limitations, which probably serves to provide more pyruvate. In addition, a stronger conversion from serine to glycine takes place, which is associated with increased ammonium formation.

A comparison of the glucose and product flow curves reveals certain similarities: both curves show a temporary decrease of the fluxes at an early point of fermentation as well as a later collapse when glucose was temporarily absent from the medium. This dip is missing in the product flows of the fermenters without glucose limitation. Similarly, the effect of the glucose boli, which shows the sensitivity of the glucose flux to the glucose concentration in the medium, can also be seen in the product formation. Obviously there is a very close connection between these fluxes. At the end of the fermentation process, the amount of substance in the product was highest in those bioreactors without glucose limitation. Therefore, the availability of glucose seems to be essential for effective product formation, and a shortage should be strictly avoided.

FIG. 8 illustrates another successful use of the method for generating biological knowledge.

The so-called lactate shift refers to the effect frequently observed in cell culture cultivation that the lactate flow changes the sign from positive to negative. There are numerous attempts in the literature to explain the lactate shift. Mulukutla et al. postulate, for example, that the lactate shift is the result of regulatory mechanisms that are set in motion by increasing lactate inhibition. This biological hypothesis was tested by determining the lactate flux in several bioreactors over several measurements using the method according to the invention and by measuring the extracellular lactate concentrations. The corresponding results are shown in FIG. 9 for four bioreactors. It was shown that at the point in time when a reversal of the net flow direction of the lactate was observed, the lactate concentration in the different bioreactors was different. Thus, the mechanism postulated in the literature up to that point does not seem to be responsible for the lactate shift. Rather, it seems as if the shift depends on the glutamine metabolism, as shown in Figure 6.2 of the appendix. A comparison of the courses of glutamine concentrations and lactate flows in several different fermenter types shows that the lactate shift is always accompanied by a complete consumption of glutamine.

This observation has also been reported in the literature, where a determined CHO clone was described in which the shift occurred only after glucose was consumed (Zagari F, Jordan M, Stettler M, Broly H, Wurm F M (2013): "Lactate metabolism shift in CHO cell culture: the role of mitochondrial oxidative activity", New Biotechnology, Vol. 30, No. 2). According to the invention, it is thus possible, by repeatedly predicting intracellular fluxes and by comparing these fluxes with other intracellular fluxes and/or concentrations of extracellular metabolites, to successfully test and, if necessary, reject hypotheses regarding cell metabolism and to identify metabolic peculiarities of individual cell clones. Based on the results of the analysis, it is obvious that the majority of the lactate formed in the common CHO clones originates from glutaminolysis. Interestingly, after the lactate shift, glutaminolysis initially comes to a standstill: no more glutamine uptake takes place, rather it is formed in small quantities, which increases its concentration in the bioreactor. The cells now seem to have adjusted their metabolism exclusively to the substrate glucose. It is noticeable that a second phase of glutamine uptake may be observed as soon as glucose reaches very low concentrations. At the same time, a short phase of renewed lactate production can also be observed.

FIG. 9 shows plots with lactate fluxes and glutamine concentrations of four bioreactors of different types, which allows a comparison of the courses of glutamine concentration and lactate flow in a determined cell culture. The glutamine concentrations are indicated by solid lines and the lactate fluxes by dotted lines. The lactate fluxes and concentrations of the individual fluxes and metabolites were previously normalized to increase comparability. The arrows indicate a reversal of the sign of the lactate flux.

FIG. 10 shows the time courses of intracellular fluxes as calculated by descriptive modelling using MFA based on the metabolic model for the current point in time (i.e. descriptive, not predictive).

In section 2.2.2 of the appendix different methods are presented to treat redundant metabolic models. For the calculation of the fluxes, the optimization problem (equation 2.9 in the appendix) was solved and thus a weighted least squares solution was obtained. This allowed the extracellular fluxes obtained by solving the optimization problem to differ from the fluxes calculated directly from the experimental data.

Equation (2.10) of the appendix was used to calculate the extracellular, balanced fluxes, the intracellular ones were determined by equation (2.5) of the appendix, also $$\hat{v}_m = (I - C_{\tilde{v}_m} R' C_{\tilde{v}_m} R'^T)^{-1} R') \bar{v}_m$$

and $$\hat{v}_u = -A_u^{\#} A_m \hat{v}_m.$$

For the formulation of the covariance matrix $C_{\tilde{v}_m}$, the results of the model validation are preferably included, which showed which standard deviations led to a largely consistent model and which measured values should possibly be classified as unreliable.

Afterwards the calculated fluxes were visualized: On the one hand, their time courses were plotted separately according to metabolites, on the other hand, the entire flux distribution at selected points in time was visualized.

FIG. 11 shows snapshots of intracellular and extracellular fluxes at different points in time during the cultivation of a cell culture of CHO cells.

In addition to the course of individual material fluxes over time, snapshots of the entire intra- and extracellular flux distribution in the individual time intervals may be considered. FIG. 11 shows an example of four metabolic states of cells from the fourth fed-batch fermentation. They originate from the second, eleventh, 14th and 21st time intervals. The four pictures show flux distributions during a fed-batch fermentation. The gluc39ose flow in the second time interval serves as a reference. The product flow was multiplied by 10,000.

Figure 11A:
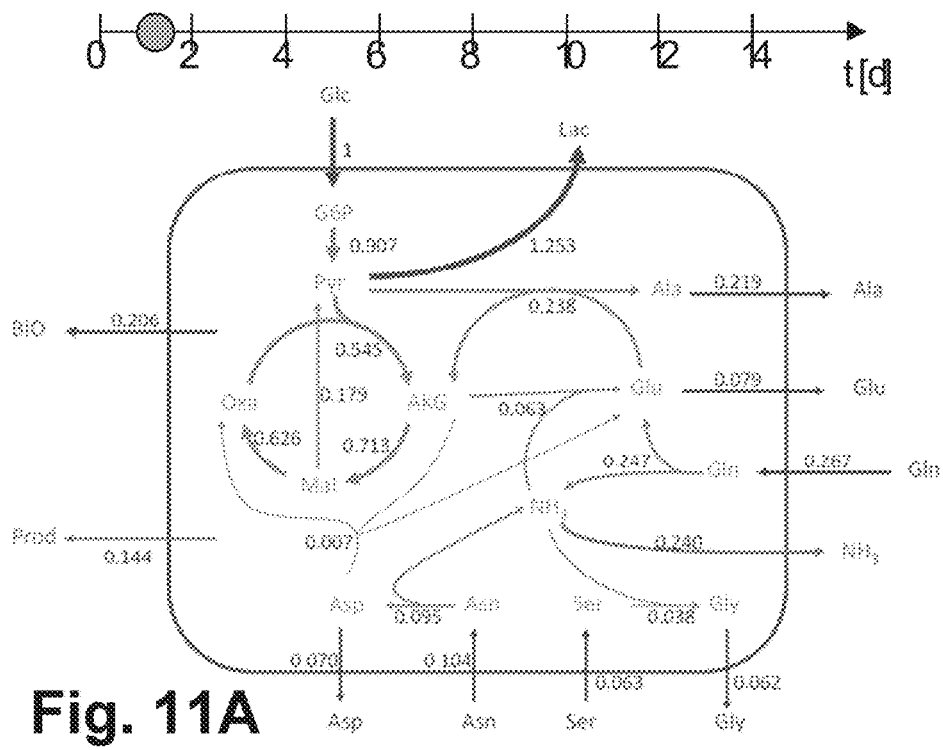

In the second time interval, i.e. in an early fermentation phase (phase I in the classification, shown in FIG. 11A, glucose is still in excess, is rapidly transported into the cells and enters the citrate cycle. Glutamine is also taken up, conversion to glutamate takes place and further together with pyruvate via flux v_8 into metabolites of the citrate cycle and into alanine. Lactate and ammonia are released into the medium in larger quantities.

Figure 11B:
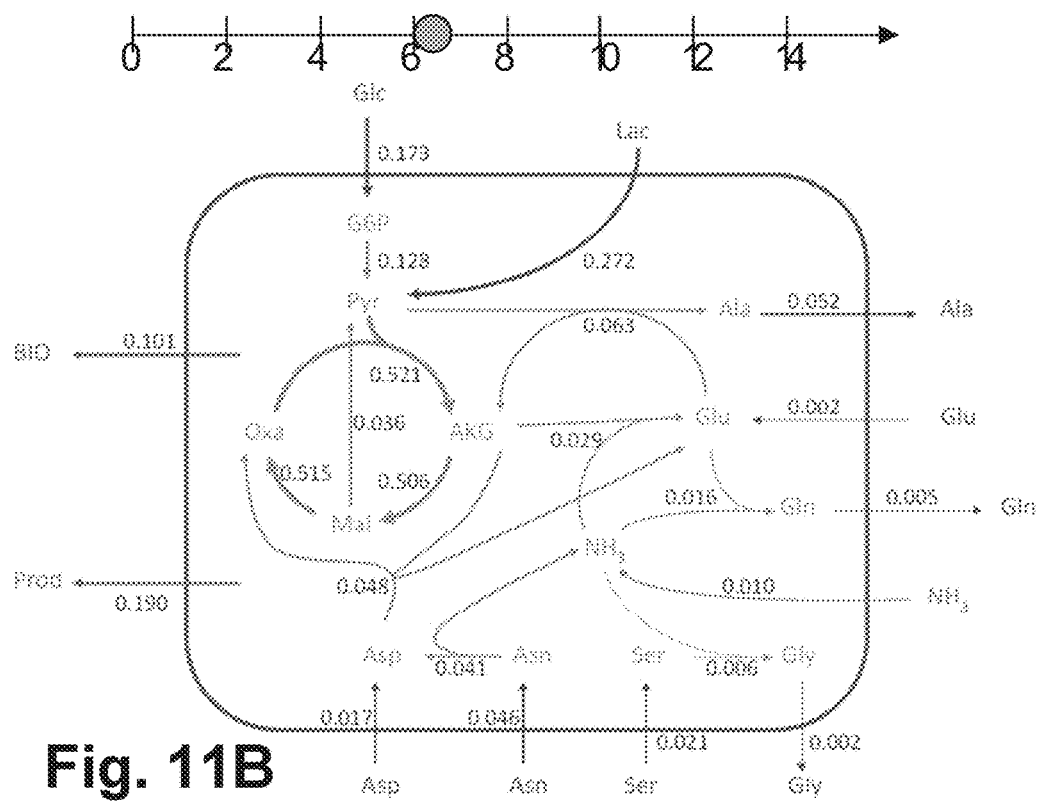

In the eleventh time interval (phase III), shown in FIG. 11B, the lactate shift has already taken place, i.e. lactate is absorbed from the medium, metabolized to pyruvate and then enters the citrate cycle. Glucose consumption is reduced, glutamine is no longer absorbed. Ammonium is no longer released. Biomass production has decreased, but product formation has increased.

Compared to the start of fermentation, the citrate cycle runs with almost unchanged intensity, but the anaplerotic reaction of malate to pyruvate is reduced.

Figure 11C:
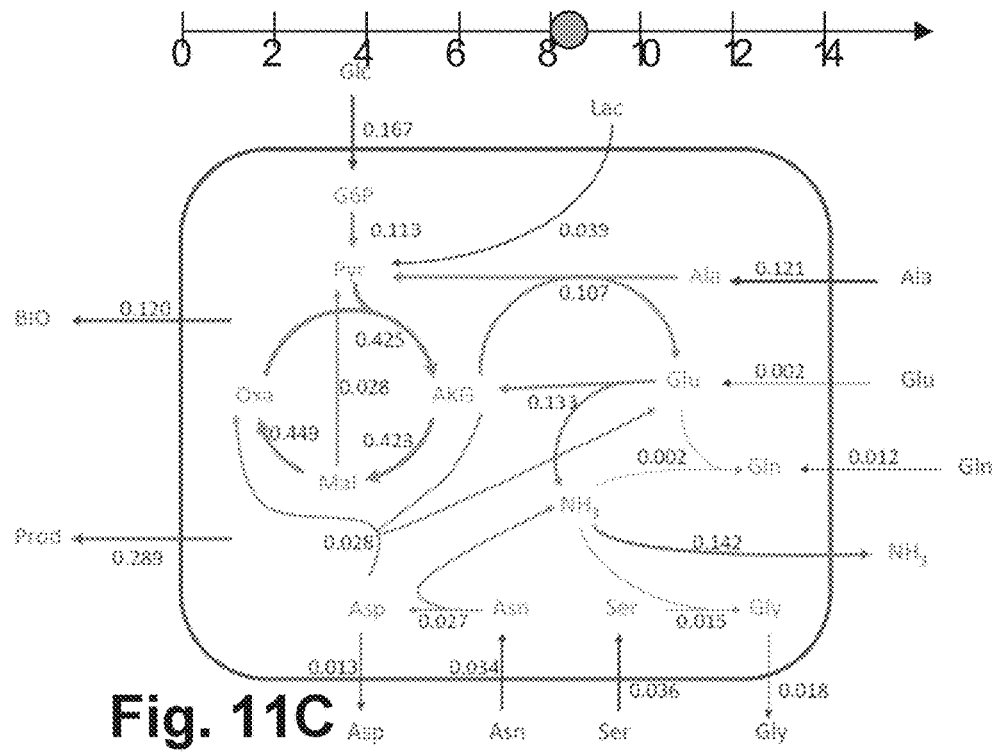

In the 14th time interval (also phase III), shown in FIG. 11C, the lactate concentration in the medium is very low, so that intake is also restricted. Therefore alanine is absorbed and converted into pyruvate. Ammonium is again increasingly released into the medium. The product formation has increased even further.

Figure 11D:
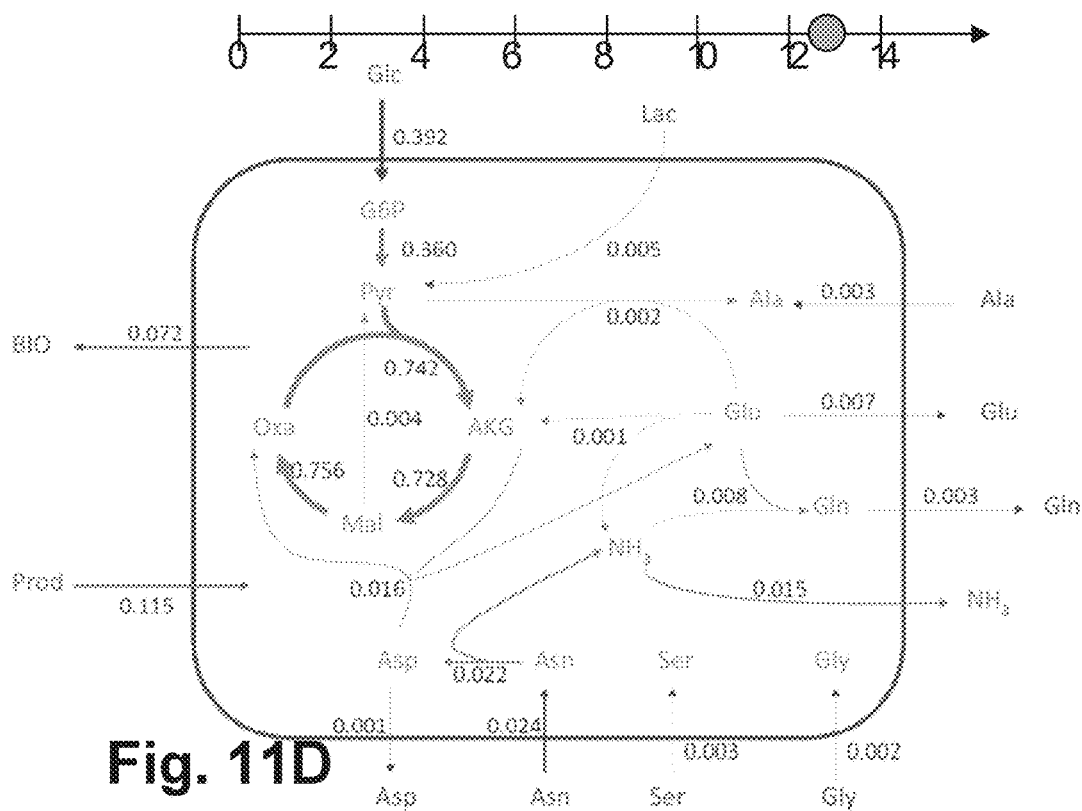

Towards the end of the fermentation (phase IV), shown in FIG. 11D, glucose is added in a bolus-like manner. Therefore, the uptake is increased again and the flux through the citrate cycle is particularly strong. However, all other reactions are extremely reduced.

FIG. 12 shows the strongly correlating course of intracellular fluxes, which were calculated for the current point in time using descriptive MFA and predicted for a point in time in the future using a combination of the MLP and MFA. A "descriptive MFA for the current point in time" calculates the extracellular fluxes of the metabolic model from the measured fluxes of the extracellular metabolites over the just elapsed time interval and uses these extracellular fluxes as input for the MFA to calculate the intracellular fluxes for the current point in time. In contrast, the "predictive" determination of the intracellular fluxes is based on predicting extracellular fluxes for the future point in time using the trained predictions of the MLP and using the extracellular fluxes thus predicted as input for the NSA to predict the intracellular fluxes at the future point in time.

FIG. 13 shows some of the extracellular metabolites whose concentrations are used as input values to predict extracellular fluxes.

For each extracellular metabolite flux (given in the top row of the table) that is to be predicted once by the trained MLP and that is passed as output parameter values during training, the column below lists the input metabolites in descending relevance for estimating the flux of the "output metabolites". Bio" here means the measured biomass, preferably specified in terms of cell density, and "TZD" means the value corrected for LDH concentration. The PMI calculation performed to determine this relevance is preferably based on the values from all training fermentations performed.

The table also contains the results of the cross-validation, where the number of input variables, the number of hidden variables H and the number of iterations were determined. The input metabolites 1504, whose concentrations enter the neural network as input parameter values, are highlighted in yellow.

The values from several (e.g. 3) fed-batch fermentations as well as those from one batch approach were used as training data set. Data from other fermenters with the same cell type formed the test data set. In addition, cross-validations with other training/test data set partitioning may be performed.

However, the listing shown in the table does not necessarily correspond to an order that is intuitive from a biological point of view: for example, glucose concentration plays a subordinate role here, although it would be obvious that the most important substrate of the CHO cells has a major influence on some substance conclusions. However, the PMI-based arrangement described below has only limited biological significance, which may be attributed to the following facts: the courses of metabolite concentrations are correlated to a certain extent via metabolism. Therefore, it is possible that after the selection of one metabolite, many others may lose relevance for the estimation, since much of the information contained in them is already described by the first metabolite. However, the selected metabolite may not be the one that, from a mechanistic point of view, actually has an influence on the substance flow, but is only strongly correlated with it. In fact, it may have been observed that a sample of white change in the data selection used to calculate the PMI values resulted in different arrangements in some cases. In some cases, for example, the position of glutamate and glutamine, which are closely linked via the metabolism, was reversed. However, a selection based on biological intuition, as it is done today in some publications, sometimes resulted in much worse predictions. This may be due to the fact that the biological relationships are often not always known and that redundant information is selected. In addition, the literature study to select suitable input parameter values based on presumed biological relevance takes a lot of time.

At first, for each metabolite flow the potential inputs were sorted according to their relevance using Partial Mutual Information (PMI), see equation 2.19 in the appendix. The PMI was calculated using the discretization according to Equation 2.22 in the Appendix). The core density estimator used is based on city block function, the Nadaraya-Watson estimator (see Equation 2.27 in the Appendix) was used to calculate the residuals. A training data set was used for this. As in the present case, this may comprise the measurement data of 8 cell culture projects in 8 different bioreactors.

The order of the inputs for estimating the j-th extracellular metabolite flux was performed according to the following algorithm:
1. summarize in the set X all potential input variables, here all current concentrations of extracellular metabolites. The set U contains all already selected input variables (it is empty at the beginning). Y is the output variable, i.e. the j-th extracellular metabolite flux between the current and the future sampling time.
2. calculate an approximation for the partial transinformation between each potential input variable in X and Y considering the elements in U based on the given, standardized data set. For example, through standardization, all input variables and the output variable had a mean value of 0 and a standard deviation of 0.5, thus eliminating distorting effects on the relevance of the variables due to different orders of magnitude. Preferably, this standardization is performed before training the neural network with respect to the measured values of the training data set as well as when entering current measured values in the test procedure using a trained MLP with respect to the currently obtained measured values.
3. note the variable in X, which has the highest PMI value. Add it to U and remove it from X.
4. Repeat steps 2 and 3 until X is empty.

According to embodiments of the invention, the PMI for the parameter X, e.g. a determined extracellular metabolite, is calculated with respect to the parameter Y, e.g. another extracellular metabolite, as follows $$I'(X, Y) := \int\int g_{x',y'}(x', y') \ln\left(\frac{g_{x',y'}(x', y')}{g_{x'}(x')g_{y'}(y')}\right) dx' dy' \quad (2.19)$$

given with the residues $$x':=x- \mathbb{E}[x|U] \quad (2.20)$$

and $$y':=y- \mathbb{E}[y|U]. \quad (2.21)$$

Where g is the density function of the marginal or common distributions. The residuals contain only the information of X and Y, which are not yet contained in U. The larger the value for I', the stronger the dependence.

An approximate, discrete version of expression 2.19) is as follows:

$$I'(X, Y) = \frac{1}{N}\sum_{n=1}^{N} \ln\left(\frac{g_{x',y'}(x^{(n)'}, y^{(n)'})}{g_{x'}(x^{(n)'})g_{y'}(y^{(n)'})}\right), \quad (2.22)$$

$(x^{(n)}, y^{(n)}, n=1, \ldots, N$, pairs of samples of X and Y and $(x^{(n)'}, y^{(n)'})$ are the associated, $g_{x',y'}$-distributed pairs of residuals. The usually unknown density functions may in turn be approximated by core density estimators, which also use information from the N samples. These estimators provide—in simple terms—a continuous density function which is similar to the histogram of the samples. It results from a weighted superposition of N core functions. These in turn are density functions that are bell-shaped and symmetrical about one of the sample values each.

Among other things, the Gauss core and the city block function have been used in publications to date to calculate the PMI.

In general terms, the estimation of the density of a q-dimensional random vector X with the samples $x^{(1)}, \ldots, x^{(N)}$ using the core function K with bandwidth $\mu$ is $$\hat{g}_x(x) = \frac{1}{N}\sum_{n=1}^{N} \mathcal{K}_\mu(x-x^{(n)}) = \frac{1}{N}\sum_{n=1}^{N} \frac{1}{\mu^q}\mathcal{K}\left(\frac{x-x^{(n)}}{\mu}\right).$$

With the city block function as the core function, this results in:

$$\hat{g}_x(x) = \quad (2.23)$$

$$\frac{1}{N}\sum_{n=1}^{N} \frac{1}{\mu^q}\prod_{j=1}^{q}\left(\frac{1}{2}e^{-\frac{|x_j-x_j^{(n)}|}{\mu}}\right) = \frac{1}{N(2\mu)^q}\sum_{n=1}^{N} e^{-\frac{1}{\mu}\sum_{j=1}^{q}|x_j-x_j^{(n)}|}.$$

The common density distribution of two random vectors X and Y can be formulated using an estimator with product core $K_{\mu_x,\mu_y}(x,y)=K_{\mu_x}(x)\cdot K_{\mu_y}(y)$:

$$\hat{g}_{x,y}(x,y) = \frac{1}{N}\sum_{n=1}^{N} \mathcal{K}_{\mu_x}(x-x^{(n)})\cdot \mathcal{K}_{\mu_y}(y-y^{(n)}).$$

The choice of the range has a significant impact on the quality of the estimate. The larger the bandwidth, the smoother, but also less detailed the density approximation. In several studies and in the present case the choice $$\mu = \left(\frac{4}{N(q+2)}\right)^{\frac{1}{q+4}}$$

proven a success.

For the calculation of redundancies according to equations 2.20 and 2.21, the conditional expectation value $\mathbb{E}[X|U=u]$ for two random vectors X and U must generally be estimated. The Nadaraya-Watson estimator may be used for this purpose. This is based on the previously applied principles and can be derived as follows:

$$\mathbb{E}[X \mid U = u] = \int \frac{x\cdot g_{x,u}(x,u)}{g_u(u)}dx$$

$$\approx \frac{\int x \sum_{n=1}^{N}(\mathcal{K}_{\mu_x}(x-x^{(n)})\mathcal{K}_{\mu_u}(u-u^{(n)}))dx}{\sum_{n=1}^{N}\mathcal{K}_{\mu_u}(u-u^{(n)})}$$

$$= \frac{\sum_{n=1}^{N}\mathcal{K}_{\mu_u}(u-u^{(n)})\int x\mathcal{K}_{\mu_x}(x-x^{(n)})dx}{\sum_{n=1}^{N}\mathcal{K}_{\mu_u}(u-u^{(n)})}$$

$$= \frac{\sum_{n=1}^{N}x^{(n)}\mathcal{K}_{\mu_u}(u-u^{(n)})}{\sum_{n=1}^{N}\mathcal{K}_{\mu_u}(u-u^{(n)})}.$$

In the approximate step the densities were approximated by means of core density estimators. The last equal sign results from the fact that $K_{\mu_x}(.-x^{(n)})$ is.

According to embodiments of the invention, the selection is carried out according to the principle of a wrapper: For each output variable 70 nets with the 1 to 7 (according to PMI) most relevant inputs and with 1 to 10 hidden neurons were trained in initially 1000 iterations. For this purpose, a training data set was created from a part of the entire training data set, which was formed from the 8 monitored training fermentations. The remaining data served as test data. For each training session, the value of the test error E was recorded over the number of iterations and its minimum value and the corresponding number of iterations were determined.

Subsequently, the 70 nets were compared using the total minimum test error. This resulted in the determination of the combination of input variables to estimate the respective metabolite flux, as well as the corresponding number of iterations and the number of hidden neurons.

The list of selected input parameter values, here also called "inputs" or 'input variables', for different output parameter values ('outputs', 'output variables') is indicated accordingly in FIG. 13.

According to preferred embodiments, the selection of those extracellular metabolites whose concentration is to be used as input parameter values for training or feeding the trained MLP ('input metabolites') is made according to purely statistical criteria, individually for each output metabolite, i.e. individually for each extracellular flux to be predicted.

1. Ranking the Input Metabolites According to their "Relevance":

First, all measurable available input metabolites or at least all metabolites that occur in the metabolic model as extracellular metabolites are transferred into a "first set" and sorted according to their relevance: By using the PMI criterion, it is determined which metabolite has the greatest significance/predictive power for the output (rate of the extracellular metabolite whose extracellular flux is to be predicted—"output metabolite"). This metabolite is transferred to a "second set", which then provides the actual input parameter values. The "relevance" or predictive power determined in this first sorting step does not yet depend on the metabolites in the second set.

2. Determination of the True Input Metabolites:

Preferably, not all input metabolites are used as input for MLP training or MLP application (this leads to very poor predictive power due to overfitting). It is therefore determined how many of the most relevant input metabolites should be used. This is done by determining the predictive power of the 'x' most relevant input metabolites from a test data set, varying x, and then selecting the number x with the best predictive power.

After the first sorting step and the transfer of the most relevant metabolite from the first to the "second set" of actual input metabolites (whose concentration is provided by the input parameters of the MLP), the input metabolite within the remaining metabolites in the first set is repeatedly identified that has the greatest predictive power with respect to the flux of a determined output metabolite, taking into account the content of the second set. If the concentration profile of the metabolite with the highest predictive relevance within the remaining members of the first set correlates strongly with a metabolite already contained in the second set, this metabolite is usually not transferred to the second set, since although its predictive power may be high, its concentration profile does not make a significant contribution over that of a metabolite already contained in the second set. Rather, its uptake would only increase the amount of redundant information in the second set. Therefore, if the metabolite in the first set may not be included in the second set for these reasons, the metabolite with the next highest relevance score of the first set, which does not lead to an excessive increase in the redundancy of the information content of the concentration profiles of the metabolites of the second set, is transferred from the first to the second set.

Thus, a metabolite may be very meaningful for the rate of output of a certain output metabolite without being transferred to the second set. A transfer may be omitted in particular if the concentration profile of this metabolite correlates very strongly with that of a metabolite that is already contained in the second set, so that it is sufficient to use only one of the two or its concentrations as an input parameter value when training the MLP and later also when using the trained MLP. This means that if one of the two is selected as "relevant", the other loses its significance. This is recognized by the PMI criterion). Continue in this way until all input metabolites that are relevant in terms of their predictive power and sufficiently independent of each other have been included in the second set.

For example, in the case of the Glu flux (4th column in the table shown in FIG. 13) it has been found that information about the current biomass and the current glycine concentration may provide better predictions than if only biomass is used as input (too little information), or if additional information about glutamine, aspartate etc. is fed into the neural network (too much information, overfitting).

FIG. 14 shows a histogram of the obtained "Root Mean Square Error" (RMSE) for intracellular fluxes obtained for several fed-batch fermentation runs: 12 fed-batch reactors were prepared, each containing one CHO cell clone different from the cell clones of the 11 other reactors. The 12 cell clones were genetically modified so that all 12 clones produced the same product, namely a bispecific antibody. Although the same DNA sequence was used during transfection to produce the clones, the clones exhibit metabolic differences due to different insertion loci and/or different copy numbers of the integrated DNA sequences. 10 fed-batches were used for training the MLP (here: a neural network model), two fed-batches for testing the model. These two fed-batches were used for the RMSE calculations.

The RMSE for the intracellular fluxes are calculated from a difference between the intracellular fluxes predicted by a combination of MLP and MFA and intracellular fluxes calculated from measured extracellular fluxes. RMSE is never negative, a value of 0 (almost never reached in practice) would indicate a perfect fit of predicted and measured data. In general, a lower RMSE is better than a higher one. RMSE is the square root of the average of the squared errors. The effect of each error on RMSE is proportional to the magnitude of the squared error, so larger errors have a disproportionate effect on RMSE.

The same type of medium and the same culture media were used for the 12 fed-batch reactors to produce the bispecific antibody. However, the medium and culture media differed from the medium and culture media used for the bioreactors or cell cultures, whose metabolic footprint is shown in Figure 5.9 of the Appendix.

The MLP, here a neural network (NN), was recalibrated to the new data set, i.e. the NN, which had already been trained once on data obtained from the bioreactors shown in Figure 5.9 of the Appendix, was "retrained" or newly trained on data from the 12 fed-batch reactors for—production of the bispecific antibody. The models were generated in Python using the machine library—Scikit learn. The hyperparameters of various NN models were optimized using a grid search function. Models and hyperparameters that best matched the data were stored and used in the form of a "re-trained" NN for future predictions of extracellular as well as intracellular fluxes of the cell cultures in the 12 bioreactors.

FIG. 15 shows a histogram of the obtained RMSE for extracellular fluxes obtained for the 12 fed-batch fermentation runs mentioned in FIG. 14. All RMSE values are normalized to the error obtained for the metabolite glucose. The RMSE values for extracellular fluxes are calculated from the difference between measured external fluxes and extracellular fluxes predicted by a combination of the MLP, in particular a neural network, and MFA.

It may be observed that the RMSEs of both intracellular and extracellular fluxes obtained for the 12 fed-batch reactors for the production of the bispecific antibody were in the same range as RMSEs obtained for other cell cultures or other cell clones (see Master Thesis—"Appendix"—page 67, Figure 5.9, the protein product of this cell culture is an antibody fusion protein. The 12 cell cultures are CHO cell cultures. The RMSE of the external and internal fluxes (measured against the predicted ones) were between 10-35%.

FIG. 16 shows a comparison of the predicted extracellular metabolite fluxes (black line) with two extracellular metabolite fluxes (two grey lines) measured for two identical cell clones in different bioreactors (fed-batch and split batch bioreactor) for different metabolites (amino acids). The cell clones in both bioreactors are recombinant CHO cells (monoclonal), which synthesize a specific antibody fusion protein. The curves show that the method according to embodiments of the invention is capable of very accurately predicting the fluxes of extracellular metabolites for both fed batch (fb) and split batch (b). In detail, FIG. 16 shows a comparison of the extracellular measured fluxes with the predicted extracellular fluxes in different combinations of training data/test data set. The expression "fb/fb+b" means fed-batch data set as training data and fed-batch+batch as test data set. One run from the test data set is then shown in each case.

FIG. 17 shows several plots with two curves each, all obtained for a fed batch bioreactor with a cell clone for the production of the antibody fusion protein. The curves consisting of dotted lines ("descriptive MFA") were obtained by using measured concentrations of extracellular metabolites as input of a metabolic flux analysis (MFA) to calculate different extracellular fluxes, each corresponding to one of the 11 plots. The solid line curves ("NN-MFA") were obtained by using measured concentrations of extracellular metabolites at a determined point in time t0 as input of an MLP (e.g. NN) to predict extracellular fluxes at a future point in time t1, and using these future predicted extracellular fluxes as input for the metabolic flux analysis (MFA). Thus, a comparison of the two curves of each of the 11 plots shows that the values predicted by MLP+MFA for a future point in time have a very high agreement with values obtained with a static MFA model using measured now-time concentrations of extracellular metabolites.

FIG. 18 shows several plots with two curves each, all obtained for a fed batch bioreactor with a first cell clone ZK1 for the production of a bispecific antibody. The curves consisting of dotted lines ("NN+Descriptive MFA extracellular") were obtained by using measured fluxes of extracellular metabolites at a particular point in time t0 as input of an MLP (e.g. NN) to predict extracellular fluxes at a future point in time t1 and using these future predicted extracellular fluxes as input for the metabolic flux analysis (MFA). The crossed line curves ("Descriptive extracellular MFA") were obtained by using currently measured extracellular fluxes of extracellular metabolites as input for metabolic flux analysis (MFA) to calculate different extracellular fluxes, each corresponding to one of the plots shown in FIG. 18. The extracellular fluxes were normalized for each plot and for each day in terms of glucose concentration. Thus, instead of measured extracellular metabolite concentrations, current extracellular fluxes calculated based on current and past metabolite concentrations at a point in time in the past were used as MLP input. Thus, a metabolite concentration in a broader sense was used as input. It was observed that if alternatively the measured metabolite concentrations were used as input, the prediction results of the MLP were ultimately essentially identical. Thus, measured concentrations in the narrower sense as well as metabolite concentrations in the broader sense may equally serve as input for the MLP.

Thus, a comparison of the two curves of each of the plots in FIG. 18 shows that the values predicted by MLP+MFA for a future point in time are in good agreement with values obtained with a static MFA model using measured now-time concentrations of extracellular metabolites. However, deviations in detail are possible.

The plots in FIG. 18 compare a) the progress of the measured (extracellular) fluxes with their MLP predicted counterparts. All fluxes are expressed as normalized values—normalized to the measured flux. Therefore the glucose flux is always at 1 (not shown as a plot); and b) the progress of the internal fluxes from measured external fluxes calculated by MFA with the internal fluxes from external fluxes calculated by MFA from external fluxes calculated by NN. Again, all fluxes are normalized against the glucose flux.

For individual metabolites, the measured fluxes occasionally deviated from the predicted ones. On the one hand, however, it should be noted here that the scaling corresponds to a very high "resolution" due to the glucose normalization and the deviations were rather small when considering the total amount of metabolite. Furthermore, a certain tendency of the data to overfitting was observed, which can usually be corrected by increasing the size of the data set.

The plots of FIG. 18 generated for 11 different extracellular fluxes represent a "metabolic fingerprint" of the cell clone ZK1. In the following, it will be shown that this fingerprint may differ significantly from that of other cell clones that produce the same product (bispecific antibodies, but which contain the sequence coding for the protein in a different number of copies or at a different location in the genome.

FIG. 19 shows several plots with two curves each, all obtained for another fed batch bioreactor BR2 with a second cell clone ZK2 for the production of the bispecific antibody. The curves were determined as described for FIG. 18, but based on data from the second cell clone ZK2. The plots shown in FIGS. 18 and 19 are based on data from two bioreactors BR1, BR2, operated with the same type of medium and culture medium and which differ essentially only in that the two bioreactors hold different cell clones ZK1 and ZK2, which both synthesise the same product (bispecific antibody) but have genetic differences which may also affect the metabolism of the clones: For example, the clones may have been produced by a method which does not provide complete control over the position of integration of a new DNA sequence segment into the genome of the cells and/or the number of integrated sequence segments. Thus, although the starting cells used are genetically identical, in the course of the integration of new genes or DNA sequences (e.g. in the case of random integration in the course of a transfection), the gene sequences for the light chain (LC) and the heavy chain (HC) of the bispecific antibody may be inserted in different numbers of copies and different genome loci. This in turn may cause metabolic differences and also differences in the productivity and vitality of a specific cell clone, which according to the embodiments of the invention are readily discernible and differentiable by metabolic predictions of the MLP and MFA combination. The second bioreactor BR2 was identical in construction to bioreactor BR1, which was used for the cell culture of clone ZK1.

FIGS. 18 and 19 each show for a specific cell clone ZK1, ZK2 that the combination of a neural network NN and a metabolic flux analysis MFA leads to different and ultimately more accurate predictions than a prediction of extracellular fluxes based purely on MFA and actual time. In addition, this combination has the advantage that the quality of the prediction can be repeatedly verified by the measured fluxes. A direct prediction of the intracellular fluxes would only allow a verification with 13C-labelled metabolites, which is neither practicable nor economical, especially for high throughput or even production fermentations. Furthermore, a calculated amount of predicted extracellular fluxes for a specific cell clone ZK1, ZK2, as e.g. shown in FIG. 18 for ZK1 and in FIG. 19 for ZK2, represents a "metabolic fingerprint" of a specific cell clone. This may be analysed to identify specific cell clones which appear to be particularly beneficial with respect to a determined parameter such as growth rate, rate of ammonia degradation, rate of serine production, etc. Metabolic "fingerprints" may also be used to select or characterise two or more different cell clones with regard to their metabolic similarity.

FIG. 20 shows several plots with two curves each, which were all obtained for the BR1 bioreactor with the cell clone ZK1 and which each represent calculated intracellular fluxes. FIG. 20 corresponds to FIG. 18 with the difference that the calculated intracellular instead of extracellular fluxes are shown.

FIG. 21 shows several plots with two curves each, which were all obtained for the BR2 bioreactor with the cell clone ZK2 and which each represent calculated intracellular fluxes. FIG. 21 thus corresponds to FIG. 19 with the difference that the calculated intracellular instead of the calculated extracellular fluxes are shown. The entirety of the plots in FIGS. 19 and 21 thus represents a metabolic fingerprint which may be used for the metabolic characterization of a cell clone. By collecting data from a large number of these "fingerprints" for a large number of different clones and fermentation conditions and by recording the vitality and/or productivity of the individual clones, it is possible, e.g. by means of correlation analyses, to identify advantageous metabolic fingerprints and to use these metabolic fingerprints identified as advantageous as a reference value in order to identify advantageous clones for future cloning and to select them for a fermentation project.

LIST OF REFERENCE NUMERALS

102-112 Steps
200 System
202 Processor
204 Bioreactor
206 Bioreactor
208 Bioreactor
210 Measured value interface
212 Storage medium
214 Metabolic model
216 Reference values
218 Machine learning logic
220 Program logic
222 Control interface
224 User interface
250 Device for determining the concentration of metabolites
252 Computer system for calculation and prediction
254 Metabolic model with fluxes
256 Measured extracellular metabolite concentrations
402 Metabolic model
404 Extracellular metabolites
406 Intracellular metabolites
408 Extracellular fluxes
410 Intracellular fluxes
502 Course of measured concentrations extracellular metabolite
504 Course of predicted extracellular flux
506 Course of intracellular fluxes calculated by MFA
802 Plot for Fed-Batch Bioreactor 1
804 Plot for Fed-Batch Bioreactor 5
806 Plot for Batch Bioreactor
808 Plot for Split-Batch Bioreactor
1502 Output parameter values
1504 Input parameter values

The invention claimed is:

1. A method for controlling a bioreactor which includes cell culture of cells of a specific cell type based upon predicting a metabolic state of the cell culture of cells of the specific cell type, comprising:
providing a metabolic model of a cell of the specific cell type, the metabolic model including a plurality of intracellular metabolites, a plurality of extracellular metabolites and a plurality of intracellular and extracellular fluxes, the metabolic model comprising stoichiometric equations specifying at least one stoichiometric relationship between one among the plurality of intracellular metabolites and one among the plurality of extracellular metabolites;
at each of a first plurality of points in time during cultivation of the cell culture:
receiving a plurality of measurement values measured at said point in time, said measurement values comprising concentrations of a first set of extracellular metabolites among the plurality of extracellular metabolites in a culture medium of the cell culture and a measured cell density of the cells in the cell culture;
inputting, for each among the first set of extracellular metabolites, first measurement values corresponding to a respective second set of extracellular metabolites as input parameter values into a trained machine learning program logic—MLP—, the first measurement values being among the plurality of measurement values, and the respective second set of extracellular metabolites being among the first set of extracellular metabolites;
predicting extracellular fluxes of the first set of extracellular metabolites at a future point in time by the MLP using the received measurement values, the future point in time being a point in time subsequent to the point in time of receiving the measurement values, wherein the extracellular fluxes are uptake rates of the first set of extracellular metabolites into a cell and/or release rates of the first set of extracellular metabolites from a cell into the culture medium; and
performing metabolic flux analysis to calculate the intracellular fluxes at the future point in time using the predicted extracellular fluxes of the first set of extracellular metabolites and the stoichiometric equations of the metabolic model,
wherein
the respective second set of extracellular metabolites used as input parameter values differs for at least two among the first set of extracellular metabolites whose extracellular flux is to be determined; and
the method further includes
measuring the concentrations of all input candidate metabolites over a second plurality of points in time, wherein the input candidate metabolites comprise all extracellular metabolites that are measurably available in a reference bioreactor with a cell culture of the specific type or comprise all extracellular metabolites among the plurality of extracellular metabolites of the metabolic model;
for each respective extracellular metabolite among the first set of extracellular metabolites whose extracellular flux is to be predicted, performing a selection procedure to identify the respective second set of extracellular metabolites to be used as input parameter values for predicting the extracellular flux of the respective extracellular metabolite, the selection procedure comprising, with respect to the respective extracellular metabolite,
(a) defining a third set of extracellular metabolites, the third set comprising all of the candidate input metabolites;

(b) calculating a first relevance score of each respective candidate input metabolite among the extracellular metabolites in the third set as a function of the measured concentrations of the respective candidate input metabolite, the first relevance score indicating a predictive power of the concentration of the respective candidate input metabolite with respect to the extracellular flux of the respective candidate input metabolite;

(c) transferring only a first candidate input metabolite from the third set to a still empty fourth set of extracellular metabolites, removing the first candidate input metabolite from the third set to obtain an updated third set, the first candidate input metabolite having a highest first relevance score among the extracellular metabolites in the third set;

d) calculating a further relevance score of each respective updated candidate input metabolite among the extracellular metabolites in the updated third set as a function of the measured concentrations of the respective updated candidate input metabolite and the measured concentrations of all extracellular metabolites contained in the fourth set, the further relevance score indicating a predictive power of the concentration of the respective updated candidate input metabolite with respect to the extracellular flux of the respective updated candidate input metabolite taking into account one or more extracellular metabolites contained in the fourth set;

(e) transferring only a first updated candidate input metabolite from the updated third set to the fourth set, removing the first updated candidate input metabolite from the updated third set, the transfer taking place only if, by the transfer of the first updated candidate metabolite, the fourth set does not exceed a maximum informative redundancy limit of the metabolites contained therein with respect to prediction of the extracellular flux of the respective extracellular metabolite among the first set of extracellular metabolites, the first updated candidate input metabolite having a highest first relevance score among the extracellular metabolites in the updated third set;

(f) repeating steps d) and e) until no more metabolites can be transferred to the fourth set without the fourth set exceeding the maximum informative redundancy limit; and (g) using selectively only the metabolites transferred to the fourth set as input parameter values to predict the extracellular flux of the respective extracellular metabolite among the first set of extracellular metabolites;

determining a deviation between the calculated intracellular fluxes of at least one of the intracellular metabolites from a corresponding reference value or a corresponding reference value range; and changing a state of the bioreactor or a medium contained therein to reduce the deviation, the bioreactor including the cell culture.

2. The method according to claim 1, further comprising a generation of MLP by machine learning, wherein said generation comprises:

generating a training data set, wherein said generating comprises:

at each respective training point in time among a plurality of training points in time during the cultivation of at least one training cell culture of cells of the specific cell type:

receiving a plurality of measurement values measured at the respective training point in time, said measurement values comprising concentrations of a fifth set of extracellular metabolites of the metabolic model in the culture medium of said at least one training cell culture and a measured cell density of the cells in said at least one training cell culture;

receiving a time indication of the respective training point in time; and calculating extracellular fluxes of the fifth set of extracellular metabolites as a function of the measured values received at the respective training point in time and the measured values received at a respective preceding point in time, wherein the extracellular fluxes are uptake rates of the fifth set of extracellular metabolites into the cell and/or release rates of the fifth set of extracellular metabolites into the culture medium;

training the MLP, wherein the training comprises:

inputting the measured values received at each of the training points in time as training input parameter values to the MLP, and inputting the extracellular fluxes calculated for each of a plurality of following points in time, each respective following point in time among the plurality of following points in time following a corresponding training point in time among the plurality of training points in time, and the extracellular fluxes being calculated as output parameter values associated with the training input parameter values to the MLP; and performing a learning process by the MLP in such a way that the MLP learns to predict each respective associated output parameter value among the output parameter values based on a corresponding input training parameter value among the training input parameter values; and storing the trained MLP in a volatile or non-volatile storage medium.

3. The method according to claim 2, wherein the training data set is generated such that at each of a plurality of training points in time during the cultivation of multiple training cell cultures of cells of the specific cell type, the measured values and time specifications are received and the extracellular fluxes of the fifth set of extracellular metabolites are calculated, wherein the multiple training cell cultures are cultivated in bioreactors of different types, wherein the different types of bioreactors comprise at least two different bioreactor types from the following bioreactor types: a fed-batch bioreactor, a batch bioreactor, a perfusion reactor, a chemostat and a split-batch bioreactor.

4. The method according to claim 1, wherein the MLP includes at least one neural network.

5. The method according to claim 1, wherein the measured concentrations of the first set of extracellular metabolites are each:

an indication of volume-related content of a corresponding metabolite among the first set, in particular a mass concentration or a substance concentration, or
a value which correlates in a linear manner or at least approximately linearly with the volume-related content, in particular a corrected or normalised measured metabolite concentration or a measured flux of a corresponding metabolite among the first set.

6. The method according to claim 1, wherein the MLP includes three or more sub-MLPs, wherein each of the three or more sub-MLPs has been trained to predict the extracellular flux of a single one among the first set of extracellular metabolites and is selectively used to predict the extracellular flux of the single one among the first set of extracellular metabolites at the future point in time.

7. The method according to claim 1,
wherein the first relevance score is calculated as a partial mutual information score—PMI score—between a candidate input metabolite among the third set and the respective extracellular metabolite whose extracellular flow is to be predicted; and
wherein the further relevance score is calculated as a PMI score—between a candidate input metabolite among the third set and the respective extracellular metabolite whose extracellular flow is to be predicted, taking into account the one or more extracellular metabolites contained in the fourth set.

8. The method according to claim 1, wherein the MLP uses measured concentrations of the respective second set of extracellular metabolites as the input parameter values for predicting the extracellular flux of each respective extracellular metabolite among the first set of extracellular metabolites, wherein the respective second set of extracellular metabolites comprises at least one amino acid.

9. The method according to claim 1, wherein the plurality of first points in time are separated by time intervals of 10 minutes to 48 hours.

10. The method according to claim 1, wherein the cell type is a genetically modified cell type which is maintained and/or grown in the bioreactor for the purpose of obtaining a biomolecule.

11. The method according to claim 1, wherein at each of the future points in time a calculation of a plurality of the intracellular fluxes of the metabolic model is performed.

12. The method according to claim 1, further comprising:
identifying one or more intracellular metabolites of the metabolic model whose calculated intracellular fluxes deviate from a respective reference value or reference value range by more than a threshold value, the one or more intracellular metabolites including the at least one of the intracellular metabolites, and the respective reference value or reference value range including the corresponding reference value; and
automatically identifying that intracellular flux which acts as a limiting factor for cell growth or production of a desired biomolecule.

13. The method according to claim 1, further comprising:
comparing the calculated intracellular fluxes with reference values or reference value ranges for intracellular fluxes of respective one or more intracellular metabolites to determine the deviation, the respective one or more intracellular metabolites including the at least one of the intracellular metabolites, and the reference values or reference value ranges including the corresponding reference value;
issuing a warning if the deviation of the calculated intracellular flux of at the least one of the intracellular metabolites from its respective reference value or reference value range exceeds a limit value; and
sending a control command to the bioreactor to automatically initiate steps which change the state of the bioreactor or the medium contained therein in such a way as to reduce the deviation, wherein the automatically initiated steps include in particular a change in a quantity and/or a change in a composition of a culture medium.

14. The method according to claim 13, further comprising:
identifying a reaction within the metabolic model of the cells which acts as a limiting factor for cell growth or production of a desired biomolecule; and
automatically adding of selectively those substances which modify the intracellular flux acting as a limiting factor in such a way as to promote cell growth or production of the desired biomolecule or a quality of the biomolecule.

15. The method according to claim 1, further comprising:
calculating current extracellular fluxes of two or more among the first set of extracellular metabolites from the concentrations of the first set of extracellular metabolites measured at a current point in time and at a previous point in time;
performing a further metabolic flux analysis to calculate current intracellular fluxes at the current point in time using the calculated current extracellular fluxes of the two or more among the first set of extracellular metabolites and the stoichiometric equations of the metabolic model; and
using the calculated current intracellular fluxes as a characterization of a current metabolic state of the cells of the cell culture.

16. The method according to claim 1,
wherein a concentration of lactate dehydrogenase—LDH—measured in the culture medium of the cell culture is further received at each of the first points in time during the cultivation of the cell culture; and
wherein the prediction of the extracellular fluxes of the first set of extracellular metabolites at each of the future points in time by the MLP is made using a corrected rather than the measured cell density, wherein the calculation of the corrected cell density comprises for each of the first points in time:
calculating the density of lysed cells in the culture medium of the cell culture as a function of the measured LDH concentration, said function being an empirically determined, heuristic and linear function representing the relationship of the LDH concentration in the culture medium to a number of the lysed cells of that specific cell type; and
calculating the corrected cell density as a sum of the measured cell density in the culture medium and the calculated density of the lysed cells.

17. A system, comprising:
one or more processors;
a bioreactor, the bioreactor including a cell culture of cells of a specific cell type;
a first interface for receiving measurements from a bioreactor containing the cell culture; and
a volatile or non-volatile storage medium comprising:
a metabolic model of a cell of the specific cell type, the metabolic model including a plurality of intracellular metabolites, a plurality of extracellular metabolites and a plurality of intracellular and extracellular fluxes, the metabolic model including stoichiometric equations specifying at least one stoichiometric relationship between one among the plurality of intracellular metabolites and one among the plurality of extracellular metabolites;
a trained machine learning program logic—MLP—; and
a program logic that, when executed by the one or more processors, causes the one or more processors to perform a method at each of a first plurality of points in time during cultivation of the cell culture, the method comprising:
  receiving a plurality of measurement values measured at said point in time via the first interface, the measurement values comprising concentrations of a first set of extracellular metabolites among the plurality of extracellular metabolites in a culture medium of the cell culture and a measured cell density of the cells in the cell culture;
  inputting, for each among the first set of extracellular metabolites, first measurement values corresponding to a respective second set of extracellular metabolites as input parameter values to the MLP, the first measurement values being among the plurality of measurement values, and the respective second set of extracellular metabolites being among the first set of extracellular metabolites;
  predicting extracellular fluxes of the first set of extracellular metabolites at a future point in time by the MLP using the received measurement values, the future point in time being a point in time subsequent to the time of receipt of the measurement values, wherein the extracellular fluxes are uptake rates of the first set of extracellular metabolites into a cell and/or release rates of the first set of extracellular metabolites from a cell into the culture medium; and
  performing metabolic flux analysis to calculate the intracellular fluxes at the future point in time using the predicted extracellular fluxes and the stoichiometric equations of the metabolic model,
wherein
  the respective second set of extracellular metabolites used as input parameter values differs for at least two among the first set of extracellular metabolites whose extracellular flux is to be determined; and
  the method further includes
    measuring the concentrations of all input candidate metabolites over a second plurality of points in time, wherein the input candidate metabolites comprise all extracellular metabolites that are measurably available in a reference bioreactor with a cell culture of the specific type or comprise all extracellular metabolites among the plurality of extracellular metabolites of the metabolic model;
    for each respective extracellular metabolite among the first set of extracellular metabolites whose extracellular flux is to be predicted, performing a selection procedure to identify the respective second set of extracellular metabolites to be used as input parameter values for predicting the extracellular flux of the respective extracellular metabolite, the selection procedure comprising, with respect to the respective extracellular metabolite,
      (a) defining a third set of extracellular metabolites, the third set comprising all of the candidate input metabolites;
      (b) calculating a first relevance score of each respective candidate input metabolite among the extracellular metabolites in the third set as a function of the measured concentrations of the respective candidate input metabolite, the first relevance score indicating a predictive power of the concentration of the respective candidate input metabolite with respect to the extracellular flux of the respective candidate input metabolite;
      (c) transferring only a first candidate input metabolite from the third set to a still empty fourth set of extracellular metabolites, removing the first candidate input metabolite from the third set to obtain an updated third set, the first candidate input metabolite having a highest first relevance score among the extracellular metabolites in the third set;
      d) calculating a further relevance score of each respective updated candidate input metabolite among the extracellular metabolites in the updated third set as a function of the measured concentrations of the respective updated candidate input metabolite and the measured concentrations of all extracellular metabolites contained in the fourth set, the further relevance score indicating a predictive power of the concentration of the respective updated candidate input metabolite with respect to the extracellular flux of the respective updated candidate input metabolite taking into account one or more extracellular metabolites contained in the fourth set;
      (e) transferring only a first updated candidate input metabolite from the updated third set to the fourth set, removing the first updated candidate input metabolite from the updated third set, the transfer taking place only if, by the transfer of the first updated candidate metabolite, the fourth set does not exceed a maximum informative redundancy limit of the metabolites contained therein with respect to prediction of the extracellular flux of respective extracellular metabolite among the first set of extracellular metabolites, the first updated candidate input metabolite having a highest first relevance score among the extracellular metabolites in the updated third set;
      (f) repeating steps d) and e) until no more metabolites can be transferred to the fourth set without the fourth set exceeding the maximum informative redundancy limit; and
      (g) using selectively only the metabolites transferred to the fourth set as input parameter values to predict the extracellular flux of the respective extracellular metabolite among the first set of extracellular metabolites;
    determining a deviation between the calculated intracellular fluxes of at least one of the intracellular metabolites from a corresponding reference value or a corresponding reference value range; and
    changing a state of the bioreactor or a medium contained therein to reduce the deviation, the bioreactor including the cell culture.

18. The system according to claim 17, wherein the method further comprises a generation of MLP by machine learning, wherein said generation comprises:
generating a training data set, wherein said generating comprises:
at each respective training point in time among a plurality of training points in time during cultivation of at least one training cell culture of cells of the specific cell type:
receiving a plurality of measurement values measured at the respective training point in time, said measurement values comprising concentrations of a fifth set of extracellular metabolites of the metabolic model in the culture medium of said at least one training cell culture and a measured cell density of the cells in said at least one training cell culture;
receiving a time indication of the respective training point in time; and
calculating extracellular fluxes of the fifth set of extracellular metabolites as a function of the measured values received at the respective training point in time and the measured values received at a respective preceding point in time, wherein the extracellular fluxes are uptake rates of the fifth set of extracellular metabolites into the cell and/or release rates of the fifth set of extracellular metabolites into the culture medium;
training the MLP, wherein the training comprises:
inputting the measured values received at each of the training points in time as training input parameter values to the MLP, and inputting the extracellular fluxes calculated for each of a plurality of following points in time, each respective following point in time among the plurality of following points in time following a corresponding training point in time among the plurality of training points in time, and the extracellular fluxes being calculated as output parameter values associated with the training input parameter values to the MLP; and
performing a learning process by the MLP in such a way that the MLP learns to predict each respective associated output parameter value among the output parameter values based on a corresponding input training parameter value among the training input parameter values; and
storing the trained MLP in the volatile or non-volatile storage medium.

19. The system according to claim 18, wherein the training data set is generated such that at each of a plurality of training points in time during cultivation of multiple training cell cultures of cells of the specific cell type, the measured values and time specifications are received and the extracellular fluxes of the fifth set of extracellular metabolites are calculated, wherein the multiple training cell cultures are cultivated in bioreactors of different types, wherein the different types of bioreactors comprise at least two different bioreactor types from the following bioreactor types: a fed-batch bioreactor, a batch bioreactor, a perfusion reactor, a chemostat and a split-batch bioreactor.

* * * * *